(12) United States Patent
Nedvěd et al.

(10) Patent No.: US 12,279,801 B2
(45) Date of Patent: *Apr. 22, 2025

(54) PULSED FIELD ABLATION DEVICE AND METHOD

(71) Applicant: BTL Medical Development a.s., Prague (CZ)

(72) Inventors: Vojtěch Nedvěd, Tři Sekery (CZ); Jiří Dašek, Vápno u Přelouče (CZ); Martin Hanuliak, Prague (CZ); Ahmad Hijazi, Prague (CZ)

(73) Assignee: BTL Medical Development a.s., Prague (CZ)

( * ) Notice: Subject to any disclaimer, the term of this patent is extended or adjusted under 35 U.S.C. 154(b) by 0 days.

This patent is subject to a terminal disclaimer.

(21) Appl. No.: 18/603,417

(22) Filed: Mar. 13, 2024

(65) Prior Publication Data
US 2024/0216059 A1 Jul. 4, 2024

Related U.S. Application Data

(63) Continuation of application No. 18/422,443, filed on Jan. 25, 2024, which is a continuation of application No. PCT/IB2023/059957, filed on Oct. 4, 2023.
(Continued)

(51) Int. Cl.
*A61B 18/18* (2006.01)
*A61B 18/00* (2006.01)
(Continued)

(52) U.S. Cl.
CPC .......... *A61B 18/00* (2013.01); *A61B 18/1206* (2013.01); *A61B 18/1492* (2013.01);
(Continued)

(58) Field of Classification Search
CPC ............ A61B 18/1206; A61B 18/1492; A61B 2018/00083; A61B 2018/00166;
(Continued)

(56) References Cited

U.S. PATENT DOCUMENTS

| 5,876,336 A | 3/1999 | Swanson |
| 5,935,079 A | 8/1999 | Swanson |

(Continued)

FOREIGN PATENT DOCUMENTS

| CA | 2765976 | 8/2012 |
| CN | 106877729 A | 6/2017 |

(Continued)

OTHER PUBLICATIONS

N. Klauke, G. Smith, a J. M. Cooper, "Regional Electroporation of Single Cardiac Myocytes in a Focused Electric Field", Anal. Chem., roč. 82, č. 2, s. 585-592, led. 2010, doi: 10.1021/ac901886j.
(Continued)

*Primary Examiner* — Michael F Peffley
*Assistant Examiner* — Amanda L Zink
(74) *Attorney, Agent, or Firm* — Riverside Law LLP

(57) ABSTRACT

An ablation device and method for pulsed field ablation, the device comprising a catheter including an expandable basket, a set of electrodes formed on the expandable basket, and a pulse generator suitable for generating electric pulses wherein the pulse generator being in electrical connection with the set of electrodes. The expandable basket is formed of a braided mesh of filaments, wherein the filaments are made of nonconductive material, wherein at least portion of the filaments comprises a lumen, and wherein the lumen comprises melted material, wherein the filaments further include electrodes and conductive wires. The conductive wires at least partially lead inside of the lumen of the filaments, and are electrically connected to the electrodes.

30 Claims, 39 Drawing Sheets

Related U.S. Application Data

(60) Provisional application No. 63/378,405, filed on Oct. 5, 2022.

(51) Int. Cl.
  *A61B 18/12* (2006.01)
  *A61B 18/14* (2006.01)
  *A61B 17/00* (2006.01)

(52) U.S. Cl.
  CPC ............ *A61B 2017/00154* (2013.01); *A61B 2018/00351* (2013.01); *A61B 2018/00577* (2013.01); *A61B 2018/00613* (2013.01); *A61B 2018/00648* (2013.01); *A61B 2018/0066* (2013.01); *A61B 2018/00666* (2013.01); *A61B 2018/00708* (2013.01); *A61B 2018/0072* (2013.01); *A61B 2018/00767* (2013.01); *A61B 2018/00791* (2013.01); *A61B 2018/00827* (2013.01); *A61B 2018/00875* (2013.01); *A61B 2018/00892* (2013.01); *A61B 2018/124* (2013.01); *A61B 2018/126* (2013.01); *A61B 2018/1405* (2013.01)

(58) Field of Classification Search
  CPC ........... A61B 2018/00267; A61B 2018/00351; A61B 2018/00577; A61B 2018/00613; A61B 2018/126; A61B 2018/146
  See application file for complete search history.

(56) References Cited

U.S. PATENT DOCUMENTS

| | | | |
|---|---|---|---|
| 5,997,526 | A | 12/1999 | Giba |
| 6,522,930 | B1 * | 2/2003 | Schaer ............... A61B 18/1492 607/104 |
| 6,546,270 | B1 | 4/2003 | Goldin |
| 6,569,160 | B1 | 5/2003 | Goldin |
| 6,837,886 | B2 | 1/2005 | Collins |
| 7,044,135 | B2 | 5/2006 | Lesh |
| 7,115,122 | B1 | 10/2006 | Swanson |
| 7,195,628 | B2 | 3/2007 | Falkenberg |
| 7,255,695 | B2 | 8/2007 | Falwell |
| 7,670,297 | B1 | 3/2010 | Hauck |
| 7,718,409 | B2 | 5/2010 | Rubinsky |
| 7,727,229 | B2 | 6/2010 | He |
| 7,846,157 | B2 | 12/2010 | Kozel |
| 7,918,850 | B2 | 4/2011 | Govari |
| 8,007,495 | B2 | 8/2011 | McDaniel |
| 8,024,024 | B2 | 9/2011 | Viswanathan |
| 8,109,926 | B2 | 2/2012 | Azure |
| 8,114,070 | B2 | 2/2012 | Rubinsky |
| 8,221,411 | B2 | 7/2012 | Francischelli |
| 8,315,696 | B2 | 11/2012 | Schwartz |
| 8,454,589 | B2 | 6/2013 | Deno |
| 8,489,184 | B2 | 7/2013 | Wilfley |
| 8,500,713 | B2 | 8/2013 | Ferek-Petric |
| 8,504,132 | B2 | 8/2013 | Friedman |
| 8,603,087 | B2 | 12/2013 | Rubinsky |
| 8,620,423 | B2 | 12/2013 | Demarais |
| 8,647,338 | B2 | 2/2014 | Chornenky |
| 8,903,478 | B2 | 12/2014 | Macadam |
| 8,903,488 | B2 | 12/2014 | Callas |
| 8,926,606 | B2 | 1/2015 | Davalos |
| 8,945,116 | B2 | 2/2015 | Macadam |
| 9,005,100 | B2 | 4/2015 | Gnanashanmugam |
| 9,060,778 | B2 | 6/2015 | Condie |
| 9,089,341 | B2 | 7/2015 | Chomas |
| 9,095,350 | B2 | 8/2015 | Condie |
| 9,168,096 | B2 | 10/2015 | Kreindel |
| 9,198,733 | B2 | 12/2015 | Neal, II |
| 9,314,620 | B2 | 4/2016 | Long |
| 9,333,031 | B2 | 5/2016 | Salahieh |
| 9,345,538 | B2 | 5/2016 | Deem |
| 9,351,790 | B2 | 5/2016 | Zemel |
| 9,387,031 | B2 | 7/2016 | Stewart |
| 9,427,167 | B2 | 8/2016 | Maskara |
| 9,724,170 | B2 | 8/2017 | Mickelsen |
| 9,788,888 | B2 | 10/2017 | Bakos |
| 9,861,802 | B2 | 1/2018 | Mickelsen |
| 9,877,781 | B2 | 1/2018 | Grasse |
| 9,918,790 | B2 | 3/2018 | Zemlin |
| 9,987,081 | B1 | 6/2018 | Bowers |
| 9,993,178 | B2 | 6/2018 | Panescu |
| 9,999,465 | B2 | 6/2018 | Long |
| 10,080,602 | B2 | 9/2018 | Wittkampf |
| 10,130,423 | B1 | 11/2018 | Viswanathan |
| 10,130,819 | B2 | 11/2018 | Callas |
| 10,143,399 | B2 | 12/2018 | Condie |
| 10,143,512 | B2 | 12/2018 | Rubinsky |
| 10,154,876 | B2 | 12/2018 | Callas |
| 10,166,071 | B2 | 1/2019 | Sherman |
| 10,245,098 | B2 | 4/2019 | Davalos |
| 10,258,406 | B2 | 4/2019 | Long |
| 10,285,755 | B2 | 5/2019 | Stewart |
| 10,314,649 | B2 | 6/2019 | Bakos |
| 10,335,224 | B2 | 7/2019 | Chornenky |
| 10,342,598 | B2 | 7/2019 | Long |
| 10,342,600 | B2 | 7/2019 | Callas |
| 10,362,956 | B2 | 7/2019 | Chauhan |
| 10,433,908 | B2 | 10/2019 | Viswanathan |
| 10,470,822 | B2 | 11/2019 | Garcia |
| 10,471,254 | B2 | 11/2019 | Sano |
| 10,507,057 | B2 | 12/2019 | Harlev |
| 10,531,914 | B2 | 1/2020 | Stewart |
| 10,556,102 | B1 | 2/2020 | Rotman |
| 10,569,081 | B2 | 2/2020 | Howard |
| 10,589,092 | B2 | 3/2020 | Sano |
| 10,617,867 | B2 | 4/2020 | Viswanathan |
| 10,625,080 | B1 | 4/2020 | Viswanathan |
| 10,687,892 | B2 | 6/2020 | Long |
| 10,688,300 | B2 | 6/2020 | Paul |
| 10,842,572 | B1 | 11/2020 | Viswanathan |
| 10,849,677 | B2 | 12/2020 | Fraasch |
| 10,856,936 | B2 | 12/2020 | Willard |
| 10,874,451 | B2 | 12/2020 | Athos |
| 10,893,903 | B2 | 1/2021 | Koblish |
| 10,994,133 | B2 | 5/2021 | Sano |
| 11,033,321 | B2 | 6/2021 | Davalos |
| 11,052,246 | B2 | 7/2021 | Stewart |
| 11,065,047 | B2 | 7/2021 | Paré |
| 11,229,478 | B2 | 1/2022 | Howard |
| 11,253,732 | B2 | 2/2022 | Mayer |
| 11,298,175 | B2 | 4/2022 | Konings |
| 11,318,306 | B2 | 5/2022 | Stewart |
| 11,376,064 | B2 | 7/2022 | Rankin |
| 11,382,681 | B2 | 7/2022 | Arena |
| 11,446,082 | B2 | 9/2022 | Blanck |
| 11,589,919 | B2 | 2/2023 | Long |
| 11,607,526 | B2 | 3/2023 | Oren |
| 11,612,424 | B2 | 3/2023 | Fraasch |
| 11,633,121 | B2 | 4/2023 | Howard |
| 11,701,021 | B2 | 7/2023 | Schmidt |
| 11,701,171 | B2 | 7/2023 | Schultheis |
| 11,738,200 | B2 | 8/2023 | Raju |
| 11,793,565 | B2 | 10/2023 | Govari |
| 11,819,265 | B2 | 11/2023 | Govari |
| 11,911,087 | B2 | 2/2024 | Foxall |
| 11,911,096 | B2 | 2/2024 | Govari |
| 11,918,280 | B2 | 3/2024 | Sherman |
| 11,950,840 | B2 | 4/2024 | Govari |
| 12,004,804 | B2 | 6/2024 | Govari |
| 12,016,623 | B2 | 6/2024 | Belalcazar |
| 12,042,208 | B2 | 7/2024 | Viswanathan |
| 12,042,215 | B2 | 7/2024 | Govari |
| 12,048,480 | B2 | 7/2024 | Stewart |
| 12,070,265 | B2 | 8/2024 | Schweitzer |
| 12,076,071 | B2 | 9/2024 | Miller-Tait |
| 12,114,918 | B2 | 10/2024 | Govari |
| 12,144,541 | B2 | 11/2024 | Viswanathan |
| 12,150,700 | B2 | 11/2024 | Stewart |
| 2004/0116965 | A1 | 6/2004 | Falkenberg |
| 2006/0293731 | A1 | 12/2006 | Rubinsky |

(56) References Cited

U.S. PATENT DOCUMENTS

| | | | |
|---|---|---|---|
| 2009/0198231 A1 | 8/2009 | Esser | |
| 2009/0247933 A1* | 10/2009 | Maor | A61B 18/14 604/20 |
| 2010/0179530 A1* | 7/2010 | Long | A61B 18/1492 606/41 |
| 2012/0130369 A1 | 5/2012 | Cadossi | |
| 2013/0030425 A1 | 1/2013 | Stewart | |
| 2015/0066010 A1 | 3/2015 | McLawhorn | |
| 2015/0073401 A1 | 3/2015 | Kreindel | |
| 2015/0216588 A1 | 8/2015 | Deem | |
| 2015/0250399 A1 | 9/2015 | Laughner | |
| 2015/0289923 A1 | 10/2015 | Davalos | |
| 2015/0320481 A1* | 11/2015 | Cosman, Jr. | A61B 34/10 606/35 |
| 2016/0051324 A1 | 2/2016 | Stewart | |
| 2016/0058493 A1 | 3/2016 | Neal, II | |
| 2016/0113709 A1 | 4/2016 | Maor | |
| 2016/0143686 A1 | 5/2016 | Tunay | |
| 2016/0278858 A1 | 9/2016 | Stewart | |
| 2016/0287136 A1 | 10/2016 | Condie | |
| 2016/0324573 A1 | 11/2016 | Mickelson | |
| 2016/0331441 A1 | 11/2016 | Konings | |
| 2016/0361109 A1 | 12/2016 | Weaver | |
| 2017/0007157 A1 | 1/2017 | Gross | |
| 2017/0049508 A1 | 2/2017 | Long | |
| 2017/0100075 A1 | 4/2017 | Eliason | |
| 2017/0189106 A1* | 7/2017 | Schuler | A61B 18/1492 |
| 2017/0202469 A1 | 7/2017 | Scharf | |
| 2017/0215953 A1 | 8/2017 | Long | |
| 2017/0224415 A1 | 8/2017 | Dong | |
| 2018/0132922 A1 | 5/2018 | Neal, II | |
| 2018/0193090 A1 | 7/2018 | De La Rama | |
| 2018/0214202 A1 | 8/2018 | Howard | |
| 2018/0221085 A1 | 8/2018 | Blanck | |
| 2018/0296264 A1 | 10/2018 | Desimone | |
| 2018/0303543 A1 | 10/2018 | Stewart | |
| 2018/0360534 A1 | 12/2018 | Teplitsky | |
| 2019/0021620 A1 | 1/2019 | Olson | |
| 2019/0038171 A1 | 2/2019 | Howard | |
| 2019/0046791 A1 | 2/2019 | Ebbers | |
| 2019/0060632 A1 | 2/2019 | Asirvatham | |
| 2019/0183561 A1 | 6/2019 | Hobbs | |
| 2019/0201688 A1 | 7/2019 | Olson | |
| 2019/0209235 A1 | 7/2019 | Stewart | |
| 2019/0216538 A1 | 7/2019 | Wittkampf | |
| 2019/0232048 A1 | 8/2019 | Latouche | |
| 2019/0254735 A1 | 8/2019 | Stewart | |
| 2019/0262071 A1 | 8/2019 | Thom | |
| 2019/0282294 A1 | 9/2019 | Davalos | |
| 2019/0321091 A1 | 10/2019 | Zemel | |
| 2019/0328446 A1 | 10/2019 | Callas | |
| 2019/0350649 A1 | 11/2019 | Sutermeister | |
| 2019/0365463 A1 | 12/2019 | Govari | |
| 2020/0008869 A1 | 1/2020 | Byrd | |
| 2020/0008870 A1 | 1/2020 | Gruba | |
| 2020/0015890 A1 | 1/2020 | To | |
| 2020/0114121 A1 | 4/2020 | Leeflang | |
| 2020/0146741 A1 | 5/2020 | Long | |
| 2020/0155838 A1 | 5/2020 | Howard | |
| 2020/0179046 A1 | 6/2020 | Wittkampf | |
| 2020/0205890 A1 | 7/2020 | Harlev | |
| 2020/0275973 A1 | 9/2020 | O'Brien | |
| 2020/0297418 A1 | 9/2020 | Stewart | |
| 2020/0298008 A1 | 9/2020 | Asirvatham | |
| 2020/0397505 A1 | 12/2020 | Viswanathan | |
| 2020/0398048 A1* | 12/2020 | Krimsky | A61N 1/37 |
| 2021/0022794 A1 | 1/2021 | Viswanathan | |
| 2021/0045805 A1 | 2/2021 | Govari | |
| 2021/0077188 A1 | 3/2021 | Long | |
| 2021/0137587 A1 | 5/2021 | Olson | |
| 2021/0137592 A1 | 5/2021 | Raju | |
| 2021/0161582 A1 | 6/2021 | Byrd | |
| 2021/0162210 A1 | 6/2021 | Altmann | |
| 2021/0169421 A1 | 6/2021 | Govari | |
| 2021/0177491 A1 | 6/2021 | Onik | |
| 2021/0177503 A1 | 6/2021 | Altmann | |
| 2021/0186592 A1 | 6/2021 | Rubinsky | |
| 2021/0186593 A1 | 6/2021 | Altmann | |
| 2021/0220038 A1 | 7/2021 | Kenneth | |
| 2021/0275806 A1 | 9/2021 | Paul | |
| 2021/0282847 A1 | 9/2021 | Viswanathan | |
| 2021/0290172 A1 | 9/2021 | Viswanathan | |
| 2021/0322086 A1 | 10/2021 | Gorzycki | |
| 2021/0338305 A1 | 11/2021 | Chen | |
| 2021/0338320 A1 | 11/2021 | Viswanathan | |
| 2021/0369338 A1 | 12/2021 | Govari | |
| 2021/0378734 A1 | 12/2021 | Govari | |
| 2021/0393327 A1 | 12/2021 | Eyster | |
| 2021/0401491 A1 | 12/2021 | Altmann | |
| 2022/0000546 A1 | 1/2022 | Viswanathan | |
| 2022/0000550 A1 | 1/2022 | Henschel | |
| 2022/0008123 A1 | 1/2022 | Altmann | |
| 2022/0008128 A1 | 1/2022 | Zhou | |
| 2022/0022952 A1 | 1/2022 | Koop | |
| 2022/0031385 A1 | 2/2022 | Govari | |
| 2022/0047326 A1 | 2/2022 | Altmann | |
| 2022/0071693 A1 | 3/2022 | Govari | |
| 2022/0071699 A1 | 3/2022 | Viswanathan | |
| 2022/0087736 A1 | 3/2022 | Govari | |
| 2022/0117655 A1 | 4/2022 | Govari | |
| 2022/0133389 A1 | 5/2022 | Howard | |
| 2022/0133405 A1 | 5/2022 | Mickelsen | |
| 2022/0161027 A1 | 5/2022 | Aycock | |
| 2022/0168594 A1 | 6/2022 | Mayer | |
| 2022/0175445 A1 | 6/2022 | Sutermeister | |
| 2022/0183750 A1 | 6/2022 | Bai | |
| 2022/0192737 A1 | 6/2022 | Altmann | |
| 2022/0192741 A1 | 6/2022 | Reinders | |
| 2022/0249157 A1 | 8/2022 | Viswanathan | |
| 2022/0257196 A1 | 8/2022 | Massmann | |
| 2022/0287764 A1 | 9/2022 | Govari | |
| 2022/0296881 A1 | 9/2022 | Asirvatham | |
| 2022/0338925 A1 | 10/2022 | Stewart | |
| 2022/0370119 A1 | 11/2022 | Govari | |
| 2022/0370122 A1 | 11/2022 | Smail | |
| 2022/0370128 A1 | 11/2022 | Altmann | |
| 2023/0000550 A1* | 1/2023 | Nedved | A61B 18/1206 |
| 2023/0009573 A1 | 1/2023 | Van Niekerk | |
| 2023/0012307 A1 | 1/2023 | Harlev | |
| 2023/0049942 A1 | 2/2023 | Narayan | |
| 2023/0051310 A1 | 2/2023 | Govari | |
| 2023/0052114 A1 | 2/2023 | Marass | |
| 2023/0089295 A1 | 3/2023 | Assaf | |
| 2023/0105390 A1 | 4/2023 | Gutbrod | |
| 2023/0149071 A1 | 5/2023 | Fraasch | |
| 2023/0172650 A1 | 6/2023 | Castellvi | |
| 2023/0181242 A1 | 6/2023 | Govari | |
| 2023/0190198 A1 | 6/2023 | Pederson | |
| 2023/0190365 A1 | 6/2023 | Govari | |
| 2023/0200901 A1 | 6/2023 | Harlev | |
| 2023/0210437 A1 | 7/2023 | Beeckler | |
| 2023/0218340 A1 | 7/2023 | Werneth | |
| 2023/0225790 A1 | 7/2023 | Okarski | |
| 2023/0226638 A1 | 7/2023 | Datta | |
| 2023/0240745 A1 | 8/2023 | Jan | |
| 2023/0248412 A1 | 8/2023 | Govari | |
| 2023/0255684 A1 | 8/2023 | Schmidt | |
| 2023/0284957 A1 | 9/2023 | Bonyak | |
| 2023/0301707 A1 | 9/2023 | Okarski | |
| 2023/0301712 A1 | 9/2023 | Okarski | |
| 2023/0301713 A1 | 9/2023 | Okarski | |
| 2023/0310059 A1 | 10/2023 | Hirao | |
| 2023/0310061 A1 | 10/2023 | Stewart | |
| 2023/0310072 A1 | 10/2023 | Stewart | |
| 2023/0329769 A1 | 10/2023 | Fischbach | |
| 2023/0329772 A1 | 10/2023 | Byrd | |
| 2023/0330421 A1 | 10/2023 | Callas | |
| 2023/0346460 A1 | 11/2023 | Govari | |
| 2023/0346467 A1 | 11/2023 | Altmann | |
| 2023/0371836 A1 | 11/2023 | Govari | |
| 2023/0372005 A1 | 11/2023 | Ng | |
| 2023/0380897 A1 | 11/2023 | Liu | |
| 2023/0389984 A1 | 12/2023 | Redjebian | |
| 2023/0397952 A1 | 12/2023 | Turovskiy | |

(56) References Cited

U.S. PATENT DOCUMENTS

| | | |
|---|---|---|
| 2023/0404644 A1 | 12/2023 | Shamis |
| 2023/0404663 A1 | 12/2023 | Sharma |
| 2023/0414270 A1 | 12/2023 | Gandionco |
| 2023/0414276 A1 | 12/2023 | Laske |
| 2023/0414277 A1 | 12/2023 | Kelly |
| 2024/0016536 A1 | 1/2024 | Kato |
| 2024/0016540 A1 | 1/2024 | Sigg |
| 2024/0065758 A1 | 2/2024 | Chen |
| 2024/0081900 A1 | 3/2024 | Sakaki |
| 2024/0156524 A1 | 5/2024 | Ebrahimi |
| 2024/0164686 A1 | 5/2024 | Ghosalker |
| 2024/0164833 A1 | 5/2024 | Turovskiy |
| 2024/0164834 A1 | 5/2024 | Olson |
| 2024/0180614 A1 | 6/2024 | Keyes |
| 2024/0189016 A1 | 6/2024 | Organ |
| 2024/0189021 A1 | 6/2024 | Marziiano |
| 2024/0197391 A1 | 6/2024 | Okarski |
| 2024/0197392 A1 | 6/2024 | Van Niekerk |
| 2024/0197393 A1 | 6/2024 | Kingston |
| 2024/0197394 A1 | 6/2024 | Hagstrom |
| 2024/0206943 A1 | 6/2024 | Govari |
| 2024/0215919 A1 | 7/2024 | Govari |
| 2024/0216039 A1 | 7/2024 | Panescu |
| 2024/0216049 A1 | 7/2024 | Beeckler |
| 2024/0216051 A1 | 7/2024 | Agnew |
| 2024/0216056 A1 | 7/2024 | Keyes |
| 2024/0216075 A1 | 7/2024 | Roseberry |
| 2024/0225726 A1 | 7/2024 | Govari |
| 2024/0226546 A1 | 7/2024 | Olson |
| 2024/0238041 A1 | 7/2024 | Shuros |
| 2024/0252225 A1 | 8/2024 | Fraasch |
| 2024/0277398 A1 | 8/2024 | Zhao |
| 2024/0277404 A1 | 8/2024 | Shuros |
| 2024/0299073 A1 | 9/2024 | Jais |
| 2024/0315769 A1 | 9/2024 | Mickelsen |
| 2024/0335231 A1 | 10/2024 | Govari |
| 2024/0341843 A1 | 10/2024 | Hagstrom |
| 2024/0350187 A1 | 10/2024 | Waldstreicher |
| 2024/0350192 A1 | 10/2024 | Sharma |
| 2024/0366301 A1 | 11/2024 | Govari |
| 2024/0390056 A1 | 11/2024 | Agnew |

FOREIGN PATENT DOCUMENTS

| | | |
|---|---|---|
| CN | 206992984 U | 2/2018 |
| CN | 109124759 | 1/2019 |
| CN | 109124760 | 1/2019 |
| CN | 109171947 | 1/2019 |
| CN | 109661210 | 4/2019 |
| CN | 209316045 U | 8/2019 |
| CN | 109124759 B | 12/2019 |
| CN | 109124760 B | 12/2020 |
| CN | 112022331 | 12/2020 |
| CN | 113476136 A | 10/2021 |
| CN | 113729918 A | 12/2021 |
| CN | 113952026 A | 1/2022 |
| CN | 114041873 A | 2/2022 |
| CN | 113974823 B | 4/2022 |
| CN | 114271926 A | 4/2022 |
| CN | 114271931 A | 4/2022 |
| CN | 114305660 A | 4/2022 |
| CN | 114343834 A | 4/2022 |
| CN | 114404035 A | 4/2022 |
| CN | 114469308 A | 5/2022 |
| CN | 114469327 A | 5/2022 |
| CN | 115580269 | 1/2023 |
| CN | 116672064 | 9/2023 |
| CN | 116687544 | 9/2023 |
| CN | 116687551 | 9/2023 |
| CZ | 33133 U1 | 8/2019 |
| CZ | 33134 | 8/2019 |
| CZ | 308415 | 8/2020 |
| DE | 102021121228 A1 | 3/2022 |
| EP | 358336 | 3/1990 |
| EP | 1613387 B1 | 1/2008 |
| EP | 1189544 B1 | 1/2009 |
| EP | 1415608 B1 | 2/2009 |
| EP | 1284670 B1 | 6/2009 |
| EP | 0957773 B1 | 6/2011 |
| EP | 1210023 B1 | 1/2012 |
| EP | 1971285 B1 | 1/2012 |
| EP | 2429435 A1 | 3/2012 |
| EP | 2736432 B1 | 3/2016 |
| EP | 1171189 B1 | 5/2016 |
| EP | 3071137 A1 | 9/2016 |
| EP | 3086838 A1 | 11/2016 |
| EP | 3091925 A1 | 11/2016 |
| EP | 3142584 A1 | 3/2017 |
| EP | 2598066 B1 | 9/2017 |
| EP | 3089687 B1 | 6/2018 |
| EP | 3368135 A1 | 9/2018 |
| EP | 2474281 B1 | 3/2019 |
| EP | 3456278 A2 | 3/2019 |
| EP | 3459480 A1 | 3/2019 |
| EP | 2770930 B1 | 4/2019 |
| EP | 2629690 B1 | 7/2019 |
| EP | 3135237 B1 | 7/2019 |
| EP | 3212270 B1 | 9/2019 |
| EP | 3534816 A1 | 9/2019 |
| EP | 3573559 | 12/2019 |
| EP | 3610788 A1 | 2/2020 |
| EP | 3378427 B1 | 9/2020 |
| EP | 3742997 | 12/2020 |
| EP | 3753516 A1 | 12/2020 |
| EP | 3758638 | 1/2021 |
| EP | 3517031 B1 | 5/2021 |
| EP | 3841999 | 6/2021 |
| EP | 3944831 | 2/2022 |
| EP | 3960105 | 3/2022 |
| EP | 3984484 | 4/2022 |
| EP | 3986307 | 4/2022 |
| EP | 4030992 A1 | 7/2022 |
| EP | 4039210 | 8/2022 |
| EP | 4065004 | 10/2022 |
| EP | 4072454 | 10/2022 |
| EP | 4151168 | 3/2023 |
| EP | 4215141 | 7/2023 |
| EP | 4215142 | 7/2023 |
| EP | 4215144 | 7/2023 |
| EP | 4215145 | 7/2023 |
| EP | 4268750 | 11/2023 |
| EP | 4280988 | 11/2023 |
| EP | 4393400 | 7/2024 |
| EP | 4412549 | 8/2024 |
| ES | 2751156 | 3/2020 |
| HK | 40060966 | 3/2023 |
| IL | 299866 | 8/2023 |
| IL | 299868 | 8/2023 |
| JP | 2017140446 A | 8/2017 |
| JP | 2018089431 A | 6/2018 |
| JP | 2018161471 | 10/2018 |
| JP | 2020018606 | 2/2020 |
| JP | 2023164368 | 11/2023 |
| JP | 2024084443 | 6/2024 |
| JP | 2024095491 | 7/2024 |
| WO | 1995001751 A1 | 1/1995 |
| WO | 1996001599 A1 | 1/1996 |
| WO | 2001007583 A1 | 2/2001 |
| WO | 2003071140 A2 | 8/2003 |
| WO | 2006128068 A1 | 11/2006 |
| WO | 2007067628 A1 | 6/2007 |
| WO | 2007067937 A2 | 6/2007 |
| WO | 2007067938 A2 | 6/2007 |
| WO | 2007067939 A2 | 6/2007 |
| WO | 2007067940 A2 | 6/2007 |
| WO | 2007067941 A2 | 6/2007 |
| WO | 2007067943 A2 | 6/2007 |
| WO | 2007070361 A2 | 6/2007 |
| WO | 2008063195 A1 | 5/2008 |
| WO | 2009085457 A1 | 7/2009 |
| WO | 2009085458 A1 | 7/2009 |
| WO | 2009134876 A1 | 11/2009 |
| WO | 2010014480 A1 | 2/2010 |
| WO | 2010085773 A1 | 7/2010 |

(56) References Cited

FOREIGN PATENT DOCUMENTS

| | | |
|---|---|---|
| WO | 2010091701 A1 | 8/2010 |
| WO | 2010118387 A1 | 10/2010 |
| WO | 2010132472 A1 | 11/2010 |
| WO | 2010151277 A1 | 12/2010 |
| WO | 2011062653 A1 | 5/2011 |
| WO | 2011072221 A1 | 6/2011 |
| WO | 2012067682 A1 | 5/2012 |
| WO | 2012118659 A1 | 9/2012 |
| WO | 2012122517 A2 | 9/2012 |
| WO | 2012088149 A4 | 1/2013 |
| WO | 2014075415 A1 | 5/2014 |
| WO | 2014195933 A1 | 12/2014 |
| WO | 2015006480 A1 | 1/2015 |
| WO | 2015085162 A1 | 6/2015 |
| WO | 2015103574 A1 | 7/2015 |
| WO | 2015171921 A2 | 11/2015 |
| WO | 2015187430 A2 | 12/2015 |
| WO | 2015192018 A1 | 12/2015 |
| WO | 2015192027 A1 | 12/2015 |
| WO | 2016007851 A1 | 1/2016 |
| WO | 2016099774 A1 | 6/2016 |
| WO | 2016164930 A1 | 10/2016 |
| WO | 2016178697 A1 | 11/2016 |
| WO | 2016181315 A1 | 11/2016 |
| WO | 2016181316 A1 | 11/2016 |
| WO | 2016181317 A2 | 11/2016 |
| WO | 2016181318 A1 | 11/2016 |
| WO | 2016181320 A1 | 11/2016 |
| WO | 2016201264 A1 | 12/2016 |
| WO | 2017024056 A1 | 2/2017 |
| WO | 2017119934 A1 | 7/2017 |
| WO | 2017120169 A1 | 7/2017 |
| WO | 2017123981 A1 | 7/2017 |
| WO | 2017192477 A1 | 11/2017 |
| WO | 2017192480 A2 | 11/2017 |
| WO | 2017192495 A1 | 11/2017 |
| WO | 2017192510 A2 | 11/2017 |
| WO | 2017192542 A2 | 11/2017 |
| WO | 2017212257 A1 | 12/2017 |
| WO | 2018005511 A1 | 1/2018 |
| WO | 2018010659 A1 | 1/2018 |
| WO | 2018081323 A1 | 5/2018 |
| WO | 2018187856 A1 | 10/2018 |
| WO | 2018191149 A1 | 10/2018 |
| WO | 2018200800 A1 | 11/2018 |
| WO | 2018201037 A1 | 11/2018 |
| WO | 2018236754 A1 | 12/2018 |
| WO | 2019023280 A1 | 1/2019 |
| WO | 2019055512 A1 | 3/2019 |
| WO | 2019083982 A1 | 5/2019 |
| WO | 2019084442 A1 | 5/2019 |
| WO | 2019118436 A1 | 6/2019 |
| WO | 2019133606 A1 | 7/2019 |
| WO | 2019133608 A1 | 7/2019 |
| WO | 2019143960 A1 | 7/2019 |
| WO | 2019157359 A1 | 8/2019 |
| WO | 2019181612 A1 | 9/2019 |
| WO | 2019181634 | 9/2019 |
| WO | 2019181634 A1 | 9/2019 |
| WO | 2019185331 A1 | 10/2019 |
| WO | 2019212827 A1 | 11/2019 |
| WO | 2019217300 A1 | 11/2019 |
| WO | 2019217317 A1 | 11/2019 |
| WO | 2019217433 A1 | 11/2019 |
| WO | 2019226640 A1 | 11/2019 |
| WO | 2019232358 A1 | 12/2019 |
| WO | 2019234133 A1 | 12/2019 |
| WO | 2020026217 A1 | 2/2020 |
| WO | 2020057155 A1 | 3/2020 |
| WO | 2020061192 A1 | 3/2020 |
| WO | 2020072749 A1 | 4/2020 |
| WO | 2020131885 A1 | 6/2020 |
| WO | 2020206328 A1 | 10/2020 |
| WO | 2020252506 A1 | 12/2020 |
| WO | 2021113463 A1 | 6/2021 |
| WO | 2021150629 A1 | 7/2021 |
| WO | 2021216515 A1 | 10/2021 |
| WO | 2022007489 A1 | 1/2022 |
| WO | 2022007490 A1 | 1/2022 |
| WO | 2022020478 A1 | 1/2022 |
| WO | 2023280822 | 1/2023 |
| WO | 2023138275 | 7/2023 |
| WO | 2023196773 | 10/2023 |
| WO | 2023205899 | 11/2023 |
| WO | 2023236402 | 12/2023 |
| WO | 2023239966 | 12/2023 |
| WO | 2024007424 | 1/2024 |
| WO | 2024069495 | 4/2024 |
| WO | 2024086033 | 4/2024 |
| WO | 2024099406 | 5/2024 |
| WO | 2024110800 | 5/2024 |
| WO | 2024118748 | 6/2024 |
| WO | 2024127115 | 6/2024 |
| WO | 2024127133 | 6/2024 |
| WO | 2024211474 | 10/2024 |

OTHER PUBLICATIONS

N. M. Fried et al., "Laser ablation of the pulmonary veins by using a fiberoptic balloon catheter: Implications for treatment of paroxysmal atrial fibrillation", Lasers Surg. Med., roč. 28, č. 3, s. 197-203, 2001, doi: 10.1002/lsm.1038.

N. M. Fried, H. Calkins, a A. C. Lardo, "Linear lesions in myocardium created by Nd:YAG laser using diffusing optical fibers: In vitro and in vivo results", s. 10, 2000. 10 pages.

N. Sperelakis a T. Hoshiko, "Electrical Impedance of Cardiac Muscle", Circulation Research, roč. 9, č. 6, s. 1280-1283, lis. 1961, doi: 10.1161/01.RES.9.6.1280.

Na, et al., "Prediction of the braid pattern on arbitrary-shaped mandrels using the minimum path condition," Composites Science and Technology, 2013, 8 pages.

Neven Kars et al., "Acute and Long-Term Effects of Full-Power Electroporation Ablation Directly on the Porcine Esophagus", Circulation: Arrhythmia and Electrophysiology, roč. 10, č. 5, s. e004672, kvě. 2017, doi: 10.1161/CIRCEP.116.004672. 7 pages.

Neven Kars, van Driel Vincent, van Wessel Harry, van Es René, Doevendans Pieter A., a Wittkampf Fred, "Myocardial Lesion Size After Epicardial Electroporation Catheter Ablation After Subxiphoid Puncture", Circulation: Arrhythmia and Electrophysiology, roč. 7, č. 4, s. 728-733, srp. 2014, doi: 10.1161/CIRCEP.114.001659.

Notice of Allowance dated Oct. 17, 2023 for U.S. Appl. No. 18/345,897 (pp. 1-7).

O. N. Pakhomova, B. Gregory, I. Semenov, a A. G. Pakhomov, "Calcium-mediated pore expansion and cell death following nanoelectroporation", Biochimica et Biophysica Acta (BBA)—Biomembranes, roč. 1838, č. 10, s. 2547-2554, říj. 2014, doi: 10.1016/j.bbamem.2014.06.015.

O. Sten-Knudsen, "The ineffectiveness of the 'window field' in the initiation of muscle contraction", J Physiol, roč. 125, č. 2, s. 396-404, srp. 1954, doi: 10.1113/jphysiol.1954.sp005167.

O. Tovar a L. Tung, "Electroporation of Cardiac Cell Membranes with Monophasic or Biphasic Rectangular Pulses", Pacing Clin Electro, roč. 14, č. 11, s. 1887-1892, lis. 1991, doi: 10.1111/j.1540-8159.1991.tb02785.x.

Office Action (Non-Final Rejection) dated Feb. 16, 2023 for U.S. Appl. No. 17/931,975 (pp. 1-13).

Office Action (Notice of Allowance and Fees Due (PTOL-85)) dated Jun. 12, 2023 for U.S. Appl. No. 17/931,975 (pp. 1-7).

Office Action (Notice of Allowance and Fees Due (PTOL-85)) dated Oct. 3, 2023 for U.S. Appl. No. 18/184,757 (pp. 1-7).

Office Action dated Jul. 5, 2023 for U.S. Appl. No. 18/184,757 (pp. 1-7).

Office Action dated Sep. 1, 2023 for U.S. Appl. No. 18/345,897 (pp. 1-8).

P. A. J. Krijnen, R. Nijmeijer, C. J. L. M. Meijer, C. A. Visser, C. E. Hack, a H. W. M. Niessen, "Apoptosis in myocardial ischaemia and infarction", J Clin Pathol, roč. 55, č. 11, s. 801-811, lis. 2002, Viděno: 28. duben 2021. [Online]. Dostupné z: https://www.ncbi.nlm.nih.gov/pmc/articles/PMC1769793/.

(56) References Cited

OTHER PUBLICATIONS

P. Jaïs et al., "Prospective Randomized Comparison of Irrigated-Tip Versus Conventional-Tip Catheters for Ablation of Common Flutter", Circulation, roč. 101, č. 7, s. 772-776, úno. 2000, doi: 10.1161/01.CIR.101.7.772.

P. Loh et al., "Pulmonary Vein Isolation With Single Pulse Irreversible Electroporation: A First in Human Study in 10 Patients With Atrial Fibrillation", Circ: Arrhythmia and Electrophysiology, roč. 13, č. 10, říj. 2020, doi: 10.1161/CIRCEP.119.008192. 9 pages.

Q. Hu, R. P. Joshi, a K. H. Schoenbach, "Simulations of nanopore formation and phosphatidylserine externalization in lipid membranes subjected to a high-intensity, ultrashort electric pulse", Phys. Rev. E, roč. 72, č. 3, s. 031902, zář. 2005, doi: 10.1103/PhysRevE.72.031902. 10 pages.

R. Cardona-Guarache et al., "Thoracic Sympathectomy for Severe Refractory Multivessel Coronary Artery Spasm", The American Journal of Cardiology, roč. 117, č. 1, s. 159-161, led. 2016, doi: 10.1016/j.amjcard.2015.10.018.

R. E. Neal, P. A. Garcia, J. L. Robertson, a R. V. Davalos, "Experimental Characterization and Numerical Modeling of Tissue Electrical Conductivity during Pulsed Electric Fields for Irreversible Electroporation Treatment Planning", IEEE Trans. Biomed. Eng., roč. 59, č. 4, s. 1076-1085, dub. 2012, doi: 10.1109/TBME.2012.2182994.

R. G. Muthalaly et al., "Temporal trends in safety and complication rates of catheter ablation for atrial fibrillation", J Cardiovasc Electrophysiol, roč. 29, č. 6, s. 854-860, čer. 2018, doi: 10.1111/jce.13484.

R. Gupta a B. Rai, "Electroporation of Skin Stratum Corneum Lipid Bilayer and Molecular Mechanism of Drug Transport: A Molecular Dynamics Study", Langmuir, roč. 34, č. 20, s. 5860-5870, kvě. 2018, doi: 10.1021/acs.langmuir.8b00423.

R. Kato et al., "Pulmonary Vein Anatomy in Patients Undergoing Catheter Ablation of Atrial Fibrillation: Lessons Learned by Use of Magnetic Resonance Imaging", Circulation, roč. 107, č. 15, s. 2004-2010, dub. 2003, doi: 10.1161/01.CIR.0000061951.81767.4E.

R. Pavlovi, "Electro-Muscle Stimulation—The Application in Practice", s. 8, 2016.

R. Schilling et al., "Safety, effectiveness, and quality of life following pulmonary vein isolation with a multi-electrode radiofrequency balloon catheter in paroxysmal atrial fibrillation: 1-year outcomes from Shine", EP Europace, roč. 23, č. 6, s. 851-860, čer. 2021, doi: 10.1093/europace/euaa382.

R. Tung a K. A. Ellenbogen, "Emergence of Multielectrode Mapping: On the Road to Higher Resolution", Circ Arrhythm Electrophysiol, roč. 9, č. 6, čer. 2016, doi: 10.1161/CIRCEP.116.004281. 3 pages.

R. Van Es et al., "216-02: In vitro analysis of gas bubble formation and its effect on impedance during electroporation ablation", EP Europace, roč. 18, č. suppl_1, s. i141-i141, čer. 2016, doi: 10.1093/europace/18.suppl_1.i141c. Downloaded Feb. 2021.

R. van Es et al., "High-frequency irreversible electroporation for cardiac ablation using an asymmetrical waveform", BioMedical Engineering OnLine, roč. 18, č. 1, s. 75, čer. 2019, doi: 10.1186/s12938-019-0693-7.

R. van Es et al., "Novel method for electrode-tissue contact measurement with multi-electrode catheters", EP Europace, roč. 20, č. 1, s. 149-156, led. 2018, doi: 10.1093/europace/euw388.

R. W. Ariss et al., "Contemporary trends and in-hospital outcomes of catheter and stand-alone surgical ablation of atrial fibrillation", EP Europace, roč. 24, č. 2, s. 218-225, úno. 2022, doi: 10.1093/europace/euab198.

S. A. Kirsch a R. A. Böckmann, "Membrane pore formation in atomistic and coarse-grained simulations", Biochimica et Biophysica Acta (BBA)—Biomembranes, roč. 1858, č. 10, s. 2266-2277, říj. 2016, doi: 10.1016/j.bbamem.2015.12.031.

S. Bhonsle et al., "Characterization of Irreversible Electroporation Ablation with a Validated Perfused Organ Model", Journal of Vascular and Interventional Radiology, roč. 27, č. 12, s. 1913-1922.e2, pro. 2016, doi: 10.1016/j.jvir.2016.07.012.

S. Honarbakhsh et al., "PolarX Cryoballoon metrics predicting successful pulmonary vein isolation: targets for ablation of atrial fibrillation", EP Europace, s. euac100, čer. 2022, doi: 10.1093/europace/euac100. 10 pages.

S. Honarbakhsh et al., "Radiofrequency balloon catheter ablation for paroxysmal atrial fibrillation, Radiance Study—a UK experience", EP Europace, roč. 19, č. suppl_1, s. 121-i21, říj. 2017, doi: 10.1093/europace/eux283.004.

S. J. E. Rombouts et al., "Irreversible Electroporation of the Pancreas Using Parallel Plate Electrodes in a Porcine Model: A Feasibility Study", PLoS ONE, roč. 12, č. 1, s. e0169396, led. 2017. 13 pages.

S. M. Narayan a T. Baykaner, "Electroporation: The End of the Thermal Ablation Era ?•", Journal of the American College of Cardiology, roč. 74, č. 3, s. 327-329, čvc. 2019, doi: 10.1016/j.jacc.2019.06.013.

S. M. Singh et al., "Clinical outcomes after repair of left atrial esophageal fistulas occurring after atrial fibrillation ablation procedures", Heart Rhythm, roč. 10, č. 11, s. 1591-1597, lis. 2013, doi: 10.1016/j.hrthm.2013.08.012.

S. McBride et al., "Ablation Modalities for Therapeutic Intervention in Arrhythmia-Related Cardiovascular Disease: Focus on Electroporation", JCM, roč. 10, č. 12, s. 2657, čer. 2021, doi: 10.3390/jcm10122657.

S. Narayan a J. Zaman, "Mechanistically-based mapping of human cardiac fibrillation", The Journal of physiology, roč. 594, lis. 2015, doi: 10.1113/JP270513. 17 pages.

S. R. Dukkipati et al., "Pulmonary Vein Isolation Using the Visually Guided Laser Balloon", Journal of the American College of Cardiology, roč. 66, č. 12, s. 1350-1360, zář. 2015, doi: 10.1016/j.jacc.2015.07.036.

S. Tohoku et al., "Pulsed Field Ablation for Persistent Superior Vena Cava", JACC: Case Reports, roč. 4, č. 5, s. 301-305, bře. 2022, doi: 10.1016/j.jaccas.2022.01.015.

Shu Xiao, Siqi Guo, V. Nesin, R. Heller, a K. H. Schoenbach, "Subnanosecond Electric Pulses Cause Membrane Permeabilization and Cell Death", IEEE Trans. Biomed. Eng., roč. 58, č. 5, s. 1239-1245, kvě. 2011, doi: 10.1109/TBME.2011.2112360.

T. Batista Napotnik a D. Miklavi, "Pulse Duration Dependent Asymmetry in Molecular Transmembrane Transport Due to Electroporation in H9c2 Rat Cardiac Myoblast Cells In Vitro", Molecules, roč. 26, č. 21, Art. č. 21, led. 2021, doi: 10.3390/molecules26216571. 22 pages.

T. Batista Napotnik, T. Polajer, a D. Miklavčič, "Cell death due to electroporation—A review", Bioelectrochemistry, roč. 141, s. 107871, říj. 2021, doi: 10.1016/j.bioelechem.2021.107871. 18 pages.

T. D. Potter, L. Boersma, A. Babkin, M. Mazor, J. Cox, a S. Antonius, "Novel Linear Cryoablation Catheter to Treat Atrial Fibrillation", s. 1. Date unknown.

T. Harayama a H. Riezman, "Understanding the diversity of membrane lipid composition", Nat Rev Mol Cell Biol, roč. 19, č. 5, s. 281-296, kvě. 2018, doi: 10.1038/nrm.2017.138.

T. J. Buist et al., "Efficacy of multi-electrode linear irreversible electroporation", EP Europace, č. euaa280, lis. 2020, doi: 10.1093/europace/euaa280. 5 pages.

T. J. O'Brien et al., "Effects of internal electrode cooling on irreversible electroporation using a perfused organ model", International Journal of Hyperthermia, roč. 35, č. 1, s. 44-55, pro. 2018, doi: 10.1080/02656736.2018.1473893.

J. S. Koruth et al., "Endocardial ventricular pulsed field ablation: a proof-of-concept preclinical evaluation", EP Europace, roč. 22, č. 3, s. 434-439, bře. 2020, doi: 10.1093/europace/euz341.

J. S. Koruth et al., "Feasibility, safety, and durability of porcine atrial ablation using a lattice-tip temperature-controlled radiofrequency ablation catheter", J Cardiovasc Electrophysiol, roč. 31, č. 6, s. 1323-1331, čer. 2020, doi: 10.1111/jce.14473.

J. S. Koruth et al., "Focal Pulsed Field Ablation for Pulmonary Vein Isolation and Linear Atrial Lesions: A Preclinical Assessment of Safety and Durability", Circ: Arrhythmia and Electrophysiology, roč. 13, č. 6, s. e008716, čer. 2020, doi: 10.1161/CIRCEP.120.008716. 15 pages.

J. S. Koruth et al., "Pulsed Field Ablation Versus Radiofrequency Ablation: Esophageal Injury in a Novel Porcine Model", Circ:

(56) References Cited

OTHER PUBLICATIONS

Arrhythmia and Electrophysiology, roč. 13, č. 3, bře. 2020, doi: 10.1161/CIRCEP.119.008303. 10 pages.

J. S. Koruth, I. Kawamura, S. R. Dukkipati, W. Whang, M. Turagam, a V. Y. Reddy, "B-AB06-03 Preclinical Assessment of the Feasibility, Safety and Lesion Durability of a Novel "Single-Shot" Pulse Field Ablation Catheter for Pulmonary Vein Isolation", Heart Rhythm, roč. 18, č. 8, s. S10-S11, srp. 2021, doi: 10.1016/j.hrthm.2021.06.038.

J. Song, R. P. Joshi, a K. H. Schoenbach, "Synergistic effects of local temperature enhancements on cellular responses in the context of high-intensity, ultrashort electric pulses", Med Biol Eng Comput, roč. 49, č. 6, s. 713-718, čer. 2011, doi: 10.1007/s11517-011-0745-z.

J.-L. Lin et al., "Electrophysiological Mapping and Histological Examinations of the Swine Atrium with Sustained (≥24 h) Atrial Fibrillation: A Suitable Animal Model for Studying Human Atrial Fibrillation", CRD, roč. 99, č. 2, s. 78-84, 2003, doi: 10.1159/000069728.

K. C. K. Wong et al., "High incidence of acute sub-clinical circumflex artery 'injury' following mitral isthmus ablation", European Heart Journal, roč. 32, č. 15, s. 1881-1890, srp. 2011, doi: 10.1093/eurheartj/ehr117.

K. H. Schoenbach, R. Joshi, J. Kolb, S. Buescher, a S. Beebe, "Subcellular effects of nanosecond electrical pulses", in The 26th Annual International Conference of the IEEE Engineering in Medicine and Biology Society, San Francisco, CA, USA, 2004, roč. 4, s. 5447-5450. doi: 10.1109/IEMBS.2004.1404522.

K. Kuroki et al., "Ostial dimensional changes after pulmonary vein isolation: Pulsed field ablation vs radiofrequency ablation", Heart Rhythm, roč. 17, č. 9, s. 1528-1535, zář. 2020, doi: 10.1016/j.hrthm.2020.04.040.

K. P. Charpentier, F. Wolf, L. Noble, B. Winn, M. Resnick, a D. E. Dupuy, "Irreversible electroporation of the liver and liver hilum in swine", HPB, roč. 13, č. 3, s. 168-173, bře. 2011, doi: 10.1111/j.1477-2574.2010.00261.x.

K. R. Thomson et al., "Investigation of the Safety of Irreversible Electroporation in Humans", Journal of Vascular and Interventional Radiology, roč. 22, č. 5, s. 611-621, kvě. 2011, doi: 10.1016/j.jvir.2010.12.014.

K. Schultheis et al., "Delineating the Cellular Mechanisms Associated with Skin Electroporation", Hum Gene Ther Methods, roč. 29, č. 4, s. 177-188, srp. 2018, doi: 10.1089/hgtb.2017.105.

K. Yokoyama et al., "Canine Model of Esophageal Injury and Atrial-Esophageal Fistula After Applications of Forward-Firing High-Intensity Focused Ultrasound and Side-Firing Unfocused Ultrasound in the Left Atrium and Inside the Pulmonary Vein", Circ Arrhythm Electrophysiol, roč. 2, č. 1, s. 41-49, úno. 2009, doi: 10.1161/CIRCEP.108.807925.

Kelkar, "Resistance and Laser Welding for Medical Devices," Medical Device and Diagnostics Industry (MDDI), Jun. 2006, 14 pages.

Koruth Jacob et al., "Preclinical Evaluation of Pulsed Field Ablation", Circulation: Arrhythmia and Electrophysiology, roč. 12, č. 12, s. e007781, pro. 2019, doi: 10.1161/CIRCEP.119.007781. 9 pages.

L. F. Cima a L. M. Mir, "Macroscopic characterization of cell electroporation in biological tissue based on electrical measurements", s. 4, 2014.

L. Galluzzi et al., "Essential versus accessory aspects of cell death: recommendations of the NCCD 2015", Cell Death Differ, roč. 22, č. 1, s. 58-73, led. 2015, doi: 10.1038/cdd.2014.137.

L. Schomel, S. Eyerly, a Partick Wolf, "Visualization of Convective Heat Transfer with a Thermal Camera in vivo during Cardiac Radiofrequency Ablation", 2014, doi: 10.13140/RG.2.1.3723.6088. 1 page.

L. V. Chernomordik et al., "The electrical breakdown of cell and lipid membranes: the similarity of phenomenologies", Biochimica et Biophysica Acta (BBA)—Biomembranes, roč. 902, č. 3, s. 360-373, zář. 1987, doi: 10.1016/0005-2736(87)90204-5.

L. V. Saint-Quentin, "Cryterion Cryoablation System FIM/CE Mark sttudy", s. 73, 2019.

L.-B. Shi, O. Rossvoll, P. Tande, P. Schuster, E. Solheim, a J. Chen, "Cryoballoon vs. radiofrequency catheter ablation: insights from Norwegian randomized study of PERSistent Atrial Fibrillation (NO-PERSAF study)", EP Europace, roč. 24, č. 2, s. 226-233, úno. 2022, doi: 10.1093/europace/euab281.

Lababidi, "Designing an Intravascular Diagnostic Catheter", Tufts University, 2013. 97 pages.

M. A. Pinkert, R. A. Hortensius, B. M. Ogle, a K. W. Eliceiri, "Imaging the Cardiac Extracellular Matrix", in Cardiac Extracellular Matrix, roč. 1098, E. G. Schmuck, P. Hematti, a A. N. Raval, Ed. Cham: Springer International Publishing, 2018, s. 21-44. doi: 10.1007/978-3-319-97421-7_2.

M. B. Sano et al., "Reduction of Muscle Contractions during Irreversible Electroporation Therapy Using High-Frequency Bursts of Alternating Polarity Pulses: A Laboratory Investigation in an Ex Vivo Swine Model", Journal of Vascular and Interventional Radiology, roč. 29, č. 6, s. 893-898.e4, čer. 2018, doi: 10.1016/j.jvir.2017.12.019.

M. B. Sano, "Production of Spherical Ablations Using Nonthermal Irreversible Electroporation_ A Laboratory Investigation Using a Single Electrode and Grounding Pad", s. 12. 2016.

M. B. Sano, M. R. DeWitt, S. D. Teeter, a L. Xing, "Optimization of a single insertion electrode array for the creation of clinically relevant ablations using high-frequency irreversible electroporation", Computers in Biology and Medicine, roč. 95, s. 107-117, dub. 2018, doi: 10.1016/j.compbiomed.2018.02.009.

M. Das et al., "Local catheter impedance drop during pulmonary vein isolation predicts acute conduction block in patients with paroxysmal atrial fibrillation: initial results of the Localize clinical trial", EP Europace, roč. 23, č. 7, s. 1042-1051, čvc. 2021, doi: 10.1093/europace/euab004.

M. et al Reichel, "Computer Simulation of Field Distribution and Excitation of Denervated Muscle Fibers Caused by Surface Electrodes", Artif Organs, roč. 23, č. 5, s. 4, 1999.

M. F. Lorenzo, S. P. Bhonsle, C. B. Arena, a R. V. Davalos, "Rapid Impedance Spectroscopy for Monitoring Tissue Impedance, Temperature, and Treatment Outcome During Electroporation-Based Therapies", IEEE Trans. Biomed. Eng., roč. 68, č. 5, s. 1536-1546, kvě. 2021, doi: 10.1109/TBME.2020.3036535.

M. Faroja et al., "Irreversible Electroporation Ablation: Is All the Damage Nonthermal?", Radiology, roč. 266, č. 2, s. 462-470, úno. 2013, doi: 10.1148/radiol.12120609.

M. Grimaldi et al., "Time Course of Irreversible Electroporation Lesion Development Through Short- and Long-Term Follow-Up in Pulsed-Field Ablation-Treated Hearts", Circ: Arrhythmia and Electrophysiology, s. 10.1161/CIRCEP.121.010661, čer. 2022, doi: 10.1161/CIRCEP.121.010661. 8 pages.

M. H. A. Groen et al., "In vivo analysis of the origin and characteristics of gaseous microemboli during catheter-mediated irreversible electroporation", EP Europace, roč. 23, č. 1, s. 139-146, led. 2021, doi: 10.1093/europace/euaa243.

M. H. Ruwald, A. Johannessen, M. L. Hansen, R. Worck, a J. Hansen, "Pulsed field ablation of the cavotricuspid isthmus using a multispline-electrode pulsed field ablation catheter", HeartRhythm Case Reports, roč. 8, č. 3, s. 147-150, bře. 2022, doi: 10.1016/j.hrcr.2021.12.009.

M. Haïssaguerre et al., "Spontaneous Initiation of Atrial Fibrillation by Ectopic Beats Originating in the Pulmonary Veins", N Engl J Med, roč. 339, č. 10, s. 659-666, zář. 1998, doi: 10.1056/NEJM199809033391003.

M. Hwang, J. Kim, B. Lim, J.-S. Song, B. Joung, a E. Shim, "Multiple factors influence the morphology of the bipolar electrogram: An in silico modeling study", PLoS Computational Biology, roč. 15, dub. 2019, doi: 10.1371/journal.pcbi.1006765. 13 pages.

M. Pavlin, T. Kotnik, D. Miklavčič, P. Kramar, a A. Maček Lebar, "Chapter Seven Electroporation of Planar Lipid Bilayers and Membranes", in Advances in Planar Lipid Bilayers and Liposomes, roč. 6, Elsevier, 2008, s. 165-226. doi: 10.1016/S1554-4516(07)06007-3.

M. Pešl, "Epicardial delivery of diversified pulsed field potentials in animal model", 2019, roč. 2019. Viděno: 28. duben 2021. [Online]. 2 pages. Dostupné z: https://www.vutbr.cz/en/rad/results/detail?vav_id=157796#vysledek-157796.

(56) References Cited

OTHER PUBLICATIONS

M. Phillips, E. Maor, a B. Rubinsky, "Nonthermal Irreversible Electroporation for Tissue Decellularization", Journal of Biomechanical Engineering, roč. 132, č. 9, s. 091003, zář. 2010, 8 pages, doi: 10.1115/1.4001882.

M. R. Meijerink, H. J. Scheffer, a G. Narayanan, Ed., Irreversible Electroporation in Clinical Practice. Cham: Springer International Publishing, 2018. doi: 10.1007/978-3-319-55113-5. 281 pages.

M. Rehman, A. Adiyaman, J. Smit, B. Manfai, a A. Elvan, "Comparison of safety and efficacy between POLARx and Arctic Front cryoballoon ablation", EP Europace, roč. 24, č. Supplement_1, s. euac053.110, kvě. 2022, doi: 10.1093/europace/euac053.110. 1 page.

M. Rienks, A.-P. Papageorgiou, N. G. Frangogiannis, a S. Heymans, "Myocardial Extracellular Matrix: An Ever-Changing and Diverse Entity", Circ Res, roč. 114, č. 5, s. 872-888, úno. 2014, doi: 10.1161/CIRCRESAHA.114.302533.

M. S. Arruda et al., "A Novel Mesh Electrode Catheter for Mapping and Radiofrequency Delivery at the Left Atrium-Pulmonary Vein Junction: A Single-Catheter Approach to Pulmonary Vein Antrum Isolation", J Cardiovasc Electrophysiol, roč. 18, č. 2, s. 206-211, úno. 2007, doi: 10.1111/j.1540-8167.2007.00720.x.

M. T. Stewart et al., "Intracardiac pulsed field ablation: Proof of feasibility in a chronic porcine model", Heart Rhythm, roč. 16, č. 5, s. 754-764, kvě. 2019, doi: 10.1016/j.hrthm.2018.10.030.

M. T. Stewart et al., "Safety and chronic lesion characterization of pulsed field ablation in a Porcine model", J Cardiovasc Electrophysiol, roč. 32, č. 4, s. 958-969, dub. 2021, doi: 10.1111/jce.14980.

M. Tsivian a T. J. Polascik, "Bilateral focal ablation of prostate tissue using low-energy direct current (LEDC): a preclinical canine study", BJU International, roč. 112, č. 4, s. 526-530, 2013, doi: 10.1111/bju.12227.

M. Yacoub a R. C. Sheppard, "Cryoballoon Pulmonary Vein Catheter Ablation of Atrial Fibrillation", in StatPearls, Treasure Island (FL): StatPearls Publishing, 2021. 10 pages. Viděno: 28. duben 2021. [Online]. Dostupné z: http://www.ncbi.nlm.nih.gov/books/NBK534804/.

Melenka, et al. "Manufacturing Processes for Braided Composite Materials," Handbook of Advances in Braided Composite Materials, 2017, 107 pages.

MWS Wire Industries, "Medical Microwire", 2019, 28 pages.

N. G. dela Paz a P. A. D'Amore, "Arterial versus venous endothelial cells", Cell Tissue Res, roč. 335, č. 1, s. 5-16, led. 2009, doi: 10.1007/s00441-008-0706-5.

A. Anic et al., "Acute safety, efficacy, and advantages of a novel cryoballoon ablation system for pulmonary vein isolation in patients with paroxysmal atrial fibrillation: initial clinical experience", EP Europace, roč. 23, č. 8, s. 1237- 1243, srp. 2021, doi: 10.1093/europace/euab018.

A. E. Sowers a M. R. Lieber, "Electropore diameters, lifetimes, numbers, and locations in individual erythrocyte ghosts", FEBS Letters, roč. 205, č. 2, s. 179-184, zář. 1986, doi: 10.1016/0014-5793(86)80893-6.

A. G. Pakhomov, J. F. Kolb, J. A. White, R. P. Joshi, S. Xiao, a K. H. Schoenbach, "Long-lasting plasma membrane permeabilization in mammalian cells by nanosecond pulsed electric field (nsPEF)", Bioelectromagnetics, roč. 28, č. 8, s. 655-663, pro. 2007, doi: 10.1002/bem.20354.

A. G. Pakhomov, S. Grigoryev, I. Semenov, M. Casciola, C. Jiang, a S. Xiao, "The second phase of bipolar, nanosecond-range electric pulses determines the electroporation efficiency", Bioelectrochemistry, roč. 122, s. 123-133, srp. 2018, doi: 10.1016/j.bioelechem.2018.03.014.

A. Golberg a B. Rubinsky, "Towards Electroporation Based Treatment Planning considering Electric Field Induced Muscle Contractions", Technol Cancer Res Treat, roč. 11, č. 2, s. 189-201, dub. 2012, doi: 10.7785/tcrt.2012.500249.

A. Hai a M. E. Spira, "On-chip electroporation, membrane repair dynamics and transient in-cell recordings by arrays of gold mushroom-shaped microelectrodes", Lab Chip, roč. 12, č. 16, s. 2865, 2012, doi: 10.1039/c2lc40091j. 9 pages.

A. Ivorra a B. Rubinsky, "In vivo electrical impedance measurements during and after electroporation of rat liver", Bioelectrochemistry, roč. 70, č. 2, s. 287-295, kvě. 2007, doi: 10.1016/j.bioelechem.2006.10.005.

A. Meissner et al., "Impact of irrigated energy application on the right coronary artery hemodynamics: FFR measurement in patients who underwent ablation of common type atrial flutter", J Interv Card Electrophysiol, roč. 21, č. 1, s. 35-42, led. 2008, doi: 10.1007/s10840-007-9188-8.

A. Sugrue et al., "Irreversible electroporation for catheter-based cardiac ablation: a systematic review of the preclinical experience", J Interv Card Electrophysiol, roč. 55, č. 3, s. 251-265, zář. 2019, doi: 10.1007/s10840-019-00574-3.

A. Sugrue et al., "Irreversible electroporation for the treatment of cardiac arrhythmias", Expert Review of Cardiovascular Therapy, roč. 16, č. 5, s. 349-360, kvě. 2018, doi: 10.1080/14779072.2018.1459185.

A. T. Feldman a D. Wolfe, "Tissue Processing and Hematoxylin and Eosin Staining", in Histopathology, roč. 1180, C. E. Day, Ed. New York, NY: Springer New York, 2014, s. 31-43. doi: 10.1007/978-1-4939-1050-2_3.

A. Valiūnienė, I. Gabriunaite, M. Poderyte, a A. Ramanavicius, "Electroporation of a hybrid bilayer membrane by scanning electrochemical microscope", Bioelectrochemistry, roč. 136, s. 107617, pro. 2020, doi: 10.1016/j.bioelechem.2020.107617.7 pages.

A. Verma et al., "First-in-Human Experience and Acute Procedural Outcomes Using a Novel Pulsed Field Ablation System: The Pulsed AF Pilot Trial", Circ: Arrhythmia and Electrophysiology, roč. 15, č. 1, s. e010168, led. 2022, doi: 10.1161/CIRCEP.121.010168. 10 pages.

A. Vižintin, J. Vidmar, J. Ščančar, a D. Miklavčič, "Effect of interphase and interpulse delay in high-frequency irreversible electroporation pulses on cell survival, membrane permeabilization and electrode material release", Bioelectrochemistry, roč. 134, s. 107523, srp. 2020, doi: 10.1016/j.bioelechem.2020.107523. 14 pages.

A. Wojtaszczyk, G. Caluori, M. Pešl, K. Melajova, a Z. Stárek, "Irreversible electroporation ablation for atrial fibrillation", J Cardiovasc Electrophysiol, roč. 29, č. 4, s. 643-651, dub. 2018, doi: 10.1111/jce.13454.

B. C. du Pré et al., "Minimal coronary artery damage by myocardial electroporation ablation", EP Europace, roč. 15, č. 1, s. 144-149, led. 2013, doi: 10.1093/europace/eus171.

B. Howard et al., "Characterization of Phrenic Nerve Response to Pulsed Field Ablation", Circ: Arrhythmia and Electrophysiology, roč. 15, č. 6, er. 2022, doi: 10.1161/CIRCEP.121.010127. 9 pages.

B. K. Martinez et al., "Systematic review and meta-analysis of catheter ablation of ventricular tachycardia in ischemic heart disease", Heart Rhythm, roč. 17, č. 1, s. e206-e219, led. 2020, doi: 10.1016/j.hrthm.2019.04.024.

B. López-Alonso, H. Sarnago, Ó. Lucía, P. Briz, a J. M. Burdío, "Real-Time Impedance Monitoring During Electroporation Processes in Vegetal Tissue Using a High-Performance Generator", Sensors, roč. 20, č. 11, s. 3158, čer. 2020, doi: 10.3390/s20113158. 14 pages.

B. Mercadal, C. B. Arena, R. V. Davalos, a A. Ivorra, "Avoiding nerve stimulation in irreversible electroporation: a numerical modeling study", Phys Med Biol, roč. 62, č. 20, s. 8060-8079, říj. 2017, doi: 10.1088/1361-6560/aa8c53.

B. Mercadal, N. Beitel-White, K. N. Aycock, Q. Castellví, R. V. Davalos, a A. Ivorra, "Dynamics of Cell Death After Conventional IRE and H-FIRE Treatments", Ann Biomed Eng, roč. 48, č. 5, s. 1451-1462, kvě. 2020, doi: 10.1007/s10439-020-02462-8.

B. Rubinsky, G. Onik, a P. Mikus, "Irreversible electroporation: a new ablation modality—clinical implications", Technol Cancer Res Treat, roč. 6, č. 1, s. 37-48, úno. 2007, doi: 10.1177/153303460700600106.

B. Schmidt, S. Chen, S. Tohoku, S. Bordignon, F. Bologna, a K. R. J. Chun, "Single shot electroporation of premature ventricular contractions from the right ventricular outflow tract", EP Europace, roč. 24, č. 4, s. 597-597, dub. 2022, doi: 10.1093/europace/euab212.

Biosense Webster, "Study Protocol Shine 2018". 2018. [Online]. Dostupné z: https://clinicaltrials.gov/ProvidedDocs/33/NCT03437733/Prot_000.pdf. 86 pages.

(56) References Cited

OTHER PUBLICATIONS

Boyle, et al. "Laser Source Selection for Micro-welding Processes", Amada Miyachi Europe, 2015, 28 pages.

C. B. Arena et al., "High-frequency irreversible electroporation (H-FIRE) for non-thermal ablation without muscle contraction", BioMed Eng OnLine, roč. 10, č. 1, s. 102, pro. 2011, doi: 10.1186/1475-925X-10-102. 21 pages.

C. B. Arena, M. B. Sano, M. N. Rylander, a R. V. Davalos, "Theoretical Considerations of Tissue Electroporation With High-Frequency Bipolar Pulses", IEEE Trans. Biomed. Eng., roč. 58, č. 5, s. 1474-1482, kvě. 2011, doi: 10.1109/TBME.2010.2102021.

C. Lyu, J. Wang, M. Powell-Palm, a B. Rubinsky, "Simultaneous electroporation and dielectrophoresis in non-electrolytic micro/nano-electroporation", Sci Rep, roč. 8, č. 1, s. 2481, pro. 2018, doi: 10.1038/s41598-018-20535-6. 13 pages.

C. M. Tschabrunn, S. Roujol, N. C. Dorman, R. Nezafat, M. E. Josephson, a E. Anter, "High-Resolution Mapping of Ventricular Scar: Comparison between Single and Multi-Electrode Catheters", Circ Arrhythm Electrophysiol, roč. 9, č. 6, čer. 2016, doi: 10.1161/CIRCEP.115.003841. 22 pages.

C. M. Witt et al., "Intrapulmonary Vein Ablation Without Stenosis: A Novel Balloon-Based Direct Current Electroporation Approach", JAHA, roč. 7, č. 14, čvc. 2018, doi: 10.1161/JAHA.118.009575. 8 pages.

C. V. DeSimone, "Novel balloon catheter device with pacing, ablating, electroporation, and drug-eluting capabilities for atrial fibrillation treatment-preliminary efficacy and safety studies in a canine model", Translational Research, roč. 164, č. 6, s. 7, 2014. 7 pages.

C. Valdez, M. B. Jirjis, C. C. Roth, R. A. Barnes, a B. L. Ibey, "Nanosecond electric pulses modulate skeletal muscle calcium dynamics and contraction", prezentováno v SPIE BIOS, San Francisco, California, United States, úno. 2017, s. 100660X. doi: 10.1117/12.2253693. 9 pages.

C. Yao et al., "Bipolar Microsecond Pulses and Insulated Needle Electrodes for Reducing Muscle Contractions During Irreversible Electroporation", IEEE transactions on bio-medical engineering, roč. PP, dub. 2017, doi: 10.1109/TBME.2017.2690624. 15 pages.

Carey, et al., "Design of Braided Composite Cardiovascular Catheters Based on Required Axial, Flexural, and Torsional Rigidities", Wiley InterScience, 2004, 9 pages.

D. C. Sweeney a M. Reber, "Quantification of cell membrane permeability induced by monopolar and high-frequency bipolar bursts of electrical pulses", Biochimica et Biophysica Acta, s. 10, 1858. 2016, 10 pages.

D. E. Haines et al., "Microembolism and catheter ablation I: a comparison of irrigated radiofrequency and multielectrode-phased radiofrequency catheter ablation of pulmonary vein ostia", Circ Arrhythm Electrophysiol, roč. 6, č. 1, s. 16-22, úno. 2013, doi: 10.1161/CIRCEP.111.973453.

D. E. Haines, A. R. Strunk, A. Novichenok, N. Kirchhof, a M. Stewart, "The Biophysics of Passive Convective Cooling During Catheter Ablation with Gold versus Platinum Electrodes and Multielectrode Phased Radiofrequency Energy Delivery: Gold versus Platinum Ablation Electrodes", J Cardiovasc Electrophysiol, roč. 26, č. 11, s. 1257-1261, lis. 2015, doi: 10.1111/jce.12752.

D. J. Wilber et al., "Comparison of Antiarrhythmic Drug Therapy and Radiofrequency Catheter Ablation in Patients With Paroxysmal Atrial Fibrillation: A Randomized Controlled Trial", JAMA, roč. 303, č. 4, s. 333, led. 2010, doi: 10.1001/jama.2009.2029. 8 pages.

D. L. Packer et al., "Cryoballoon Ablation of Pulmonary Veins for Paroxysmal Atrial Fibrillation", Journal of the American College of Cardiology, roč. 61, č. 16, s. 1713-1723, dub. 2013, doi: 10.1016/j.jacc.2012.11.064.

D. L. Packer et al., "Effect of Catheter Ablation vs Antiarrhythmic Drug Therapy on Mortality, Stroke, Bleeding, and Cardiac Arrest Among Patients With Atrial Fibrillation: The Cabana Randomized Clinical Trial", JAMA, roč. 321, č. 13, s. 1261, dub. 2019, doi: 10.1001/jama.2019.0693. 14 pages.

D. Miklavc, "A validated model of in vivo electric eld distribution in tissues for electrochemotherapy and for DNA electrotransfer for gene therapy", Biochimica et Biophysica Acta, s. 11. 2000. 11 pages.

D. Miklavčič et al., "The effect of high frequency electric pulses on muscle contractions and antitumor efficiency in vivo for a potential use in clinical electrochemotherapy", Bioelectrochemistry, roč. 65, č. 2, s. 121-128, úno. 2005, doi: 10.1016/j.bioelechem.2004.07.004.

D. Miklavčič, Ed., Handbook of Electroporation. Cham: Springer International Publishing, 2017. doi: 10.1007/978-3-319-32886-7. 2956 pages.

D. R. Tomlinson a J. Mandrola, "Pulsed Field Ablation for Persistent Atrial Fibrillation (PersAFOne)", Journal of the American College of Cardiology, roč. 76, č. 9, s. 1081-1083, zář. 2020, doi: 10.1016/j.jacc.2020.07.032.

D. W. Hunter, G. Kostecki, J. M. Fish, J. A. Jensen, a H. Tandri, "In Vitro Cell Selectivity of Reversible and Irreversible: Electroporation in Cardiac Tissue", Circ: Arrhythmia and Electrophysiology, roč. 14, č. 4, dub. 2021, doi: 10.1161/CIRCEP.120.008817. 9 pages.

D. W. Hunter, H. Tandri, H. Halperin, L. Tung, a R. D. Berger, "Tetanizing prepulse: A novel strategy to mitigate implantable cardioverter-defibrillator shock-related pain", Heart Rhythm, roč. 13, č. 5, s. 1142-1148, kvě. 2016, doi: 10.1016/j.hrthm.2015.12.047.

Dukkipati Srinivas R. et al., "Visual Balloon-Guided Point-by-Point Ablation", Circulation: Arrhythmia and Electrophysiology, roč. 3, č. 3, s. 266-273, čer. 2010, doi: 10.1161/CIRCEP.109.933283.

E. Guenther, N. Klein, P. Mikus, M. K. Stehling, a B. Rubinsky, "Electrical breakdown in tissue electroporation", Biochemical and Biophysical Research Communications, roč. 467, č. 4, s. 736-741, lis. 2015, doi: 10.1016/j.bbrc.2015.10.072.

E. Maor, "Pulsed electric fields for cardiac ablation and beyond: A state of the art review", s. 30, 2018.

E. P. Gerstenfeld a J. Michele, "Pulmonary vein isolation using a compliant endoscopic laser balloon ablation system in a swine model", J Interv Card Electrophysiol, roč. 29, č. 1, s. 1-9, říj. 2010, doi: 10.1007/s10840-010-9501-9.

T. J. O'Brien et al., "Experimental High-Frequency Irreversible Electroporation Using a Single-Needle Delivery Approach for Nonthermal Pancreatic Ablation In Vivo", Journal of Vascular and Interventional Radiology, roč. 30, č. 6, s. 854-862.e7, čer. 2019, doi: 10.1016/j.jvir.2019.01.032.

T. Kotnik, L. Rems, M. Tarek, a D. Miklavčič, "Membrane Electroporation and Electropermeabilization: Mechanisms and Models", Annu. Rev. Biophys., roč. 48, č. 1, s. 63-91, kvř. 2019, doi: 10.1146/annurev-biophys-052118-115451.

T. Kurita, "Coronary Artery Spasms and ST-Segment Elevation During Catheter Ablation of Pulmonary Vein Isolation—Cause, Mechanism, and Management—", Circ J, roč. 85, č. 3, s. 272-274, úno. 2021, doi: 10.1253/circj.CJ-20-1238.

T. Nakamura et al., "Incidence and Characteristics of Coronary Artery Spasms Related to Atrial Fibrillation Ablation Procedures—Large-Scale Multicenter Analysis—", Circ J, roč. 85, č. 3, s. 264-271, úno. 2021, doi: 10.1253/circj.CJ-20-1096.

T. Saitoh et al., "Coronary Hyperreactivity to Adrenergic Stimulation and Increased Nocturnal Vagal Tone Trigger Coronary Vasospasm", Jpn Circ J, roč. 62, č. 10, s. 721-726, 1998, doi: 10.1253/jcj.62.721.

T. Zhu et al., "Pulsed Field Ablation of Superior Vena Cava: Feasibility and Safety of Pulsed Field Ablation", Frontiers in Cardiovascular Medicine, roč. 8, 2021, Viděno: 3. březen 2022. [Online]. Dostupné z: https://www.frontiersin.org/article/10.3389/fcvm.2021.698716.

V. J. H. M. van Driel et al., "Pulmonary Vein Stenosis After Catheter Ablation: Electroporation Versus Radiofrequency", Circ Arrhythm Electrophysiol, roč. 7, č. 4, s. 734-738, srp. 2014, doi: 10.1161/CIRCEP.113.001111.

V. J. H. M. van Driel, K. Neven, H. van Wessel, A. Vink, P. A. F. M. Doevendans, a F. H. M. Wittkampf, "Low vulnerability of the right phrenic nerve to electroporation ablation", Heart Rhythm, roč. 12, č. 8, s. 1838-1844, srp. 2015, doi: 10.1016/j.hrthm.2015.05.012.

V. Novickij et al., "High-Pulsed Electromagnetic Field Generator for Contactless Permeabilization of Cells In Vitro", IEEE Trans. Magn., roč. 56, č. 5, s. 1-6, kvě. 2020, doi: 10.1109/TMAG.2020.2979120.

(56) References Cited

OTHER PUBLICATIONS

V. P. Nikolski a I. R. Efimov, "Electroporation of the heart", EP Europace, roč. 7, č. s2, s. S146-S154, led. 2005, doi: 10.1016/j.eupc.2005.04.011.
V. Puczok, "Zdroj vysokonapěťových pulzů pro elektroporaci buněk", 2016. 75 pages.
V. van Driel, "Electroporation ablation: a new ablation modality for the ablation of arrhythmogenic cardiac substrate", s. 235, 2016.
V. Viswam, M. E. J. Obien, F. Franke, U. Frey, a A. Hierlemann, "Optimal Electrode Size for Multi-Scale Extracellular-Potential Recording From Neuronal Assemblies", Front. Neurosci., roč. 13, 2019, doi: 10.3389/fnins.2019.00385. 23 pages.
V. Y. Reddy et al., "Ablation of Atrial Fibrillation With Pulsed Electric Fields: An Ultra-Rapid, Tissue-Selective Modality for Cardiac Ablation", JACC: Clinical Electrophysiology, roč. 4, č. 8, s. 987-995, srp. 2018, doi: 10.1016/j.jacep.2018.04.005.
V. Y. Reddy et al., "Lattice-Tip Focal Ablation Catheter That Toggles Between Radiofrequency and Pulsed Field Energy to Treat Atrial Fibrillation: A First-in-Human Trial", Circ: Arrhythmia and Electrophysiology, roč. 13, č. 6, čer. 2020, doi: 10.1161/CIRCEP.120.008718. 13 pages.
V. Y. Reddy et al., "Pulsed Field Ablation for Pulmonary Vein Isolation in Atrial Fibrillation", Journal of the American College of Cardiology, roč. 74, č. 3, s. 315-326, čvc. 2019, doi: 10.1016/j.jacc.2019.04.021.
V. Y. Reddy et al., "Pulsed Field Ablation in Patients With Persistent Atrial Fibrillation", Journal of the American College of Cardiology, roč. 76, č. 9, s. 1068-1080, zář. 2020, doi: 10.1016/j.jacc.2020.07.007.
V. Y. Reddy et al., "Pulsed Field Ablation of Paroxysmal Atrial Fibrillation", JACC: Clinical Electrophysiology, roč. 7, č. 5, s. 614-627, kvě. 2021, doi: 10.1016/j.jacep.2021.02.014.
V. Y. Reddy et al., "Visually-Guided Balloon Catheter Ablation of Atrial Fibrillation: Experimental Feasibility and First-in-Human Multicenter Clinical Outcome", Circulation, roč. 120, č. 1, s. 12-20, čvc. 2009, doi: 10.1161/CIRCULATIONAHA.108.840587.
W. B. Han, S. J. Kim, H. H. An, H.-S. Kim, Y. Kim, a C. S. Yoon, "Molecular dynamics simulation of interlayer water embedded in phospholipid bilayer", Materials Science and Engineering: C, roč. 36, s. 49-56, bře. 2014, doi: 10.1016/j.msec.2013.11.033.
W. Krassowska a P. D. Filev, "Modeling Electroporation in a Single Cell", Biophysical Journal, roč. 92, č. 2, s. 404-417, led. 2007, doi: 10.1529/biophysj.106.094235.
W. R. Rogers et al., "Strength-Duration Curve for an Electrically Excitable Tissue Extended Down to Near 1 Nanosecond", IEEE Trans. Plasma Sci., roč. 32, č. 4, s. 1587-1599, srp. 2004, doi: 10.1109/TPS.2004.831758.
W. Szlasa et al., "Oxidative Effects during Irreversible Electroporation of Melanoma Cells—In Vitro Study", Molecules, roč. 26, č. 1, s. 154, pro. 2020, doi: 10.3390/molecules26010154.
W. van den Bos et al., "Thermal Energy during Irreversible Electroporation and the Influence of Different Ablation Parameters", Journal of Vascular and Interventional Radiology, roč. 27, č. 3, s. 433-443, bře. 2016, doi: 10.1016/j.jvir.2015.10.020.
W. Yang et al., "Differential Sensitivities of Malignant and Normal Skin Cells to Nanosecond Pulsed Electric Fields", Technol Cancer Res Treat, roč. 10, č. 3, s. 281-286, čer. 2011, doi: 10.7785/tcrt.2012.500204.
Y. Granot, A. Ivorra, E. Maor, a B. Rubinsky, "In vivo imaging of irreversible electroporation by means of electrical impedance tomography", Phys. Med. Biol., roč. 54, č. 16, s. 4927-4943, srp. 2009, doi: 10.1088/0031-9155/54/16/006.
Y. Lv, C. Yao, a B. Rubinsky, "A Conceivable Mechanism Responsible for the Synergy of High and Low Voltage Irreversible Electroporation Pulses", Ann Biomed Eng, roč. 47, č. 7, s. 1552-1563, čvc. 2019, doi: 10.1007/s10439-019-02258-5.
Y. Lv, Y. Zhang, a B. Rubinsky, "Molecular and histological study on the effects of electrolytic electroporation on the liver", Bioelectrochemistry, roč. 125, s. 79-89, úno. 2019, doi: 10.1016/j.bioelechem.2018.09.007.
Y. Nakatani et al., "Pulsed field ablation prevents chronic atrial fibrotic changes and restrictive mechanics after catheter ablation for atrial fibrillation", EP Europace, č. euab155, čvc. 2021, doi: 10.1093/europace/euab155. 10 pages.
Y. Salazar, R. Bragos, a J. Rosell, "Transcatheter measurement of myocardium electrical impedance: 2 versus 3 electrode method", in Proceedings of the 25th Annual International Conference of the IEEE Engineering in Medicine and Biology Society (IEEE Cat. No.03CH37439), Cancun, Mexico, 2003, s. 3102-3105. doi: 10.1109/IEMBS.2003.1280798.
Yanes, et al., "Consistent Repeatability in Tube Welding for Balloon Catheter Manufacturing", http://beta.rodpub.com/uploads/BalloonCatheterWelding_WhitePaper.pdf, 2014, retrieved May 8, 2023.
Yavin Hagai et al., "A Circular Multielectrode Pulsed-Field Ablation Catheter, Lasso PFA: Lesion Characteristics, Durability and Effect on Neighboring Structures", Circulation: Arrhythmia and Electrophysiology, roč. 0, č. 0, 2018, doi: 10.1161/CIRCEP.120.009229. 9 pages.
Z. Szabó et al., "Real-time intraoperative visualization of myocardial circulation using augmented reality temperature display", Int J Cardiovasc Imaging, roč. 29, č. 2, s. 521-528, úno. 2013, doi: 10.1007/s10554-012-0094-5.
E. P. Gerstenfeld, "Catheter Ablation of Atrial Fibrillation Using Electroporation", JACC: Clinical Electrophysiology, roč. 4, č. 8, s. 996-998, srp. 2018, doi: 10.1016/j.jacep.2018.05.020.
E. W. Lee, C. Chen, V. E. Prieto, S. M. Dry, C. T. Loh, a S. T. Kee, "Advanced Hepatic Ablation Technique for Creating Complete Cell Death: Irreversible Electroporation", Radiology, roč. 255, č. 2, s. 426-433, kvě. 2010, doi: 10.1148/radiol.10090337.
F. Alejandro Gómez, L. E. Ballesteros, L. Stella Cortés, F. Alejandro Gómez, L. E. Ballesteros, a L. Stella Cortés, "Morphological description of great cardiac vein in pigs compared to human hearts", Brazilian Journal of Cardiovascular Surgery, roč. 30, č. 1, s. 63-69, úno. 2015, doi: 10.5935/1678-9741.20140101.
F. Argus, B. Boyd, a S. M. Becker, "Electroporation of tissue and cells: A three-equation model of drug delivery", Computers in Biology and Medicine, roč. 84, s. 226-234, kvě. 2017, doi: 10.1016/j.compbiomed.2017.04.001.
F. Bourier et al., "High-power short-duration versus standard radiofrequency ablation: Insights on lesion metrics", J Cardiovasc Electrophysiol, roč. 29, č. 11, s. 1570-1575, lis. 2018, doi: 10.1111/jce.13724.
F. Bourier, "In-silico analysis of the relation between conventional and high-power short-duration RF ablation settings and resulting lesion metrics", J Cardiovasc Electrophysiol, dub. 2020. 23 pages.
F. D. Ramirez, V. Y. Reddy, R. Viswanathan, M. Hocini, a P. Jaïs, "Emerging Technologies for Pulmonary Vein Isolation", Circ Res, roč. 127, č. 1, s. 170-183, čer. 2020, doi: 10.1161/CIRCRESAHA.120.316402.
F. H. M. Wittkampf et al., "Myocardial Lesion Depth With Circular Electroporation Ablation", Circ Arrhythm Electrophysiol, roč. 5, č. 3, s. 581-586, čer. 2012, doi: 10.1161/CIRCEP.111.970079.
F. H. M. Wittkampf, R. van Es, a K. Neven, "Electroporation and its Relevance for Cardiac Catheter Ablation", JACC: Clinical Electrophysiology, roč. 4, č. 8, s. 977-986, srp. 2018, doi: 10.1016/j.jacep.2018.06.005.
F. H. Wittkampf et al., "Feasibility of Electroporation for the Creation of Pulmonary Vein Ostial Lesions", Journal of Cardiovascular Electrophysiology, roč. 22, č. 3, s. 302-309, bře. 2011, doi: 10.1111/j.1540-8167.2010.01863.x.
F. Ren et al., "Electrical and thermal analyses of catheter-based irreversible electroporation of digestive tract", International Journal of Hyperthermia, roč. 36, č. 1, s. 853-866, led. 2019, doi: 10.1080/02656736.2019.1646928.
Farapulse, "Pefcat II , CIP". 2019 . . . [Online]. 70 pages. Dostupné z: https://clinicaltrials.gov/ProvidedDocs/08/NCT04170608/Prot_SAP_000.pdf.
Farapulse, "The Impulse Study: A Safety and Feasibility Study of the Farapulse Endocardial Ablation System to Treat Atrial Fibrillation—Protocol No. CS0188, Revision D". 2019. 66 pages.

(56) References Cited

OTHER PUBLICATIONS

FDA, "SSED P030031B BSW NaviStar/Celsius Thermocool". 2004. Viděno: 28. duben 2021. 22 pages. [Online]. Dostupné z: https://www.accessdata.fda.gov/cdrh_docs/pdf3/P030031B.pdf.
G. C. Ganzenmüller, S. Hiermaier, a M. O. Steinhauser, "Shockwave induced damage in lipid bilayers: a dissipative particle dynamics simulation study", Soft Matter, roč. 7, č. 9, s. 4307, 2011, doi: 10.1039/c0sm01296c.
G. Caluori et al., "AC Pulsed Field Ablation Is Feasible and Safe in Atrial and Ventricular Settings: A Proof-of-Concept Chronic Animal Study", Front Bioeng Biotechnol, roč. 8, pro. 2020, doi: 10.3389/fbioe.2020.552357. 14 pages.
G. Long et al., "Histological and Finite Element Analysis of Cell Death due to Irreversible Electroporation", Technol Cancer Res Treat, roč. 13, č. 6, s. 561-569, pro. 2014, doi: 10.7785/tcrtexpress.2013.600253.
G. Long, P. K. Shires, D. Plescia, S. J. Beebe, J. F. Kolb, a K. H. Schoenbach, "Targeted Tissue Ablation With Nanosecond Pulses", IEEE Trans. Biomed. Eng., roč. 58, č. 8, s. 2161-2167, srp. 2011, doi: 10.1109/TBME.2011.2113183.
G. O. Hartzler, L. V. GiorgiD, A. M. Diehl, a W. R. Hamaker, "Right coronary spasm complicating electrode catheter ablation of a right lateral accessory pathway", Journal of the American College of Cardiology, roč. 6, č. 1, s. 250-253, čvc. 1985, doi: 10.1016/S0735-1097(85)80285-0.
G. Onik, P. Mikus, a B. Rubinsky, "Irreversible electroporation: implications for prostate ablation", Technol Cancer Res Treat, roč. 6, č. 4, s. 295-300, srp. 2007, doi: 10.1177/153303460700600405.
G. P. Tolstykh, "Activation of intracellular phosphoinositide signaling after a single 600 nanosecond electric pulse", s. 7, 2013.
G. R. Meininger et al., "Initial Experience with a Novel Focused Ultrasound Ablation System for Ring Ablation Outside the Pulmonary Vein", s. 8, 2003.
G. S. Munavalli et al., "Safety and Efficacy of Nanosecond Pulsed Electric Field Treatment of Sebaceous Gland Hyperplasia", Dermatol Surg, roč. 46, č. 6, s. 803-809, čer. 2020, doi: 10.1097/DSS.0000000000002154.
Granot et al., In vivo imaging of irreversible electroporation by measn of EIT, s. 18., 2009.
H. Cochet et al., "Pulsed field ablation selectively spares the oesophagus during pulmonary vein isolation for atrial fibrillation", EP Europace, č. euab090, kvě. 2021, doi: 10.1093/europace/euab090. 9 pages.
H. D. Yavin, K. Higuchi, J. Sroubek, A. Younis, I. Zilberman, a E. Anter, "Pulsed-Field Ablation in Ventricular Myocardium Using a Focal Catheter", Circulation: Arrhythmia and Electrophysiology, roč. 14, č. 9, s. e010375, zář. 2021, doi: 10.1161/CIRCEP.121.010375. 10 pages.
H. Hayashi et al., "Left atrial wall thickness and outcomes of catheter ablation for atrial fibrillation in patients with hypertrophic cardiomyopathy", J Interv Card Electrophysiol, roč. 40, č. 2, s. 153-160, srp. 2014, doi: 10.1007/s10840-014-9894-y.
H. J. Phillips, "Dye Exclusion Tests for Cell Viability", in Tissue Culture, Elsevier, 1973, s. 406-408. doi: 10.1016/B978-0-12-427150-0.50101-7.
H. Kottkamp et al., "Global multielectrode contact-mapping plus ablation with a single catheter in patients with atrial fibrillation: Global AF study", J Cardiovasc Electrophysiol, roč. 30, č. 11, s. 2248-2255, lis. 2019, doi: 10.1111/jce.14172.
H. Kottkamp, F. Moser, A. Rieger, D. Schreiber, C. Ponisch, a M. Trofin, "Global multielectrode contact mapping plus ablation with a single catheter: Preclinical and preliminary experience in humans with atrial fibrillation: Kottkamp et al.", J Cardiovasc Electrophysiol, roč. 28, č. 11, s. 1247-1256, lis. 2017, doi: 10.1111/jce.13310.
H. Lehrmann et al., "Near-Fatal Coronary Artery Spasm During Cryoballoon Pulmonary Vein Isolation: An Unreported Complication", Circ: Arrhythmia and Electrophysiology, roč. 7, č. 6, s. 1273-1274, pro. 2014, doi: 10.1161/CIRCEP.114.001788.
H. Mori et al., "The influence of the electrodes spacing of a mapping catheter on the atrial voltage substrate map", Journal of Cardiology, roč. 72, č. 5, s. 434-442, lis. 2018, doi: 10.1016/j.jjcc.2018.04.012.
H. T. Tien a A. Ottova, "The Bilayer Lipid Membrane ž BLM/Under Electrical Fields", roč. 10, č. 5, s. 11, 2003.
H. Yavin et al., "Circular Multielectrode Pulsed Field Ablation Catheter Lasso Pulsed Field Ablation", Circulation: Arrhythmia and Electrophysiology, roč. 14, č. 2, s. e009229, úno. 2021, doi: 10.1161/CIRCEP.120.009229. 9 pages.
H. Yavin et al., "Pulsed Field Ablation Using a Lattice Electrode for Focal Energy Delivery: Biophysical Characterization, Lesion Durability, and Safety Evaluation", Circ: Arrhythmia and Electrophysiology, roč. 13, č. 6, s. e008580, čer. 2020, doi: 10.1161/CIRCEP.120.008580. 10 pages.
HCL Technologies, "An Overview of the Plastic Material Selection Process for Medical Devices," 2013, 26 pages.
Hoffman, et al., "Radiopacity assessment fo neurovascular implants," Current Directions in Biomedical Engineering, 2 (1) 533-536, 2016.
Howard Brian et al., "Reduction in Pulmonary Vein Stenosis and Collateral Damage With Pulsed Field Ablation Compared With Radiofrequency Ablation in a Canine Model", Circulation: Arrhythmia and Electrophysiology, roč. 13, č. 9, s. e008337, zář. 2020, doi: 10.1161/CIRCEP.120.008337.
I. Kaminska et al., "Electroporation-induced changes in normal immature rat myoblasts (H9C2)", gpb, roč. 31, č. 01, s. 19-25, 2012, doi: 10.4149/gpb_2012_003.
I. Kawamura et al., "Does pulsed field ablation regress over time? A quantitative temporal analysis of pulmonary vein isolation", Heart Rhythm, s. S154752712100182X, úno. 2021, doi: 10.1016/j.hrthm.2021.02.020.
I. Kawamura et al., "How does the level of pulmonary venous isolation compare between pulsed field ablation and thermal energy ablation (radiofrequency, cryo, or laser)?", EP Europace, č. euab150, čer. 2021, doi: 10.1093/europace/euab150. 10 pages.
J. A. Berkenbrock, G. Brasil Pintarelli, A. de Castro Antônio Júnior, a D. O. H. Suzuki, "Verification of Electroporation Models Using the Potato Tuber as In Vitro Simulation", J. Med. Biol. Eng., roč. 39, č. 2, s. 224-229, dub. 2019, doi: 10.1007/s40846-018-0408-8.
J. D. Kaufman et al., "High-Frequency Irreversible Electroporation Using 5,000-V Waveforms to Create Reproducible 2- and 4-cm Ablation Zones—A Laboratory Investigation Using Mechanically Perfused Liver", Journal of Vascular and Interventional Radiology, roč. 31, č. 1, s. 162-168.e7, led. 2020, doi: 10.1016/j.jvir.2019.05.009.
J. Dermol-Černe, T. Batista Napotnik, M. Reberšek, a D. Miklavčič, "Short microsecond pulses achieve homogeneous electroporation of elongated biological cells irrespective of their orientation in electric field", Sci Rep, roč. 10, č. 1, s. 9149, pro. 2020, doi: 10.1038/s41598-020-65830-3.
J. F. Edd, "In vivo results of a new focal tissue ablation technique irreversible electroporation.pdf", IEEE Transactions on Biomedical Engineering, roč. 2006, 2006. 7 pages.
J. F. Edd, L. Horowitz, R. V. Davalos, L. M. Mir, a B. Rubinsky, "In Vivo Results of a New Focal Tissue Ablation Technique: Irreversible Electroporation", IEEE Trans. Biomed. Eng., roč. 53, č. 7, s. 1409-1415, čvc. 2006, doi: 10.1109/TBME.2006.873745.
J. G. Skeate, D. M. Da Silva, E. Chavez-Juan, S. Anand, R. Nuccitelli, a W. M. Kast, "Nano-Pulse Stimulation induces immunogenic cell death in human papillomavirus-transformed tumors and initiates an adaptive immune response", PLoS One, roč. 13, č. 1, s. e0191311, led. 2018, doi: 10.1371/journal.pone.0191311. 17 pages.
J. Gehl, T. Skovsgaard, a L. M. Mir, "Vascular reactions to in vivo electroporation: characterization and consequences for drug and gene delivery", Biochimica et Biophysica Acta (BBA)—General Subjects, roč. 1569, č. 1-3, s. 51-58, led. 2002, doi: 10.1016/S0304-4165(01)00233-1.
J. Hughes a G. Gobe, "Identification and quantification of apoptosis in the kidney using morphology, biochemical and molecular markers", Nephrology, roč. 12, č. 5, s. 452-458, 2007, doi: https://doi.org/10.1111/j.1440-1797.2007.00854.x.

(56) References Cited

OTHER PUBLICATIONS

J. M. Lee et al., "Characterization of irreversible electroporation on the stomach: A feasibility study in rats", Sci Rep, roč. 9, č. 1, s. 9094, pro. 2019, doi: 10.1038/s41598-019-45659-1.

* cited by examiner

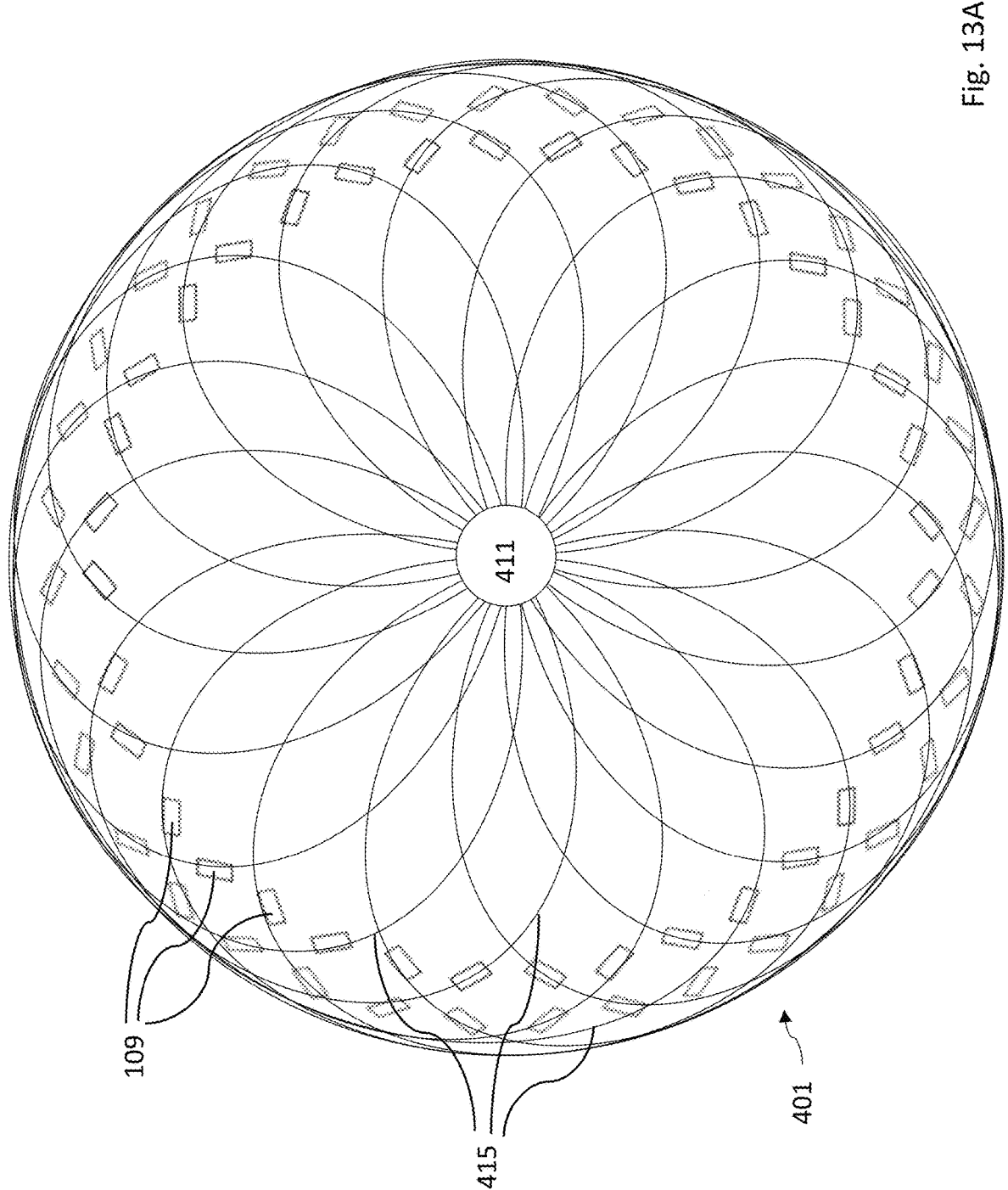

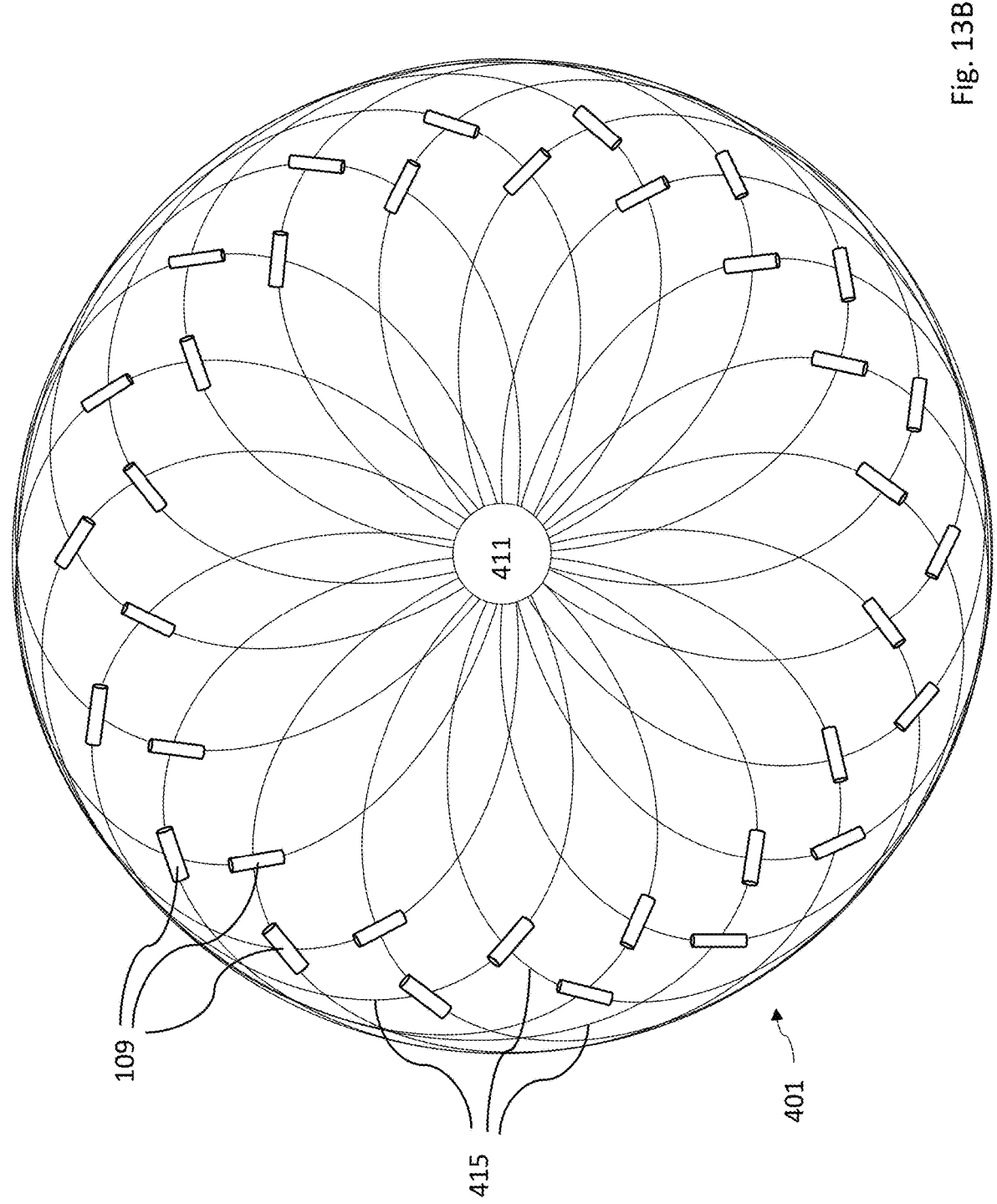

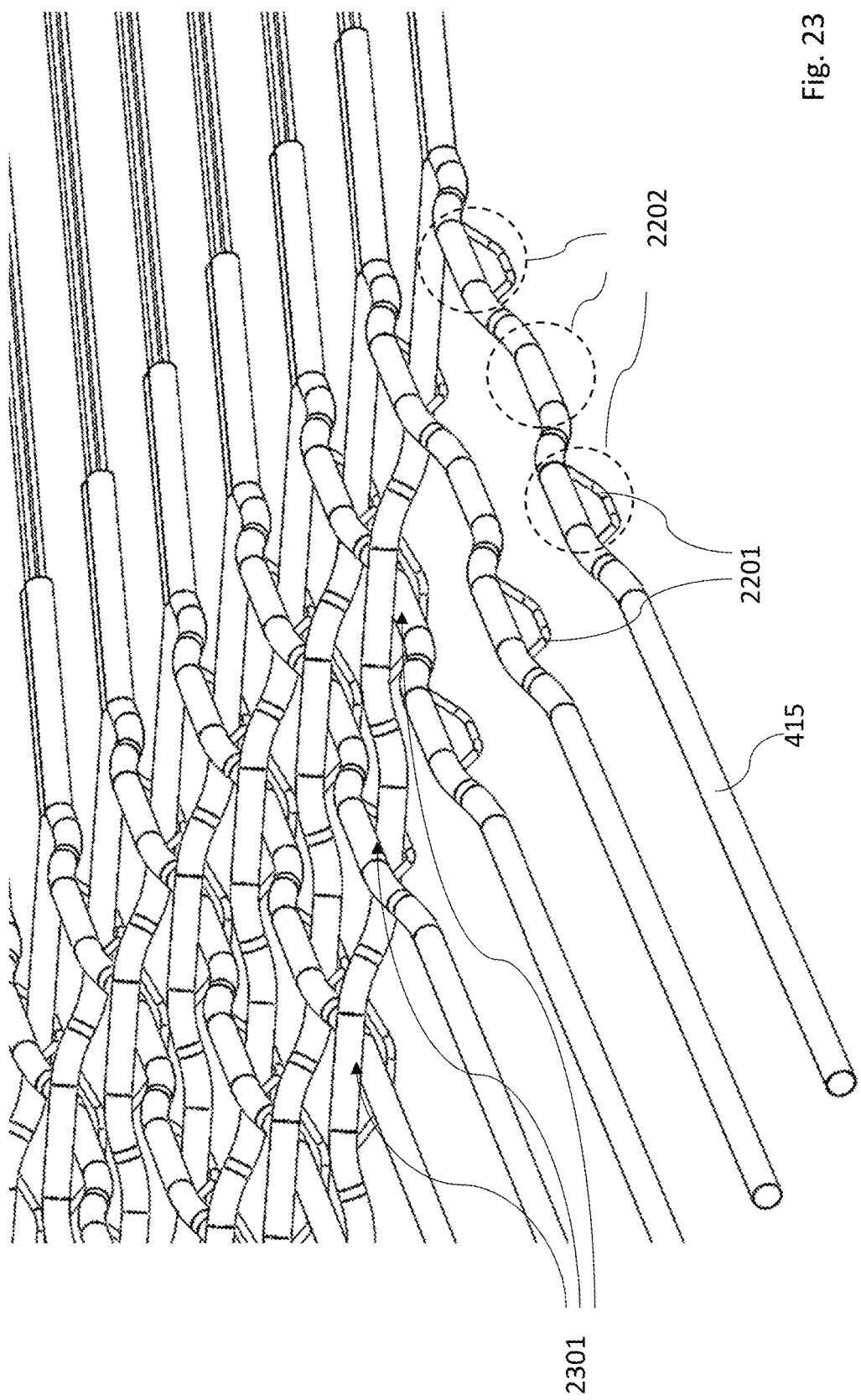

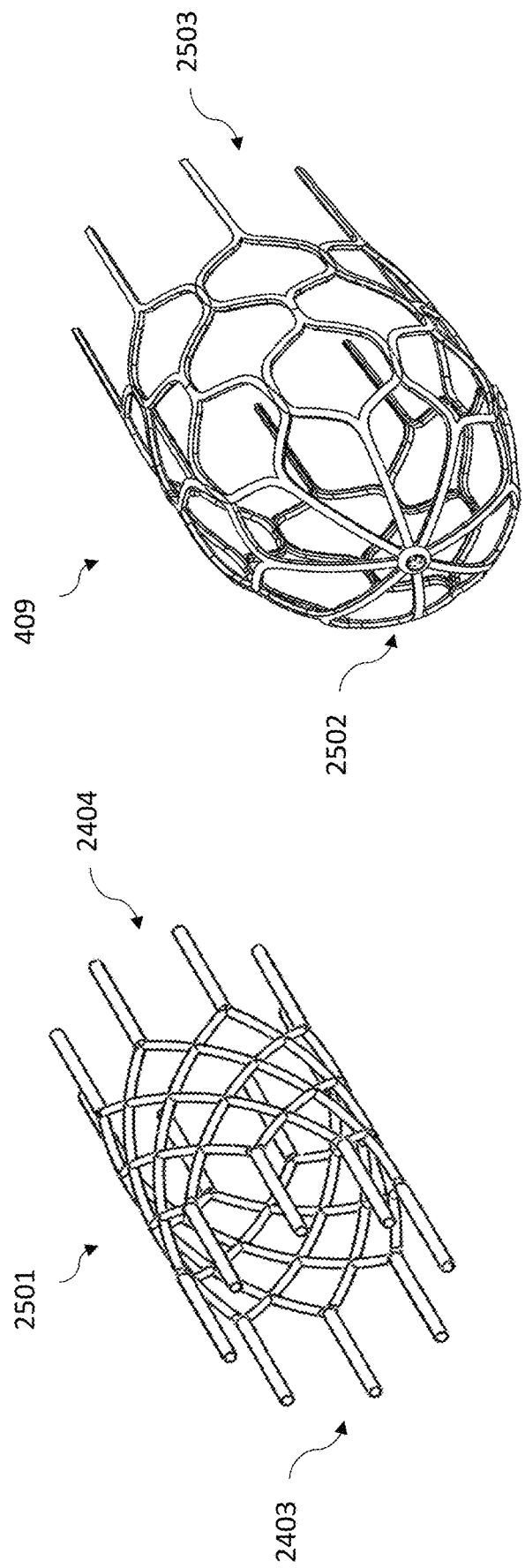

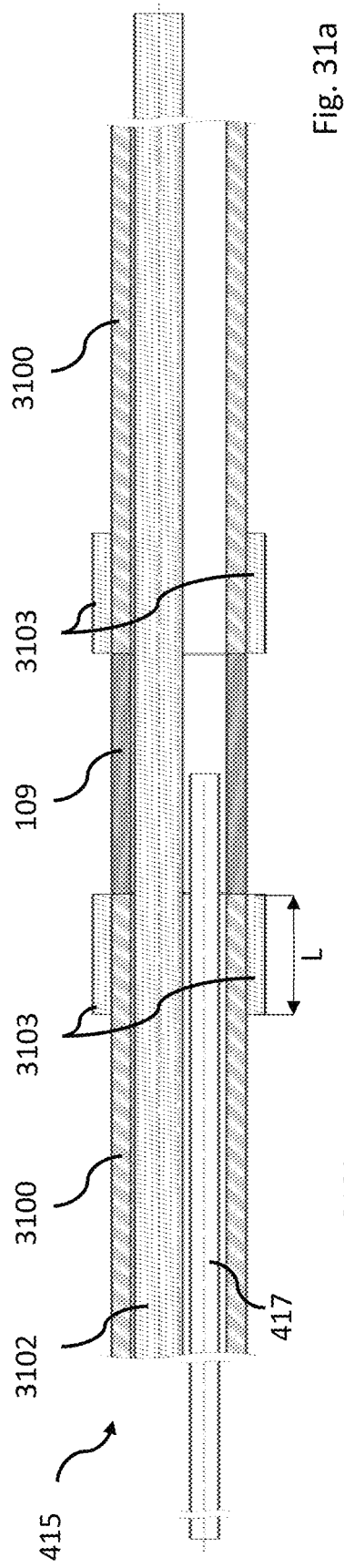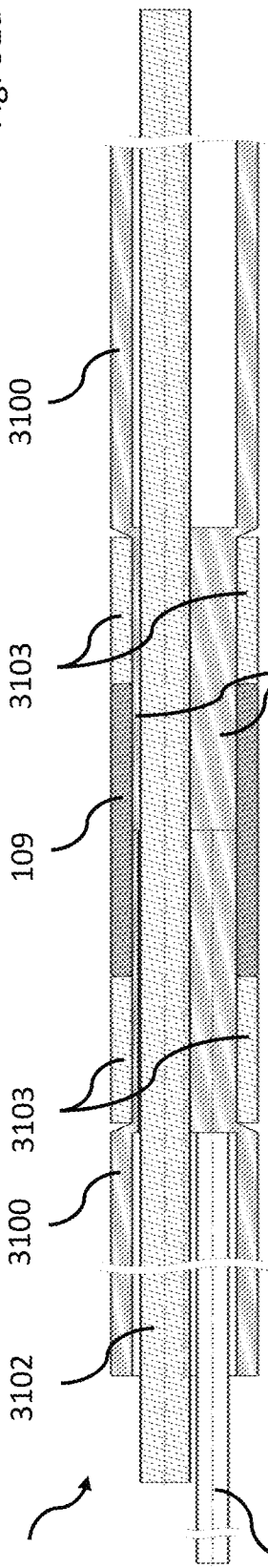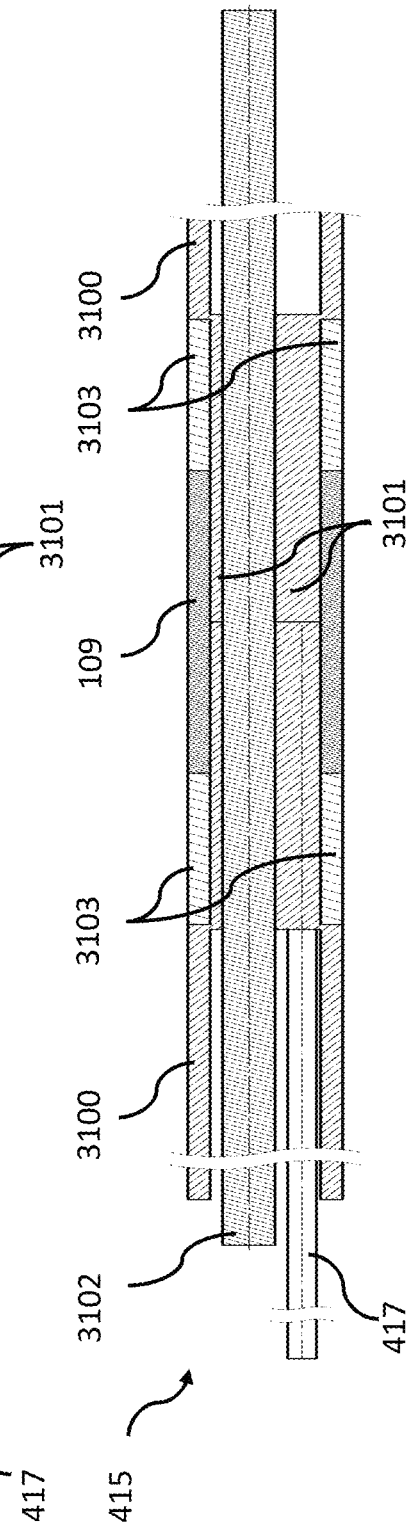

PULSED FIELD ABLATION DEVICE AND METHOD

CROSS-REFERENCE TO RELATED APPLICATIONS

This application is a continuation of U.S. patent application Ser. No. 18/422,443, filed on Jan. 25, 2024, which is a continuation of International Application No. PCT/IB2023/059957, filed on Oct. 4, 2023, which claims priority to U.S. Provisional Patent Application No. 63/378,405, filed on Oct. 5, 2022, all of which are incorporated herein by reference in their entirety.

FIELD OF THE INVENTION

This invention relates to ablation devices and methods, specifically devices and methods of pulsed field ablation of a target tissue by pulsed electric fields where one of the main principles of the ablation may be an irreversible electroporation of cell membranes.

Background of the Invention

Atrial fibrillation is the most common persistent cardiac arrhythmia, affecting 10% of the population over 60 years of age. In addition to pharmacological treatment, the established therapy to improve the symptoms of the disease and reduce mortality is so-called catheter ablation.

Catheter ablation involves subcutaneously advancing one or more flexible catheters into the patient's blood vessels, in the case of a heart ablation usually either in a femoral vein, an internal jugular vein, or a subclavian vein. The catheters are then advanced towards the target treatment site in or on the heart.

The primary means of ablation therapy of cardiac arrhythmias is to eliminate the pro-arrhythmogenic substrate directly by destroying it or to prevent the spread of non-physiological action potential by linear or circular isolation. Both of these approaches basically require the formation of a lesion through which the action potential of the myocardium does not spread. By applying energy, a small part of the myocardium is locally destroyed and is transformed into non-myocardial connective tissue by natural physiological processes within several weeks.

Common methods of ablation known from the prior art are based on thermal destruction of the tissue either by high or by low temperatures. Such methods include for example heating a target tissue by radiofrequency field (RF) or laser, or freezing the tissue by cryoablation. Those methods cause necrosis of the target tissue, which can add risk to the procedure.

Recently, methods and devices using electric fields for ablation have been utilized. The goal of these methods is to cause tissue destruction by inducing an irreversible electroporation of cell membranes instead of destruction by high or low temperatures, and so reduce the disadvantages and risks of ablation procedures based mainly on thermal damage, however there are still drawbacks that need to be solved.

Common designs of such devices may be a catheter with a distal tip with one or more electrodes. The catheter can have for example one active electrode on the tip. An indifferent electrode can be placed for example on the skin of a patient. Ablation of the target treatment site with such a device has to be done point by point, which increases the duration and complexity of the procedure.

Another example of a prior device is a catheter with electrodes placed in a row on a distal tip of a single catheter body. The distal tip of such catheter is delivered close to the target treatment site and deployed (bent) into a specific shape near the target treatment site. With such a shape, more than one electrode can be used for the therapy and less movement with the distal tip is needed, but the deployment of the catheter into the right shape, proper positioning and further manipulation with such a catheter can be very difficult. An indifferent electrode can be placed on the skin of the patient as well or the ablation can be carried out in bipolar fashion between particular electrodes placed on the distal end of the catheter.

Devices with catheter terminal baskets comprising single struts with electrodes are known as well from the prior art. Such a device may assure easier deployment and positioning against the target site. Because there are usually more electrodes placed on the catheter terminal, the ablation can be again either monopolar with an indifferent electrode, for example placed on the skin of the patient, or bipolar between particular electrodes on the catheter terminal. One disadvantage of this solution is limited struts, which means a limited number of electrodes creating a specific circular pattern in space. This disadvantage is caused by a need for mechanical stability of the particular struts to be able to keep a stable shape of the basket. This means to be rigid enough, the struts need to keep particular dimensions. The number of struts used is then limited by the size of the catheter. Another disadvantage of this solution is such a construction cannot fully assure a mutual distance of the struts in the deployed configuration, which means the distance between electrodes cannot be assured as well. That means the device may need to be repositioned multiple times in order to ensure proper ablation, which prolongs the duration of the procedure.

The quality and safety of the ablation needs to be increased on one hand, while risks for patients and duration of therapy need to be reduced on the other hand. There is thus a need for improved devices and methods of ablation, which would be more gentle and safer for the patient, with reduced complexity and with enhanced quality and reliability of the method and device itself.

SUMMARY OF THE INVENTION

Disclosed herein is a device and method of an ablation system, in particular an ablation method and device for pulsed field ablation by electric fields according to the description, which can address and solve the above-mentioned problems, and which would be more gentle and safer for the patient, with reduced time and technical complexity and with enhanced quality, efficacy and reliability of the system, method and device itself.

BRIEF DESCRIPTION OF THE DRAWINGS

An exemplary aspect of the present disclosure is illustrated by way of example in the accompanying drawings in which like reference numbers indicate the same or similar elements and in which:

FIG. 13A is an example of a spatial pattern of electrodes on a distal tip of a catheter.

FIG. 13B is another example of a spatial pattern of electrodes on a distal tip of a catheter.

FIG. 23 is a view of an example of a partially braided mesh comprising filaments made by a molding process.

FIG. 25a is a view of an example of a molded mesh molded as a three-dimensional structure.

FIG. 25b is a view of an example of a molded expandable basket.

FIG. 31a shows a cross section of a filament in a manufacturing step.

FIG. 31b shows a cross section of a filament in another manufacturing step.

FIG. 31c shows another cross section of a filament in another manufacturing step.

DETAILED DESCRIPTION

Figure 1:
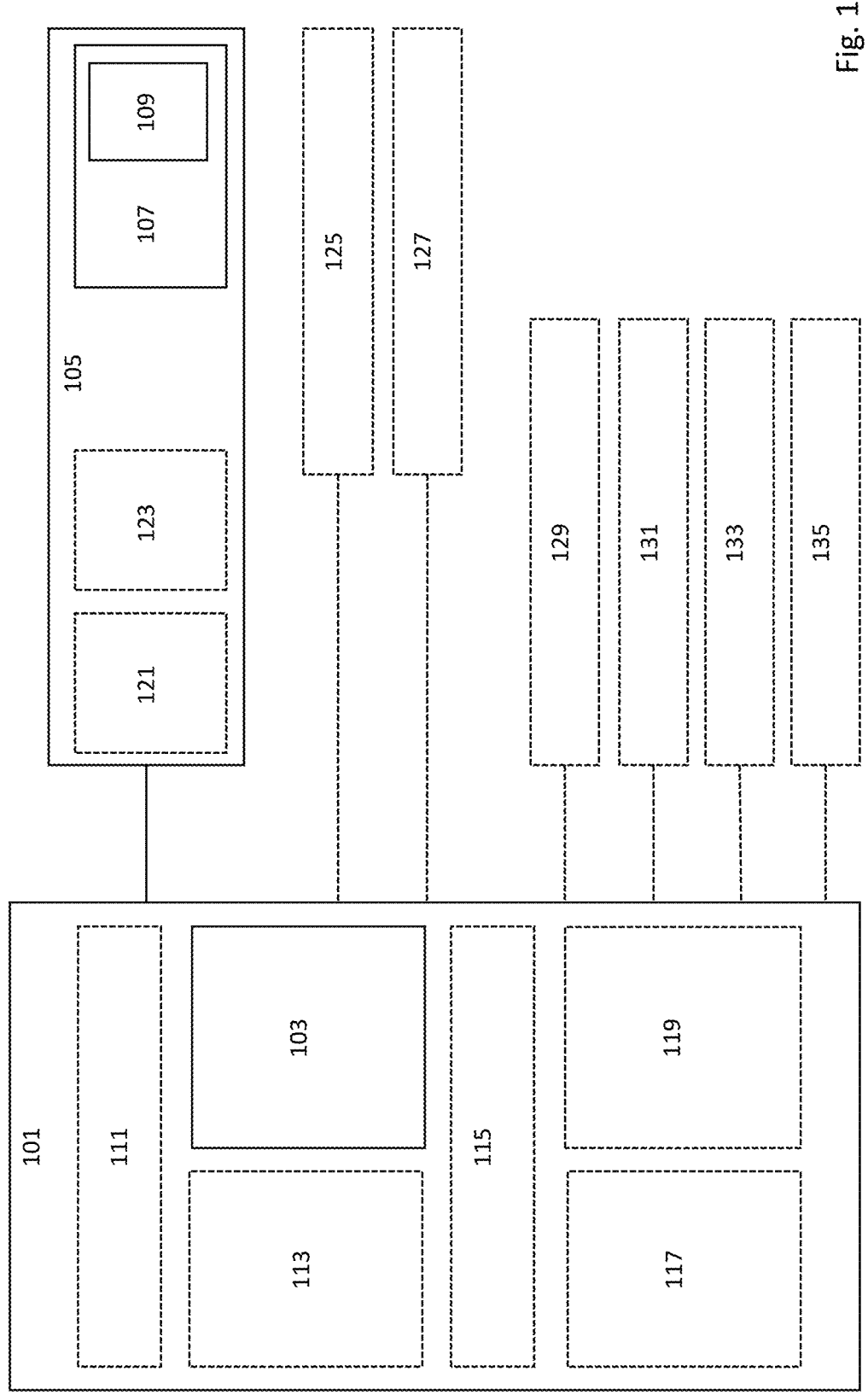
FIG. 1 is a block diagram of an exemplary ablation system.

FIG. 1 shows an ablation system (100) for pulsed field ablation of a target tissue. The ablation system (100) described herein includes a pulsed field ablation device (101). The ablation system (100) may include or may be connected to other parts or devices appropriate for performing or for supporting during performance of a method of the pulsed field ablation described herein. The other parts or devices may be for example a control unit (111), a graphical user interface (GUI) unit (113), electrical control circuits (115), electrocardiogram (ECG) triggering circuits (117), an ECG recording device (129), ECG electrodes (125), a pacing device (131), catheter signal interconnection circuits (119) and/or an electro physiology (EP) display device (133), which may include an EP recording system. The EP display device may show and/or record data from one or more other devices connected to the ablation system (100). Further, the ablation system (100) may include a mapping device (135), for example three-dimensional (3D) mapping device or a real position measurement (RPM) device, and/or indifferent electrodes (127). The mapping device (135) records EGM (intracardial electrograms) for a place in a space measured for example by a catheter and creates a map of a heart's surface. It may also show a position and orientation of the catheter. Other possible methods for measurement of a catheter's real position may be via a sensor in a catheter (for example position measurement based on magnetics) or for example using impedance measurements on a catheter's electrodes or a measurement based on radiofrequency or a combination thereof. Advantageously, in some examples, the catheter used for the position measurements is the same catheter that is used for the ablation.

The pulsed field ablation device (101) includes a pulse generator (103) for generating short high voltage electrical pulses and a catheter (105) suitable for insertion into a cavity of a patient's body with a catheter distal tip (107) suitable for performing the pulsed field ablation of target tissue by pulsed electric fields with a set of electrodes (109). The catheter (105) being in electrical connection with the pulse generator (103).

Figure 32:
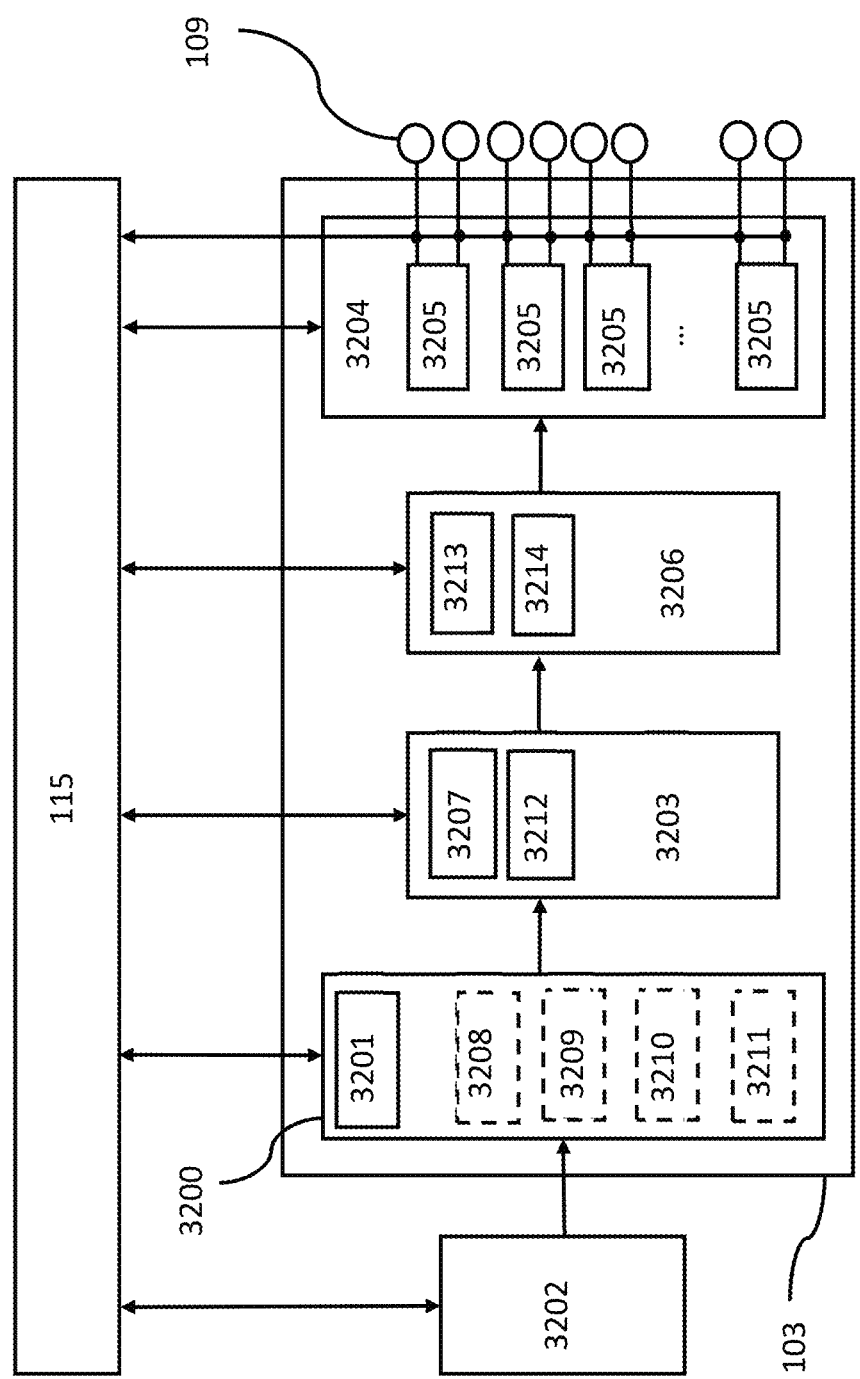
FIG. 32 is a block diagram of a pulse generator.

The generator (103) may be configured to generate high voltage electrical pulses, for example with a frequency of 0.1 Hz to 10 Hz, with an amplitude of the monophasic pulses varying from 100V up to 5 kV, and the peak-to-peak amplitude of biphasic pulses varying from 200V to 10 kV. A duration of the pulse can be from a nanosecond range to milliseconds range. An exemplary simplified schematic of the generator (103) may be seen in FIG. 32.

The generator (103) may comprise a power supply unit (3200) which may on its output produce a working voltage of for example from 100 V to 5000 V or from 250 V to 2000 V or from 500 V to 1000 V. The power supply unit (3200) may for example also transfer an AC current from a current source (3202) for example from a plug to a DC current in the output of the power supply unit (3200). The power supply unit (3200) may have an output power from 100 W to 5000 W or from 200 W to 3000 W or from 500 W to 1000 W. The power supply unit (3200) may include a regulator (3201), which regulates the production of the working voltage. The working voltage may be regulated, for example switched on and off according to feedback from the power supply unit (3200) output. The power supply unit (3200) may comprise a switched-mode power supply (3208), safety transformer (3209) (for example an AC to DC transformer), power factor correction block (PFC) (3210) for example configured to change the voltage coming from the current source (3202), for example to change it from approximately 230V to approximately 400V; and/or at least one DC/DC converter (3211). The power supply unit (3200) may be also coupled to electrical control circuits (115) and may be regulated, for example switched on and off according to a signal from the electrical control circuits (115).

The output of the power supply unit (3200) may be coupled to a capacitor unit (3203) including at least one capacitor (3212). The capacitor unit (3203) produces an energy for the high voltage electrical pulses. The capacitance of the capacitor unit (3203) may be for example from 50 µF to 1500 µF, or from 80 µF to 1000 µF, or from 160 µF to 750 µF. The capacitor unit (3203) may include an emergency system (3207) which may cause an emergency dissipation of the charge from the capacitor unit (3203) in case of any failure or any measured parameter outside of a safe boundary in the pulsed field ablation device (101). The emergency system (3207) may include a safety discharge resistor configured to safely discharge the capacitor (3212), thyristor protection and/or contactor for example configured for shorting the capacitor (3212) if needed. The operating speed of the emergency system (3207) may be for example from 50 ms to 100 ms.

The generator may further include a switching unit (3204) which may include for example at least one switch (3205), for example a semiconductor switch. The input of the switching unit (3204) may be coupled to the capacitor unit (3203), the output of the switching unit (3204) hence the switch (3205) may be coupled to at least one electrode (109) and may be configured for switching the electrode (109) to the mode of first polarity, mode of second polarity and into a mode of high impedance. The number of switches (3205) may depend on a number of independently switchable electrodes or independently switchable group of electrodes (109). One switch (3205) may be coupled to one electrode (109) or more than one electrode.

Figure 33:
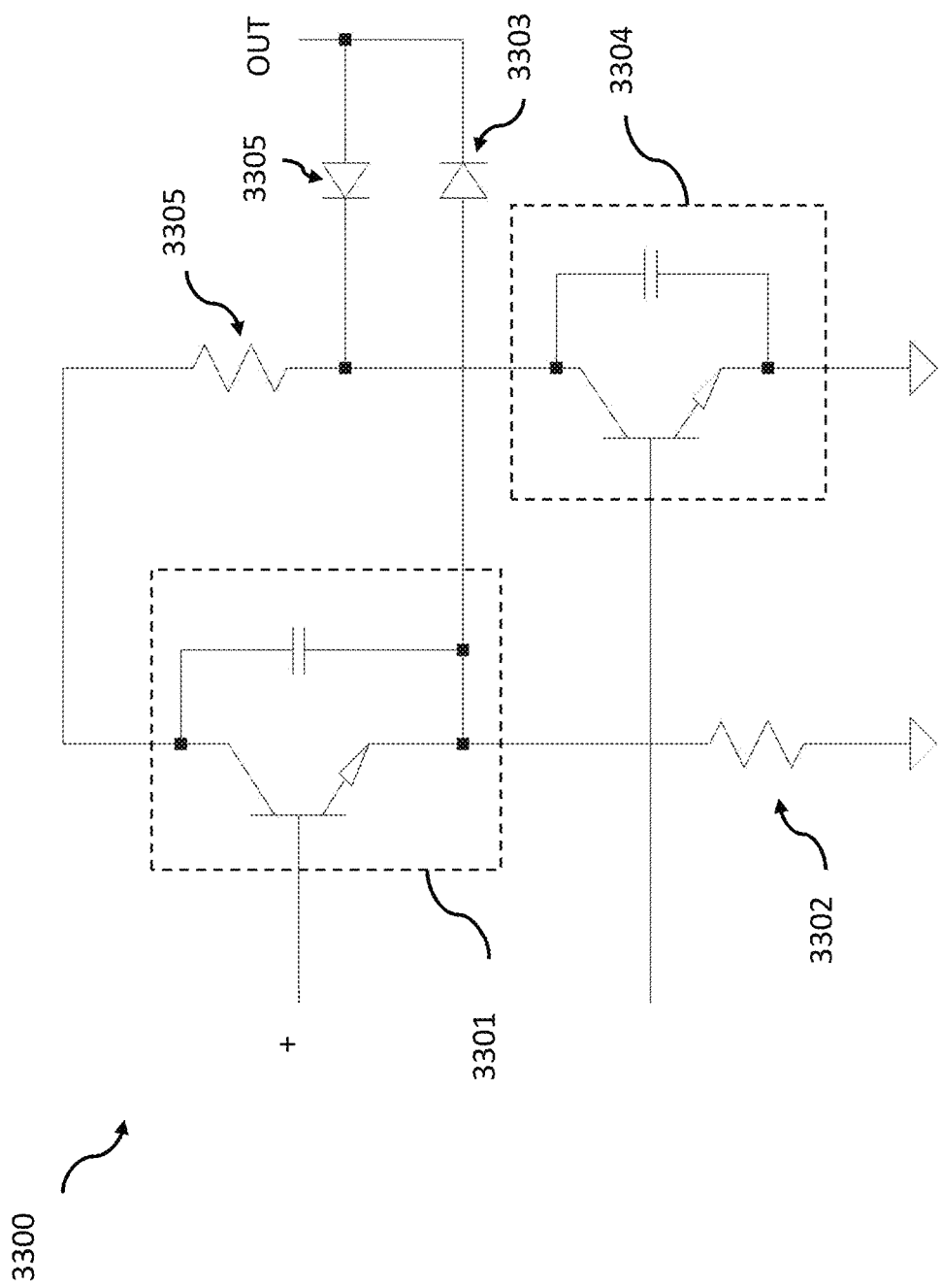
FIG. 33 is a schematic of a modified half-bridge.

The switch (3205) may be a semiconductor switch for example a modified half-bridge (3300). A schematic of the modified half-bridge (3300) may be seen in FIG. 33. The modified half-bridge (3300) is an improvement over a classic half-bridge. It solves the problem of parasitic properties of the classic half-bridge which is leakage current in closed state and output capacitance. The modified half-bridge (3300) may include a top side and a bottom side. The top transistor (3301) is coupled with a common collector. To the emitter of the top transistor (3301) is coupled a top resistor (3302) against ground. Due to the position of the top resistor (3302) the voltage across the top resistor (3302) is close to zero in the closed state of the top transistor (3301). The modified half-bridge (3300) may further include a top diode (3303). The top diode (3303) is coupled via its anode to the emitter of the top transistor (3301) and via its cathode to the output (OUT) of the half-bridge (3300). In the case of a closed top transistor (3301) (high impedance state) the top diode (3303) may ensure a current from the output of the half-bridge (3300) does not pass through the top resistor (3302). The bottom transistor (3304) has a common emitter, and there is a bottom resistor (3305) coupled to the collector of the bottom transistor (3304). The bottom resistor (3305) is coupled against the positive supply (+). Due to the bottom resistor (3305) the voltage across the bottom resistor (3305) is close to zero in the closed state of the bottom transistor (3304). The bottom diode (3306) is connected in reverse, i.e. the anode of the bottom diode (3306) is coupled to the output (OUT) of the modified half-bridge (3300) and the cathode is coupled to the collector of the bottom transistor (3304), preventing the output (OUT) of the modified half-bridge (3300) from having a permanent output voltage.

In an example when the switching unit (3204) is coupled directly to the capacitor unit (3203), the safety of the patient or the operator may depend on the reliability of the at least one switch (3205). In case of a failure of the switch (3205), the patient or the operator may face uncontrolled dissipation of the high capacitance of the capacitor unit (3203) for a duration of 50 ms to 100 ms.

For example to address such a danger for the patient or the operator, at least one DC/DC converter unit (3206) may be coupled between the capacitor unit (3203) and the switching unit (3204). The DC/DC converter unit (3206) may have an input voltage from 100 V to 5000 V or from 250 V to 2000 V or from 500 V to 1000 V and an output voltage from 150 V to 5000 V or from 500 V to 3000 V or from 1000 V to 2000 V. The DC/DC converter unit (3206) may for example include an output capacitor (3213) on its output.

The DC/DC converter unit (3206) may include an output capacitor emergency system (3214) which may cause an emergency dissipation of the capacitance from the output capacitor (3213) and shut down of a voltage delivery from the generator (103) to the electrode (109) in case of any failure or any measured parameter outside of a safe boundary in the pulsed field ablation device (101). The output capacitor emergency system (3214) may include a safety discharge resistor configured to safely discharge the output capacitor (3213), thyristor protection and/or contactor for example configured for shorting the output capacitor (3213) if needed. The emergency dissipation of the capacitance from the output capacitor (3213) and the shut down of a voltage delivery from the generator (103) to the electrode (109) may be shorter than 50 ms or than 25 ms or than 15 ms or than 5 ms or than 1 ms or than 100 µs or than 10 µs.

The capacitance of the output capacitor (3213) may be for example from 1 µF to 200 µF, or from 1.5 µF to 100 µF, or from 2 µF to 50 µF, or from 5 µF to 30 µF. The DC/DC converter unit (3206) may be for example a DC/DC converter without feedback. The DC/DC converter unit (3206) may be configured for converting the high capacitance of the capacitor unit (3203), into a lower capacitance at the output capacitor (3213). The DC/DC converter unit (3206) may be further configured for rapid discharge of the capacitance of the output capacitor (3213). The DC/DC converter unit (3206) may be for example further configured to limit leakage currents from the power supply unit (3200) to the patient for example below a limit of 10 µA. The leakage currents may be for example created by parasitic capacitance on the winding of the power supply unit (3200). The DC/DC converter unit (3206) may include two windings and may be for example a series resonant converter. The DC/DC converter unit (3206) may have for example a conversion ratio of from 1:1 to 1:6, or from 4:5 to 1:4 or from 2:3 to 1:3.

The power supply unit (3200), capacitor unit (3203), DC/DC converter unit (3206), switching unit (3204) and/or current source (3202) may be coupled to one or more electrical control circuits (115). The electrical control circuits (115) may for example receive data from the power supply unit (3200), capacitor unit (3203), DC/DC converter unit (3206), switching unit (3204) and/or current source (3202) and/or may send control signals to each of them. The data may comprise for example measured parameters in various places of the pulsed field ablation device (101), the generator (103), the power supply unit (3200), capacitor unit (3203), DC/DC converter unit (3206), switching unit (3204) and/or current source (3202). The measured parameters may be for example a temperature, impedance, current or voltage. The voltage may be for example measured on the output of the power supply unit (3200), capacitor unit (3203), DC/DC converter unit (3206), current source (3202) and/or switching unit (3204), for example on the output of the at least one switch (3205).

The electrical control circuits (115) may evaluate the received data and send control signals to the power supply unit (3200), capacitor unit (3203), DC/DC converter unit (3206), current source (3202), switching unit (3204) and/or to other parts of the ablation device (101) based on the received data. In case at least one of the measured parameters is out of predetermined boundaries the electrical control circuits (115) may for example send a control signal to the power supply unit (3200), capacitor unit (3203), DC/DC converter unit (3206), switching unit (3204) to activate a safety disconnection of the particular unit or all or a subset of the units. The safety disconnection may mean for example switching off the power supply unit (3200), activating the emergency system (3207) in the capacitor unit (3203) (discharging the capacitor (3212) to a safety discharge resistor and/or short the capacitor (3212) via a thyristor protection and/or contactor). In the DC/DC converter unit (3206) the safety disconnection may mean activation of the output capacitor emergency system (3214) (discharging the output capacitor (3213) to the safety discharge resistor and/or shorting the output capacitor (3213) via a thyristor protection and/or contactor). The safety disconnection in the switching unit (3204) may mean disconnecting at least one switch (3205).

The pulsed field ablation device (101) may include or may be connected to other parts or devices appropriate for performing or for supporting during performance of a method of pulsed field ablation described herein. The other parts or devices may be for example a remote control unit (111), a graphical user interface (GUI) unit (113), electrical control circuits (115), electrocardiogram (ECG) device including ECG triggering circuits (117), an ECG recording device (129), ECG electrodes (125), a pacing device (131), catheter signal interconnection circuits (119) and/or an electro physiology (EP) display device (133), which may include an EP recording system. The EP display device may show and/or record data from other devices connected to the ablation system (100). Further, the ablation system (100) may include a mapping device (135), for example a three-dimensional (3D) mapping device or a real position measurement (RPM) device, and/or indifferent electrodes (127). For example, the pulsed field ablation device (101) may be configured for use in or on a heart of the patient for example for the treatment of the heart tissue, for example for pulsed field ablation of the heart tissue, for example for pulsed field ablation of a myocardial tissue, for example for pulmonary vein isolation. Devices and methods disclosed herein may be used in other locations, for example all tubular tissues, organs or vessels in a body or for example tumor sites.

Figure 2:
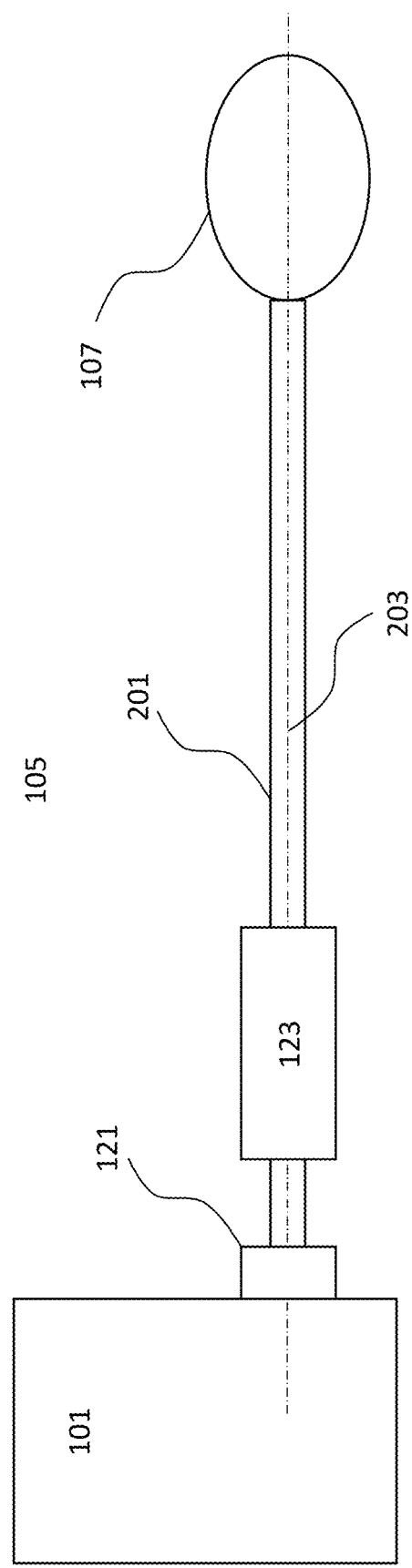
FIG. 2 is an overview of an exemplary pulsed field ablation device with catheter.

The catheter (105) shown in FIG. 2 includes a shaft assembly (201) and a catheter distal tip (107) located adjacent the distal portion of the catheter (105). The shaft assembly (201) defines a longitudinal central axis (203) of the catheter (105). The catheter (105) may further include a handle assembly (123) and a connection assembly (121). The catheter (105) may be steerable or non-steerable and can be introduced into its position for example via an introducer sheath (not shown) and with or without help of a guide-wire (not shown).

The connection assembly (121) of the catheter (105) may serve for interconnection of the catheter (105) with other parts of the ablation system (100). The connection assembly (121) may include a single connection portion or more spatially separated connection portions. The connection assembly (121) may be positioned at the proximal portion of the catheter (105) and/or for example may be a part of a handle assembly (123). The connection assembly (121) portion may include for example one or more electrical connections, mechanical connections, fluid connections and/or an input for a guide-wire.

The connection assembly may include at least one connector, for example electrical connector, fluid connector, data connector, optical connector, etc. The connector may serve for connection and disconnection of the catheter (105) with other parts of the ablation system (100).

The handle assembly (123) may be attached to the catheter shaft assembly (201) and may serve for example for steering and manipulation of the catheter (105), and/or for precise control of the movement and deflection of the catheter (105). In order to allow for the steering function, there may be knobs (not shown) connected to steering wires (not shown) that may be attached adjacent to the distal section of the catheter (105) fed through a separate lumen and connected to a knob or a steering mechanism (not shown) inside the handle assembly (123). The handle assembly (123) may further include the connection assembly (121) or one or more connection portions of the connection assembly (121), as well as other parts for example a grip (not shown) and/or a deployment mechanism (not shown) to deploy/retract the distal tip basket assembly (401, see FIG. 4) and/or expandable basket (409) by means of a push/pull of an inner elongated shaft (301) and/or an outer elongated shaft (303) relative to each other. The deployment mechanism may include for example an actuator for actuating the inner elongated shaft (301) against the outer elongated shaft (303) in a longitudinal direction.

Figure 3A:
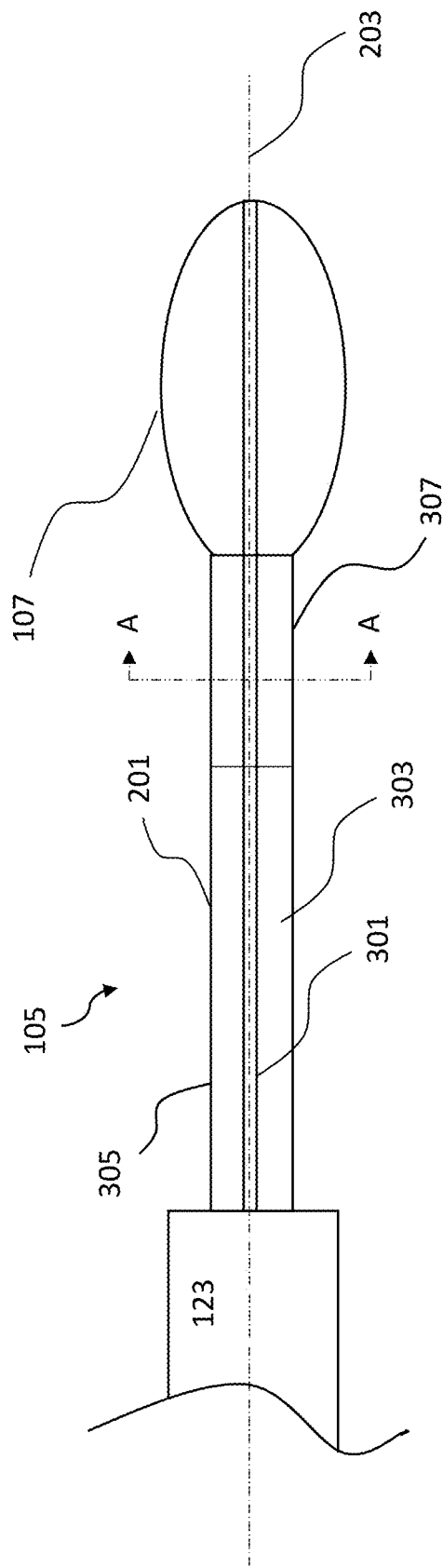
FIG. 3A shows an exemplary catheter with a shaft assembly.
Figure 3B:
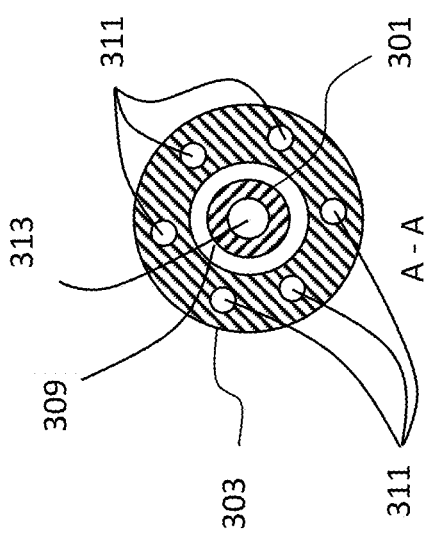
FIG. 3B is an exemplary representation of a cross-section of a shaft assembly.

FIG. 3A shows the catheter (105) with a shaft assembly (201). The shaft assembly may comprise an outer elongated shaft (303) and/or an inner elongated shaft (301). A cross section of an exemplary shaft assembly (201) in a section A-A shown in FIG. 3B, may include two concentric tubes, the outer tube being the outer elongated shaft (303), the inner tube being the inner elongated shaft (301). The shafts can translate relative to each other in a longitudinal direction along the longitudinal central axis (203). This translation can for example allow the deployment/retraction of the expandable basket (409) from a collapsed configuration to a fully expanded configuration and back.

The outer elongated shaft may comprise a proximal portion, a distal portion, and a body extending between a proximal and a distal end. The outer elongated shaft may be coupled to the handle assembly adjacent to its proximal portion and to the catheter distal tip adjacent to its distal portion.

The body of the outer elongated shaft (303) may include one or more lumens (309, 311), extending for instance along its entire length between the proximal and distal ends. The lumens may be for example adapted to lead wires or fluids, for example an irrigation fluid. One or more of the lumens may be configured to accept one or more of the inner elongated shafts. The body of the outer elongated shaft can be for example further defined by a proximal section (305) and a midsection (307). The midsection of the body may be designed with a flexible jacket compared to the proximal section to allow bending and increase flexibility of the outer elongated shaft. The proximal section for instance includes a stiffer material jacket to increase the torque and rigidity of the body of the outer elongated shaft. Suitable materials for construction of the jacket include, but are not limited to Nylon, TPU, HDPE or PEBA.

The body of the outer elongated shaft may include conductive wires. The conductive wires may lead through the outer elongated shaft's central lumen (309), or the outer elongated shaft may include several other lumens (311), hence one or more of the wires may lead through one or more of the other lumens (311). For example, the number of other lumens may match the number of filaments of a braided mesh on the catheter distal tip, for example if 20 filaments are used in the construction of the catheter distal tip, 20 other lumens may be used.

The conductive wires may extend from the basket assembly to the connection assembly for example adjacent to the handle assembly.

In some aspects, the inner elongated shaft may be configured to slide along the longitudinal central axis relative to the outer elongated shaft. Therefore, one or more of the lumens may for instance comprise a low friction liner, for example a polytetrafluoroethylene (PTFE) liner.

Rigidity and torque are important features that the outer elongated shaft should have, hence laterally above/around the PTFE liner the outer elongated shaft may include for example a braid of a metal or a rigid polymer wire wrapped around the inner layer of the body, which in some aspects is embedded within the outer jacket of the body, or may comprise a rigid polymer including but not limited to Polyimide, Polyamide, Polyether ether ketone (PEEK) or any other suitable material.

The outer layer of the outer elongated shaft may comprise a laminated polymer to provide a seamless, smooth and soft surface. Note that, as mentioned earlier, the outermost layers of the midsection and proximal section may be formed of different polymers, for example a nylon material could be used on the proximal section, while for example a PEBA, which is more flexible compared to nylon, could be used on the outermost layer of the midsection. Yet, both sections may have the same innermost layers. The outer elongated shaft may have a substantially constant outer diameter along its length.

The Outer Diameter (OD) dimension of the outer elongated shaft may for example fit the French catheter scale that is commonly used for catheter sizing standardization. The diameter in this scale is defined in Frenches (FR), where 1 mm=3 FR. The scale is usually from a 3 FR catheter up to a 34 FR catheter. For instance, the diameter of the outer elongated shaft may be between 5 FR to 20 FR, or from 7 FR to 16 FR, or from 9 FR to 15 FR. The diameter of the central lumen of the outer elongated shaft can be approximately between 0.1 mm and 5 mm, or 1 mm to 4 mm, or 2 mm to 3.5 mm, or 2.5 mm to 3 mm.

The inner elongated shaft may comprise a proximal end, a distal end, and a body extending between proximal and distal ends. The body of the inner elongated shaft may include one or more lumens (313), extending for example along an entire length between the proximal and the distal end of the inner elongated shaft or can have no lumen. The one or more lumens (313) of the inner elongated shaft may be for example designed to accommodate a standard guide-wire (not shown) and/or to lead a fluid, for example an irrigation fluid. The diameter of the one or more lumens (313) may be from 0.1 mm to 3 mm, or from 0.5 mm to 1.5 mm, or from 0.9 mm to 1 mm, or from 0.94 mm to 0.99 mm. One or more of the inner elongated shafts can be suitable for placing in the one or more lumens (309, 311) of the outer elongated shaft. Dimensions of the inner elongated shaft may be chosen to match the diameter of the designated lumen of the outer elongated shaft, but still the two structures need to allow their smooth relative translation. That means the outer dimensions of the inner elongated shaft (301) can be from 0.1 mm to 4.9 mm, or from 0.5 mm to 3.5 mm, or from 1 mm to 3 mm, or from 1.28 mm to 2.8 mm.

Since the inner elongated shaft can be suitable for accommodation of a guide-wire inside its lumen, a low friction liner, for example a PTFE liner, of the inner lumen can be used.

As mentioned above, the inner elongated shaft can be translated relative to the outer elongated shaft to deploy the basket assembly/expandable basket, hence for instance a braided socket is weaved along the length of the PTFE liner creating a body of the inner elongated shaft. Another aspect may include a cut hypotube instead of a braid in a body of the inner elongated shaft to improve its flexibility and torque.

Laterally above the layer with the braid or the hypotube, a polymer jacket can be melted/laminated to enhance the softness of the tube and provide a seamless surface. A variety of polymers could be used for the jacket, exemplary materials may be NYLON, polyether block amide (PEBA), Polyether ether ketone (PEEK) or Polyimide.

Figure 4:
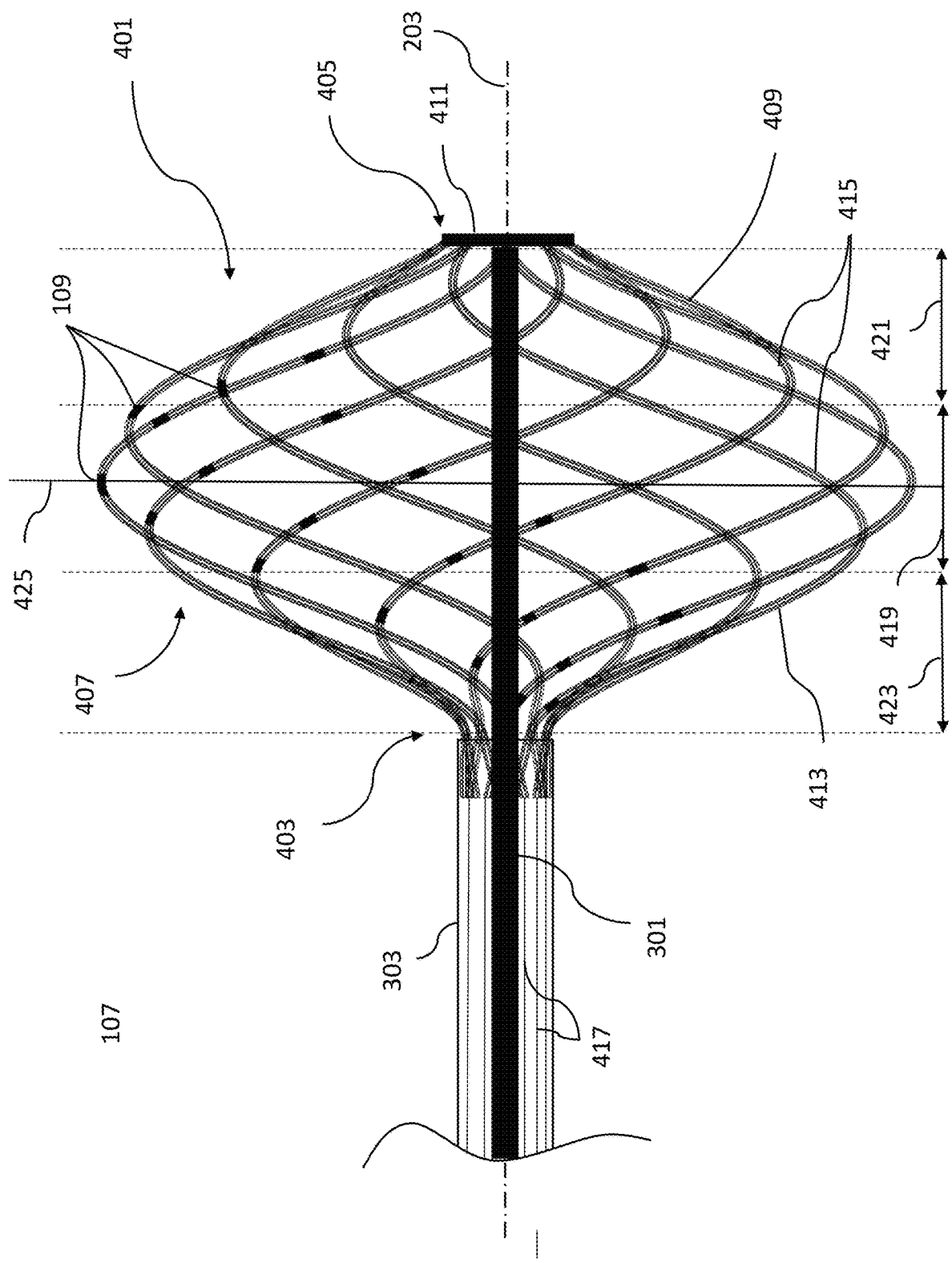
FIG. 4 is an exemplary representation of a distal tip of the catheter with a basket assembly in expanded configuration.

The distal tip (107) of the catheter of the example shown in FIG. 4, further includes a basket assembly (401). The basket assembly (401) may comprise a basket assembly proximal portion (403), a basket assembly distal portion (405) and a basket assembly body (407) extending between the proximal and distal portions. The basket assembly body may include a central body portion (419) spreading around the plane (425) intersecting the basket assembly in a portion with a highest diameter (in one of its expanded configurations) in proximal and distal directions, occupying about ⅓ of the basket assembly body. The basket assembly body may further include a distal body portion (421) extending distally from the central body portion (419) and proximal body portion (423) extending proximally from the central body portion (419), each of them occupying about ⅓ of the basket assembly body (407).

The basket assembly (401) comprises an expandable basket (409). The basket assembly proximal portion (403) may include an attachment of the proximal portion of the expandable basket (409) adjacent to the distal end of the outer elongated shaft (303). The distal portion of the basket assembly (401) may include an attachment of the distal portion of the expandable basket (409) adjacent to the distal end of the one or more of the inner elongated shafts (301) creating a terminal assembly (411).

Figure 28:
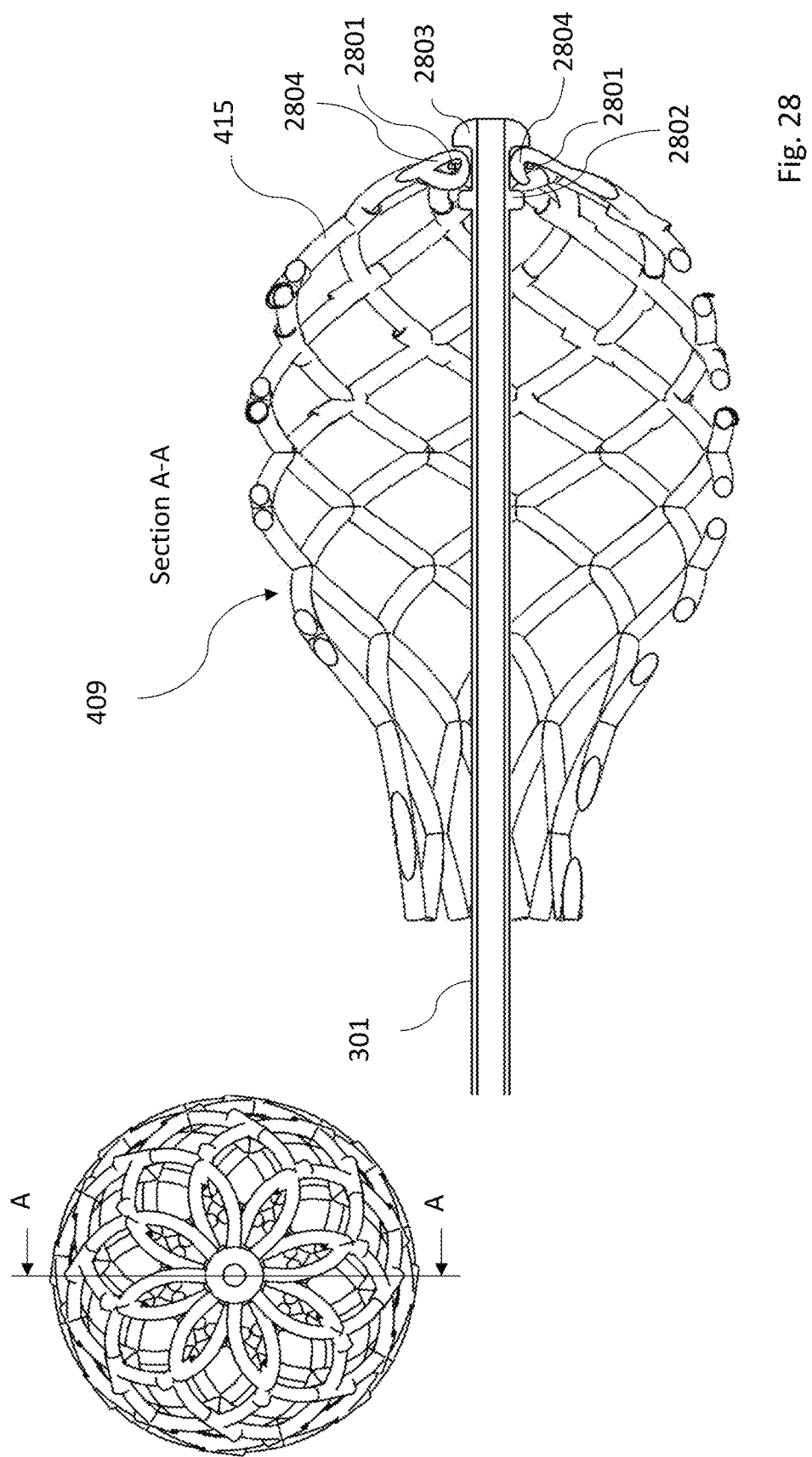
FIG. 28 shows a section of an expandable basket fixed to the inner elongated shaft.
Figure 29:
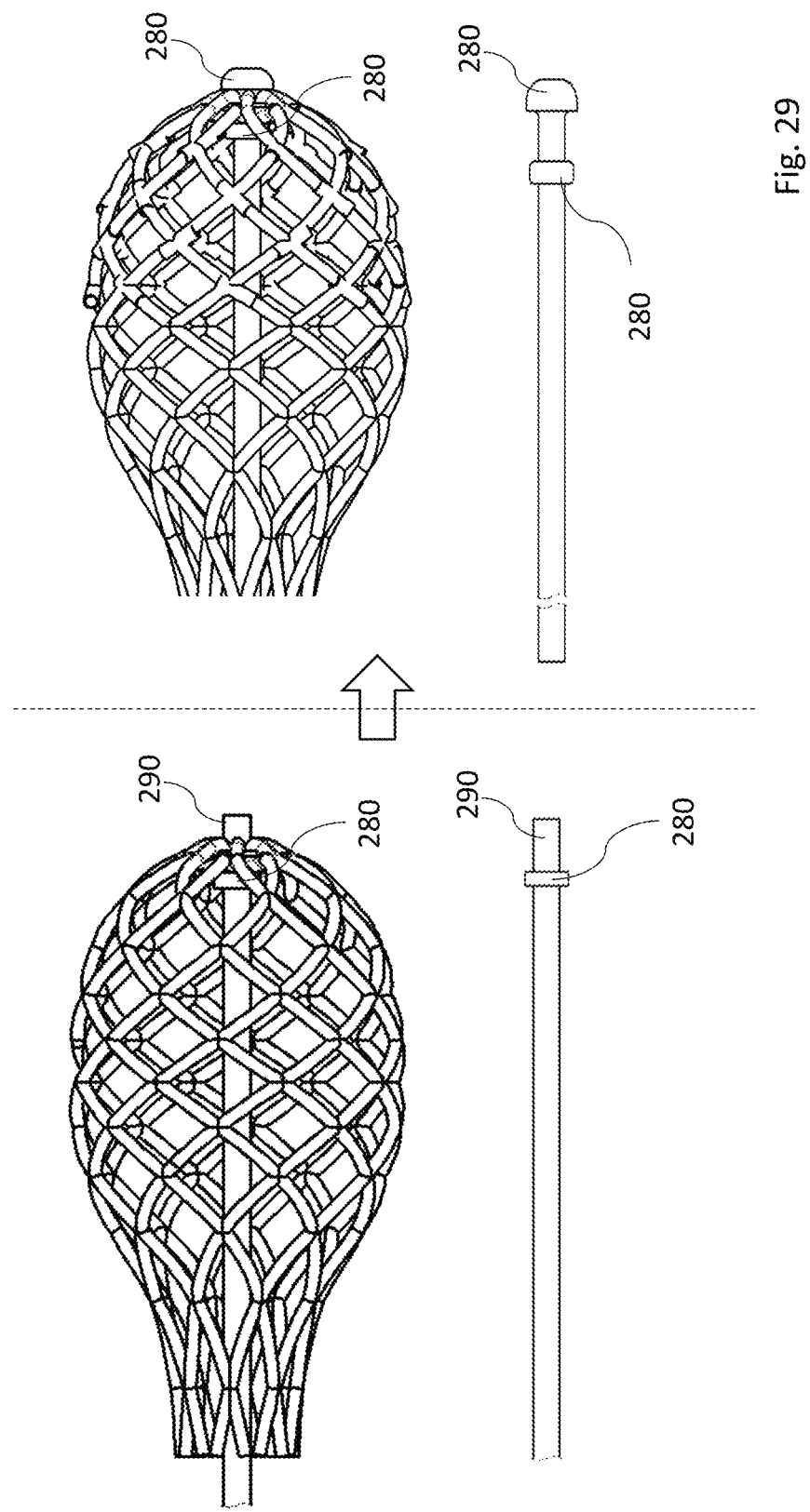
FIG. 29 is a view of an example of an inner elongated shaft end and expandable basket before and after their mutual mechanical attachment.

An example of the attachment of the distal portion of the expandable basket (409) adjacent to the distal end of the one or more of the inner elongated shafts (301) may be found in FIG. 28. In this particular example the distal end of the expandable basket (409) may be created with help of a ring (2801) to which the filaments (415) are fixed or are bent around in a place (2804) of fixation of the filaments (415) to the ring (2801). The distal portion of the expandable basket (409) is attached to the inner elongated shaft (301) by a mechanical locking mechanism. To lock the basket to the shaft two protrusions (2802, 2803) are created on the inner elongated shaft (301) so that they hold either side (proximal and distal) of the basket distal end, for example including the ring (2801) which will lock the expandable basket (409) to the inner elongated shaft (301). The assembly is created by pushing the inner elongated shaft (301) with prepared first protrusion (2802) distally through the opening in a distal part of the expandable basket, for example through a hole of the ring (2801) until the first protrusion (2802) on the shaft reaches the distal part of the expandable basket from the proximal side as shown in FIG. 29. The inner elongated shaft end (2901) (the one protruding distally from the basket) is then tipped/heated on a bullet shape mold to create the second protrusion (2803) with an atraumatic bullet shape end that will prevent the inner elongated shaft (301) from moving proximally relative to the expandable basket (409). This connection is made in a way to lock the inner elongated shaft (301) to the expandable basket (409) under operating conditions, but also in a way that the connection will break and get loose under a certain axial load in case basket un-deployment is not possible and the catheter needs to be retrieved from the patient. The axial load (force) needed to brake the connection may be from 10 N to 100 N, or from 15 N to 75 N, or from 20 N to 50 N.

Figures 30A, 30B:
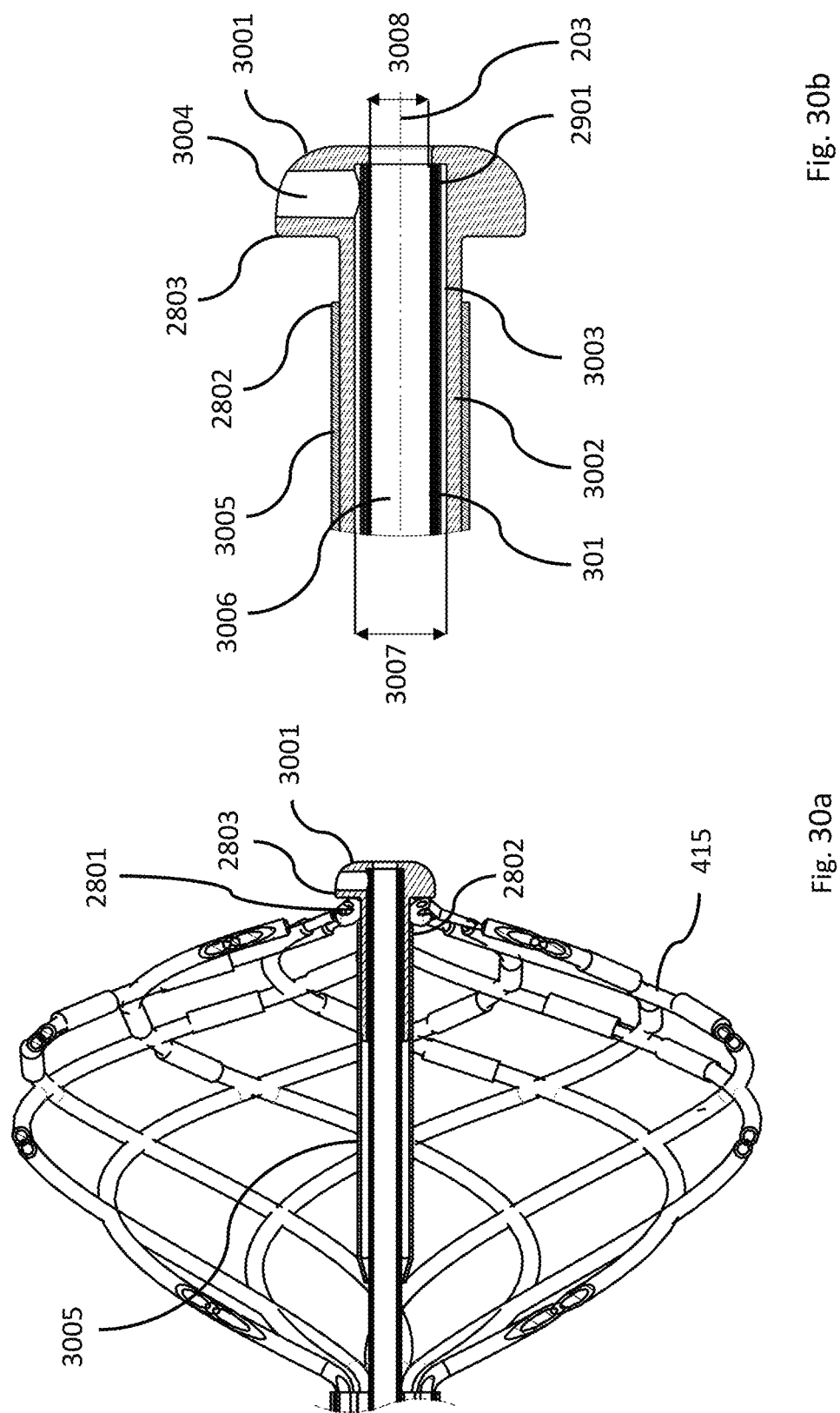
FIG. 30a is a view of a section of an expandable basket fixed to the inner elongated shaft.
FIG. 30b shows a detail view of exemplary protrusions on the inner elongated shaft.

The protrusions (2802, 2803) may be formed on the inner elongated shaft by other techniques as well. One particular example is shown in FIGS. 30a and 30b. The second protrusion (2803) may be in this example formed by a distal additional member (3001) coupled to the inner elongated shaft (301) for example to the inner elongated shaft end (2901). The distal additional member (3001) may be for example in a form of toroidal, cylindrical, conical, truncated conical, or hollow tubular body, for example with an atraumatic shape (e.g. bullet shape, flange shape) formed on its distal end for example to ensure the terminal assembly will not mechanically injure a patient, and it may be for example made out of plastic or metal. The distal additional member (3001) may include a tubular structure (3002) protruding proximally from the second protrusion (2803) parallel with the inner elongated shaft. The distal additional member (3001) and/or the tubular structure (3002) may include a cavity (3006) for example adapted to receive at least portion of the inner elongated shaft (301) for example the inner elongated shaft end (2901) and a guidewire. The cavity (3006) may have two inner diameters, a first diameter (3007), formed proximally in the distal additional member (3001) large enough to fit the at least portion of the inner elongated shaft (301), for example the inner elongated shaft end (2901) and a second diameter (3008), formed distally from the first diameter (3007) with a smaller diameter than the first diameter (3007) and a smaller than an outer dimeter of the inner elongated shaft (301) configured for example for a guide wire to pass through. With such configuration of the cavity (3006) the distal additional member (3001) may act as a distal stopper for the inner elongated shaft (301) in the direction of the longitudinal central axis (203), while also preventing possible sharp edges of the inner elongated shaft end (2901) from being exposed distally of the distal additional member (3001) and possibly causing tissue damage upon contact. The distal additional member (3001) may be coupled to the inner elongated shaft (301) and the coupling may include for example a crimp, weld, screw, thread, melted plastic or an adhesive, for example a hot melt adhesive or a glue.

In a particular example shown in FIGS. 30a and 30b the distal additional member (3001) may be coupled to the inner elongated shaft (301) for example by a melted plastic or an adhesive. The distal additional member (3001) may include a cavity with a diameter larger, for example larger by from 0.1% to 50% or from 0.5% to 40% or from 1% to 25%, than an outer diameter of the inner elongated shaft (301). The inner elongated shaft may be inserted into the cavity and the resulting space (3003) between the inner elongated shaft (301) and walls of the cavity may be filled with an adhesive, for example hot melt adhesive or glue. The distal additional member (3001) may include a glue opening (3004) for this purpose, which may serve as an access for the adhesive into the resulting space (3003). After filing the glue into the resulting space (3003), the glue opening (3004) may be closed and sealed, for example by a plug, a melted plastic or by an adhesive for example by a hot melt adhesive or by glue, possibly the same one as used for coupling of the distal additional member (3001) to the inner elongated shaft (301).

The first protrusion (2802) as shown in an example in FIGS. 30a and 30b may be for example formed by means of a tubular proximal additional member (3005) coupled to the inner elongated shaft (301). The proximal additional member (3005) may be directly coupled to the inner elongated shaft (301), or it may be coupled to the inner elongated shaft (301) for example via the distal additional member (3001), for example to the tubular structure (3002). In another example shown in FIGS. 30a and 30b the proximal additional member (3005) may be coupled to the inner elongated shaft (301) both directly and indirectly via the distal additional member (3001). The coupling of the proximal additional member (3005) to the inner elongated shaft (301), and/or to the distal additional member (3001) may for example include a crimp, weld, screw, thread, melted plastic, an adhesive, for example a hot melt adhesive or a glue, or another fixation member (not shown) for example placed proximally on the inner elongated shaft (301). The first protrusion (2802) may have a form or may include for example a plastic tube.

The ring (2801) to which the filaments (415) are fixed may be coupled to the inner elongated shaft (301) directly, or for example via the distal additional member (3001) or the proximal additional member (3005). One example of the ring (2801) coupled to the inner elongated shaft (301) via the distal additional member (3001) is shown in FIGS. 30a and 30b. In this particular example the distal additional member (3001) includes the tubular structure (3002) protruding proximally from the second protrusion (2803) parallel with the inner elongated shaft and the ring (2801) may encircle the tubular structure (3002).

The terminal assembly (411) may be advantageously designed without, or at least with reduced structures protruding in the distal direction from the basket assembly distal portion (405), for example a cap or similar formation. This is especially advantageous in situations where at least part of the ablation method needs to be performed on a relatively flat treatment site.

An exemplary solution of terminal assembly may be an overmolded structure. Filaments may be fixed to each other and/or to distal end of the inner elongated shaft by an overmolding process, creating an overmolded terminal assembly. Another fixation procedure (and/or terminal assembly creating procedure) similar to overmolding may be for example tipping, where the filaments are at least partially melted and pressed into a pre-shaped mold and so connected together and/or to the inner elongated shaft. A lamination is another example process to fix the filaments at their distal ends to create a terminal assembly. The terminal assembly may be created by swaging or crimping of a filament's distal ends as well. The filaments may be brought together at the terminal assembly area and swaged or crimped together by for example some kind of metal ring.

Figure 18:
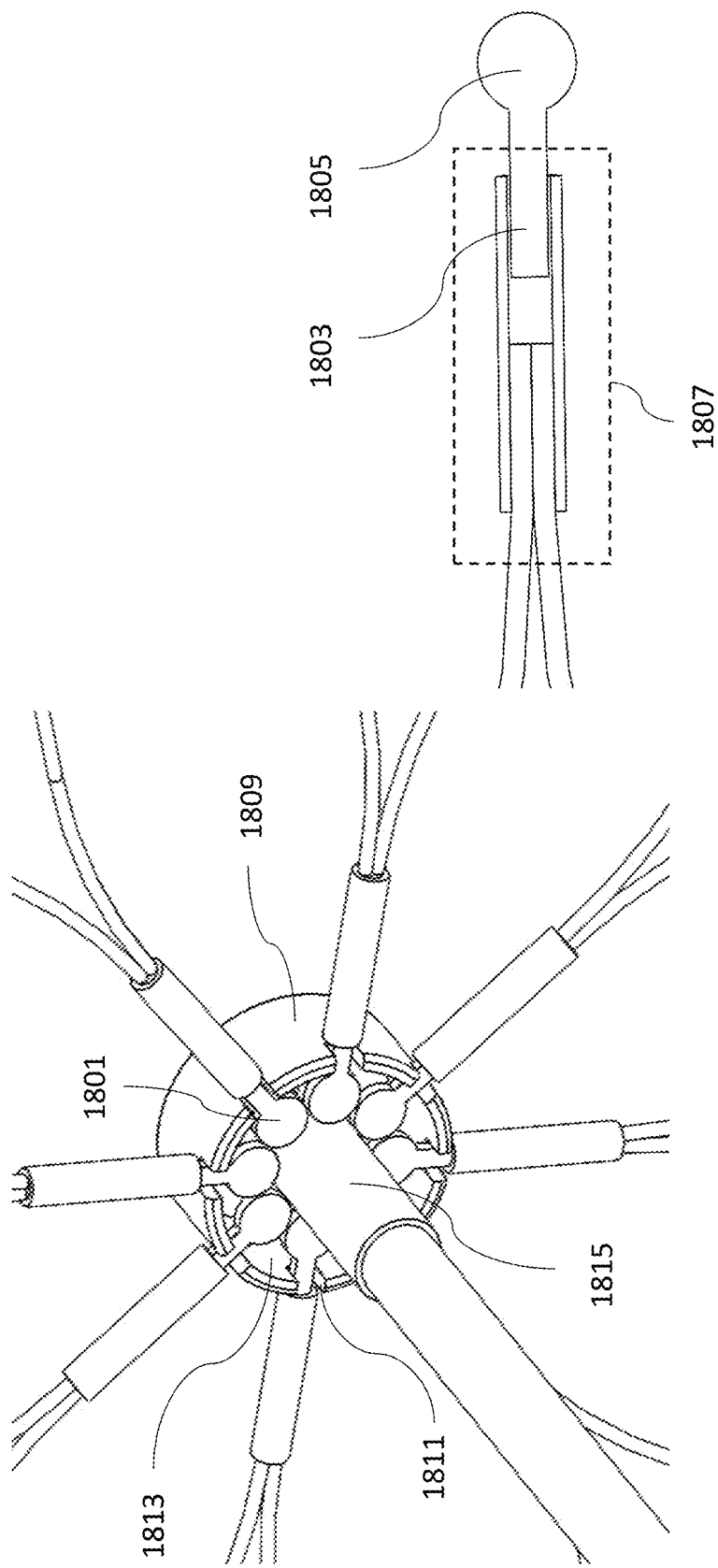
FIG. 18 is a view of one example of a terminal assembly.
Figure 19:
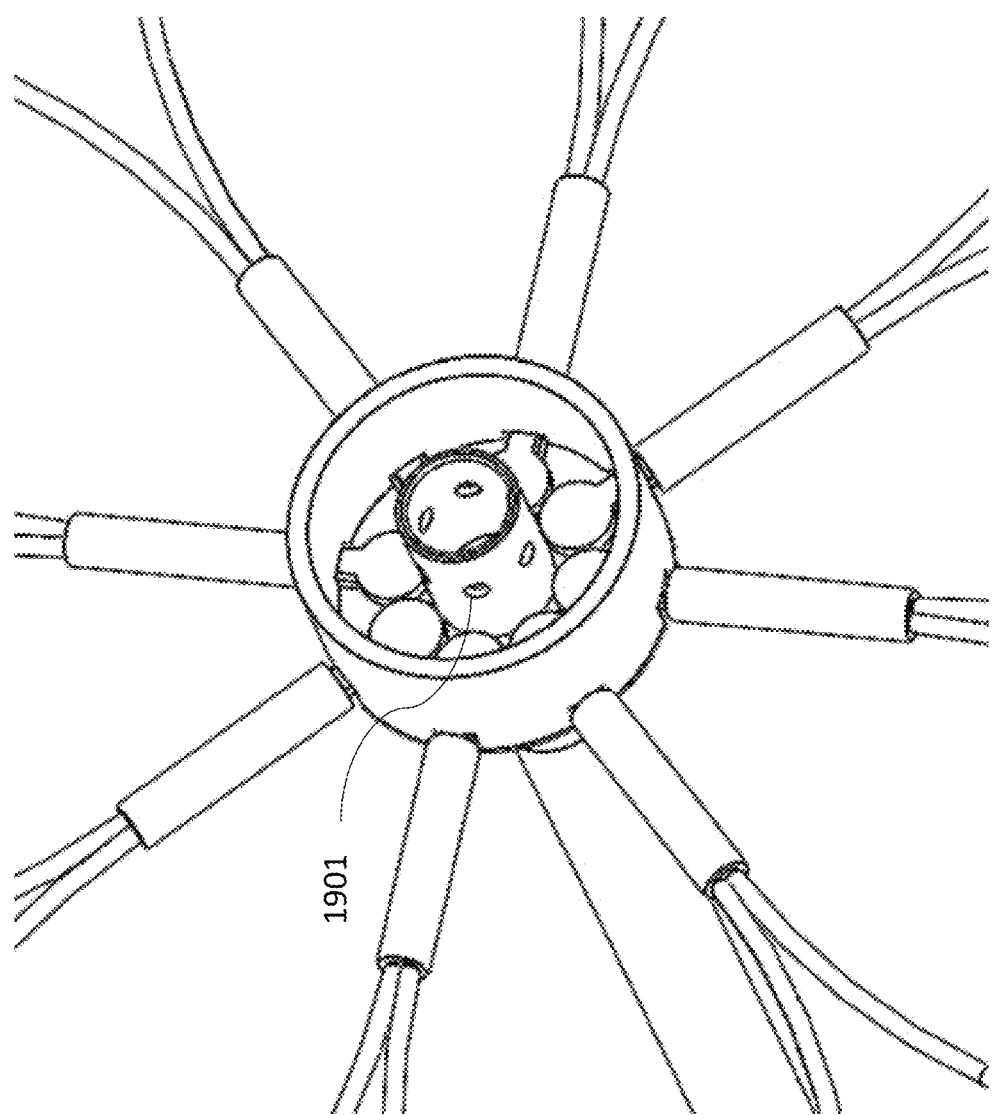
FIG. 19 shows another view of an exemplary terminal assembly.

In another example a terminal assembly may be created as a hinged mechanical structure as shown in FIG. 18. For example, one or more filaments may be at their distal end in the area of terminal assembly fixed to articulated elements (1801), which comprise for example lateral narrow portion (1803) and distal portion (1805) which is wider than lateral narrow portion (1803). The lateral narrow portion (1803) may be for example in a form of pin with square, rectangular, circular, oval or other suitable cross section. The distal portion (1805) may have for example a form of an oval or a circle or in another example of ball or sphere. Other possible shapes of the distal portion (1805) could be cylinder, cone, cube or block. It may have one of the dimensions the same as the lateral narrow portion (1803), for example in case the whole articulated element (1801) is made out of one piece of sheet-like material (metal sheet, polymer sheet) or not (for example in case the articulated element is casted or forged). The articulated element (1801) may be for example made of metal (for example nitinol) or other material for example polymer or thermoplastic. The fixation of filaments to the articulated elements may be done for example by welding, gluing or crimping. An area of the connection (1807) may be for example at least partially laminated to prevent possible tissue damage and to seal the assembly. The articulated elements are then fixed in a central bullet structure (1809). This may be for example a hollow structure with cut windows (1811) suitable for accommodation of the proximal part (1803) of the articulated elements (1801). The distal parts (1805) of the articulated elements are in this case placed in the cavity (1813) inside the hollow structure. The distal parts (1805) of the articulated elements may in some examples have dimensions (cross section or width) bigger than dimensions of windows (1811). This prevents slipping of the distal parts (1805) of the articulated elements (1801) through the windows (1811) thus holding articulated elements, and together with them the connection area (1807) and distal parts of the filaments attached to the central bullet structure (1809). The central bullet structure (1809) may comprise several parts connected together (for example by welding, gluing or other mechanical means like snaps, threading, screws, bolts . . . ). It may have different outer shapes as well, for example a cylindrical, spherical or oval. The shape of the cavity (1813) may correspond to the outer shape or may differ. The central bullet structure may include fixation part (1815) for fixation of a distal end of an inner elongated shaft to the central bullet structure. The fixation part (1815) may have for example a shape of a hollow tube connected to the central bullet structure. The fixation part is suitable for accommodation and/or connection of a distal part of the inner elongated shaft and may allow for a flow and/or redirection of a fluid, for example an irrigation fluid coming out of a lumen of the inner elongated shaft. The fixation part may interfere or may be in mechanical and/or fluid connection with the cavity (1813). It may be adapted to direct at least part of the irrigation fluid into the cavity of a central bullet structure for example by apertures (1901) as shown in FIG. 19.

Such a hinge mechanical structure as described above may allow for easier radial movement (regarding longitudinal central axis of the catheter) of the filaments in the area of terminal assembly, which may be advantageous during manipulation with an expandable basket, particularly with transition (deployment/retraction) between a collapsed configuration and one or more expanded configurations.

In case metal parts are used in the design of a terminal assembly, they may be for example used as electrodes, either for ablation or for sensing or mapping or combination of thereof.

The expandable basket may be attached to the inner elongated shaft and/or to the outer elongated shaft for example by gluing, welding, lamination or by mechanical means.

Figure 5:
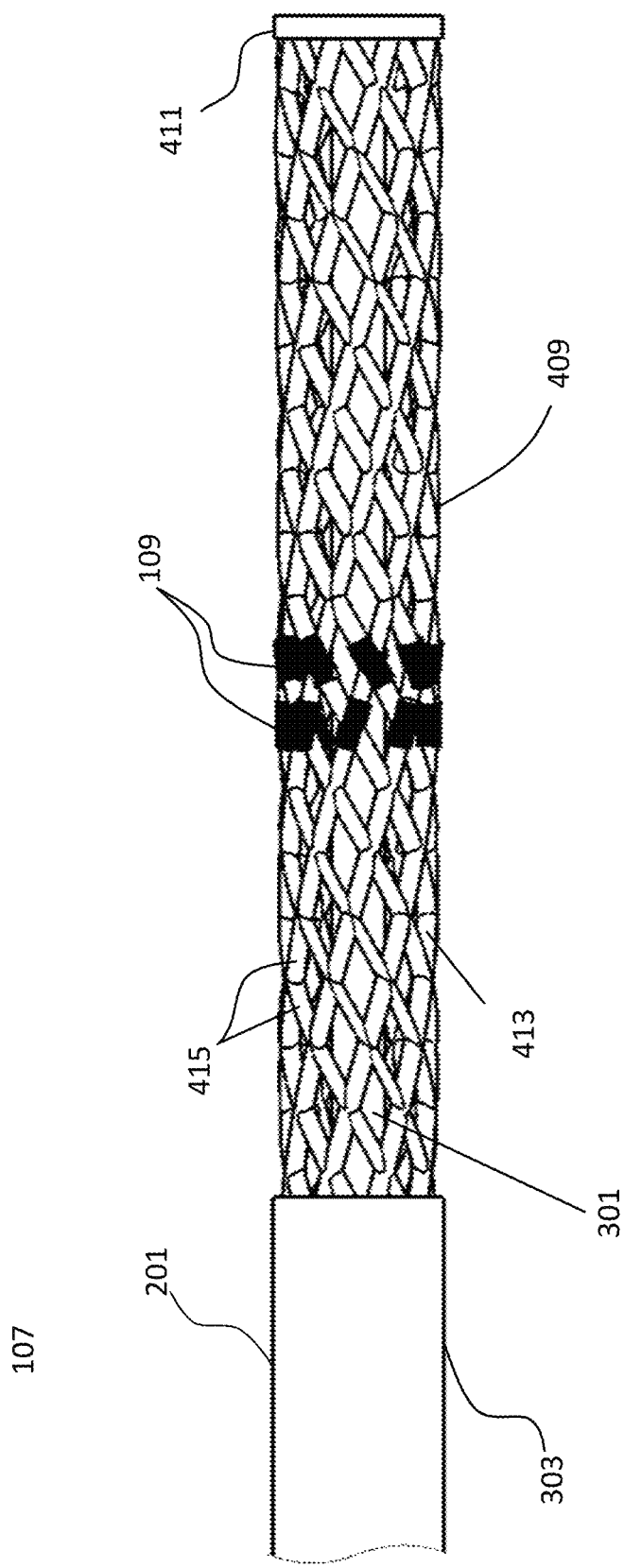
FIG. 5 shows an exemplary distal tip of the catheter with a basket assembly in collapsed configuration.

The expandable basket (409) is for instance configured for transition (deployment/retraction) between a collapsed configuration, shown in FIG. 5, and one or more expanded configurations. The transition (deployment/retraction) can be caused by a pre-tension shape of the braided mesh (413) and/or filaments (415) and/or by a linear displacement of the inner elongated shaft (301) against the outer elongated shaft (303) along a longitudinal central axis (203) of the catheter (105) or by combinations thereof. Another possibility for deployment/retraction of the expandable basket (409) may be by a tension of an additional supportive structure for example an inner coil or balloon (not shown).

The expandable basket may comprise filaments braided into a braided mesh or a molded mesh. In the collapsed configuration, the cross-section of the expandable basket may be equal or dimensionally close to the cross-section of the outer elongated shaft, though in one aspect the cross-section of the expandable basket may be smaller than the cross-section of the outer elongated shaft and may depend on the dimensions of the outer elongated shaft. In the expanded configuration the cross-section of the expandable basket may be significantly larger than the cross-section of the outer elongated shaft. Fully expanded expandable basket may have a maximum cross-sectional diameter of, for example, from 20 mm to 40 mm or from 22 mm to 38 mm or from 25 mm to 35 mm. Such dimensions of a fully expanded expandable basket may be suitable for example for placement in heart cavities. For larger body cavities, for example, the expandable basket may have larger dimensions, e.g. from 30 mm to 150 mm, or from 40 mm to 120 mm, or from 50 mm to 100 mm. In other situations, a fully expanded expandable basket having smaller dimensions may be suitable for smaller body cavities. Such a smaller expandable basket may have dimensions in its fully expanded state for example from 3 mm to 25 mm, or from 5 mm to 15 mm, or from 7 mm to 10 mm.

Figure 6B:
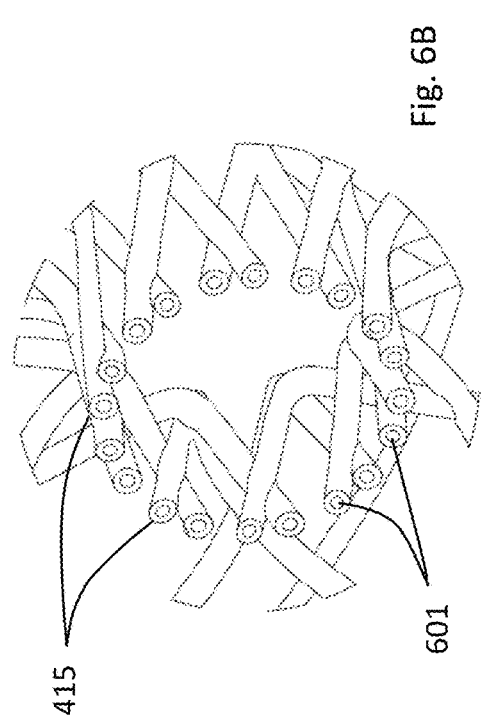
FIG. 6B is a detail view of an exemplary expandable basket with filaments.
Figure 6C:
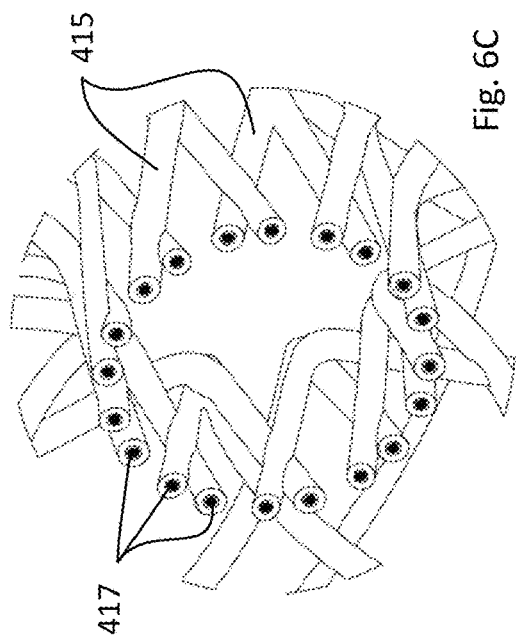
FIG. 6C is a detail view of an exemplary expandable basket with filaments and conductive wires.
Figure 6A:
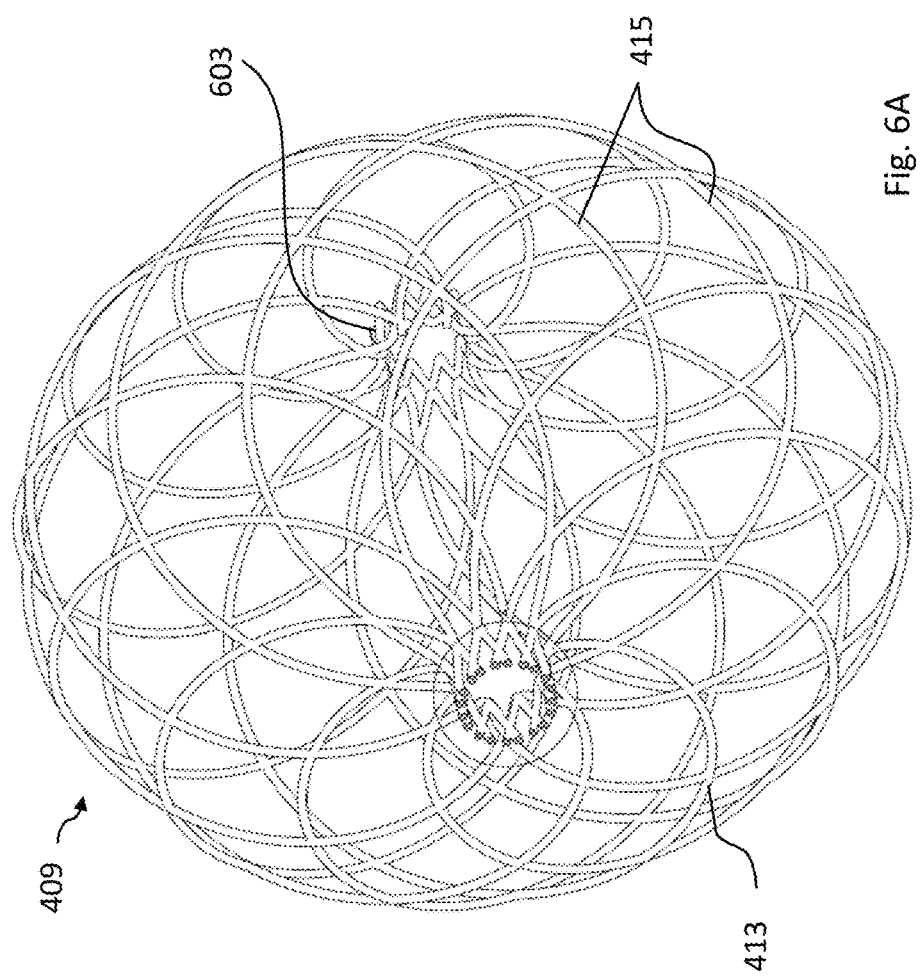
FIG. 6A shows an exemplary expanded expandable basket.

In some aspects, the filaments (415) braided into the braided mesh (413) are not cut adjacent to the distal portion of the expandable basket (409), but the filaments (415) may rather be bent at the distal portion and attached adjacent to the distal portion of the inner elongated shaft creating a terminal assembly. The bent filaments may then be directed back to the expandable basket (409) or the outer elongated shaft, where they can be terminated. FIG. 6A shows the expandable basket (409) in greater detail with bent filaments in its distal portion (603).

The expandable basket made out of the braided mesh has advantages over a prior art solution with unbraided struts, in that the expandable basket has higher mechanical stability even while using comparably thinner filaments. More filaments in the structure may also allow more electrodes to be used. The electrodes placed on the filaments can also be distributed more optimally, which means for example they can be placed closer together or can create a desirable pattern on the expandable basket. Another advantage of the expandable basket made of the braided mesh is the higher mechanical stability of the structure that can ensure stable and predictable distances between electrodes.

The braided mesh may be heat-treated which may ensure deformations and fixation of such deformations of the filaments. Such deformed filaments then ensure that during expansion and collapse of the basket assembly (expandable basket) the crossing points of the filaments (points, where the filaments intersect each other) stays relatively stable regarding a filament length. It means the filament crossing points stay at the relatively same filament length distances in the collapsed state as well as in all expanded states of the basket assembly (expandable basket). What is changing is a mutual angle of the particular filaments creating the crossing points (for example from about 2 degrees up to 178 degrees or vice versa). Some kind of minor lengthwise movement of the crossing points may not be completely avoided by this process, however it stays in limits where it doesn't compromise dimensional and/or mechanical stability of the braided mesh. This feature may then for example allow placement of the electrodes in the crossing points of the filaments and/or ensure stabile, predictable desired mutual positions of electrodes and/or their mutual distances.

Figure 20:
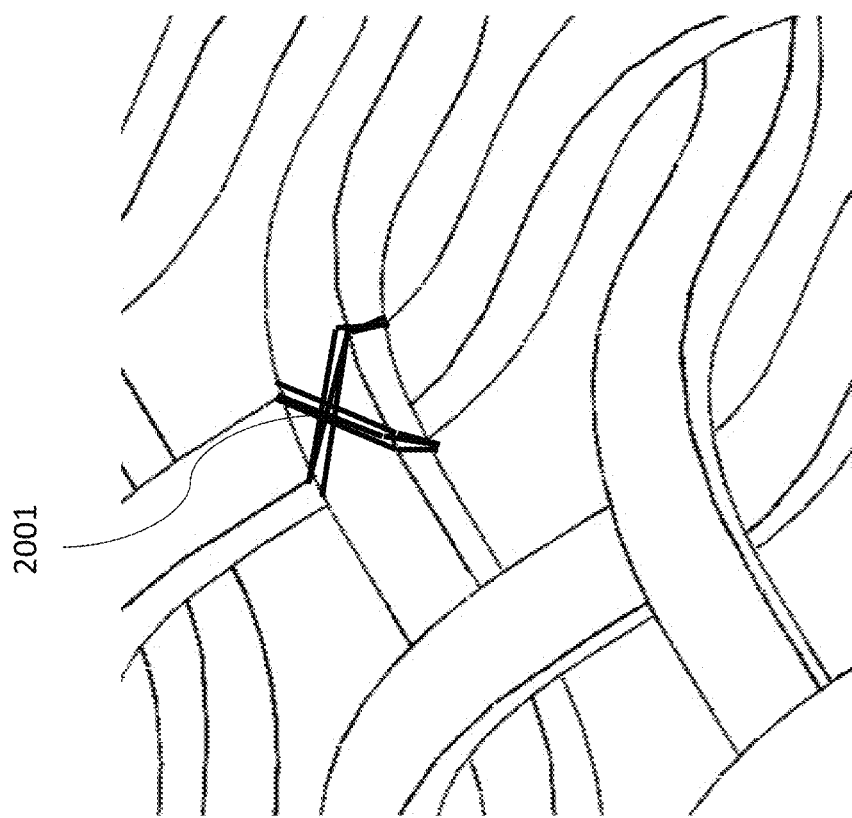
FIG. 20 shows an example of filaments joined together at their crossing point.

Even further structure stability of the expandable basket, made out of the braided mesh, may be achieved for example by joining of the particular filaments (included in the braided mesh) together. The filaments may be for example joined together at their mutual crossing points. An exemplary solution may be seen in FIG. 20. The joints (2001) may be fixed (not allowing any mutual movement of the filaments in the joining point) or interacting (some kind of mutual movement of the filaments in the joining point is possible). The joining may be achieved for example by gluing, welding, lamination, bonding, tying (for example with some kind of string) or melting. Another option could be tying the filaments together for example by a ring structure or by crimping. In case the ring structure is made out of conducting material (for example metal), it can serve also as an electrode. The same is true for the crimping. The metal connector may serve as an electrode as well.

Figure 22:
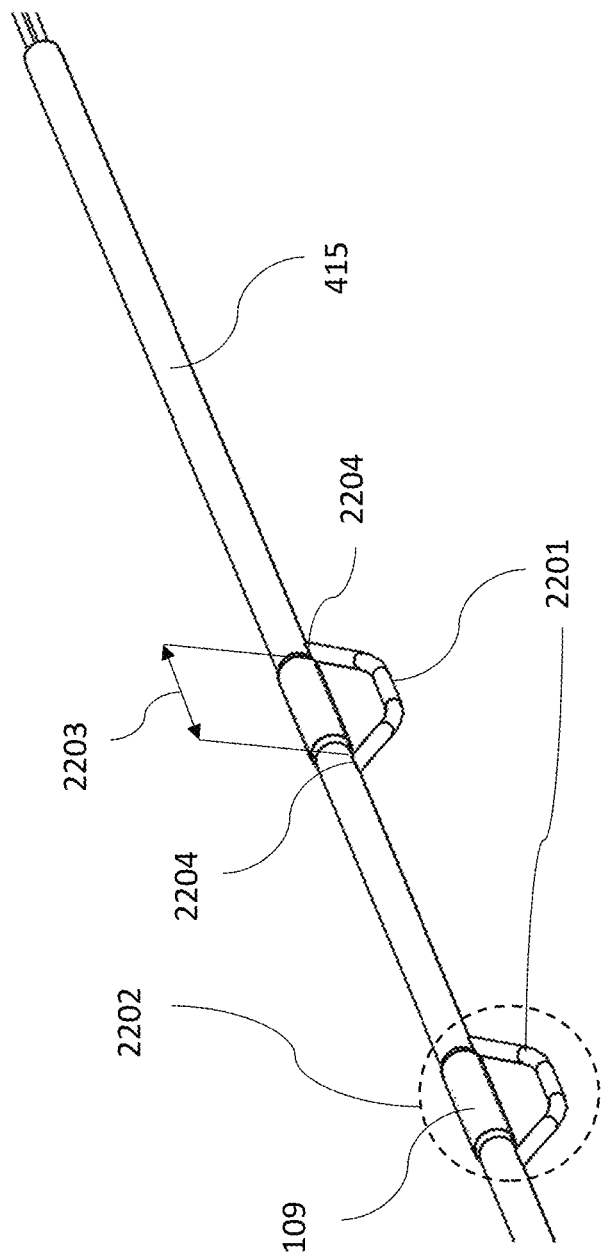
FIG. 22 shows an example of a filament made by a molding process.

Structures adapted for joining of two filaments may already be included on the filament even before braiding. In an example where at least one filament (415) is made by a molding process for example an injection molding process, the filament (415) may include at least one area where it will be split and/or an at least one area where an additional loop (2201) on the filament will be created during a molding process as can be seen in FIG. 22 and FIG. 23. Such at least one split area and/or additional loop (2201) may be for example created at or adjacent to at least one filament crossing point area (2202), which is an area of the filament which intersects with another filament in the crossing point (2301) in the braided mesh. The split or loop (2201) on the first filament (415) included in the crossing point (2301) may be adapted for insertion of the second filament (415) included in the crossing point (2301), thus serving to help to join (fix) the two filaments (415) together in the crossing point (2301). Such a crossing point (2301) where the filaments (415) are fixed by a loop (2201) or a split may have similar properties as, for example, a crossing point joined by tying with string, but without the need of the tying step.

In an example when the first filament included in a crossing point comprises a loop at and/or adjacent to a crossing point area participating in this crossing point, the second filament included in the crossing point does not comprise a loop at and/or adjacent to the crossing point area participating in this particular crossing point, which means there may be maximally one loop in any crossing point. The length of the loop at and/or adjacent to a crossing point area on a first filament in a crossing point (length from the first connection point with the filament to the second connection point with the filament) may be selected according to the diameter of the second filament included in the crossing point (the other filament has to fit into the loop, but the loop should not be too loose around the other filament) and may be for example from 0.5 mm to 10 mm, or from 1 mm to 7 mm, or from 2 mm to 5 mm. The cross-sectional diameter of the loop may be for example from 0.1 mm to 1 mm, or from 0.15 mm to 0.7 mm or from 0.2 mm to 0.5 mm.

All of the crossing points included in the expandable basket may be joined or only portion of the crossing points may be joined and the rest of the crossing points may be not joined.

In another example, the expandable basket may be made by a molding process, for example by an injection molding process. The mesh of the expandable basket may not be braided in this example, but can be made out of a molded structure. There may be several options for how to make an expandable basket by molding.

Figure 24B:
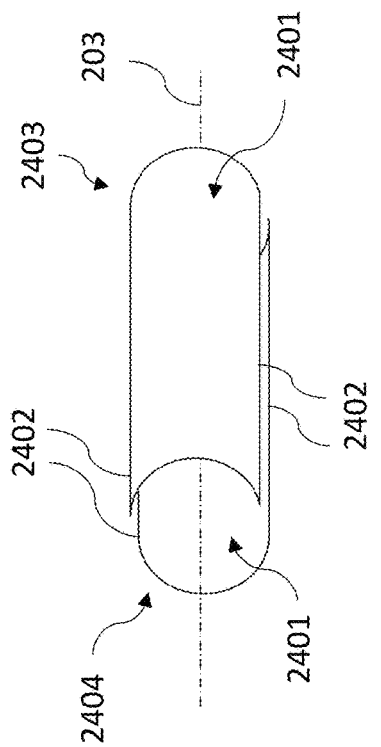
FIG. 24b shows a planar molded braided mesh bent into a shape of a tube.
Figure 24C:
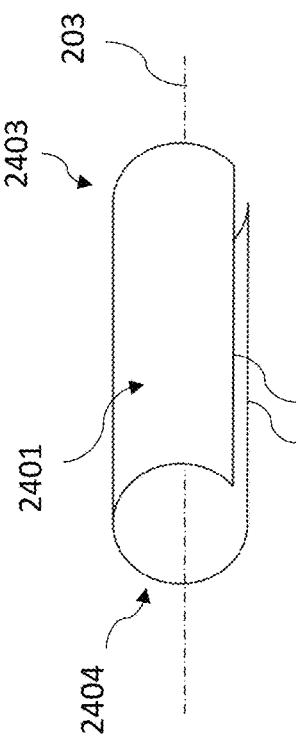
FIG. 24c shows a plurality of planar molded meshes bent into a shape of a tube.
Figure 24A:
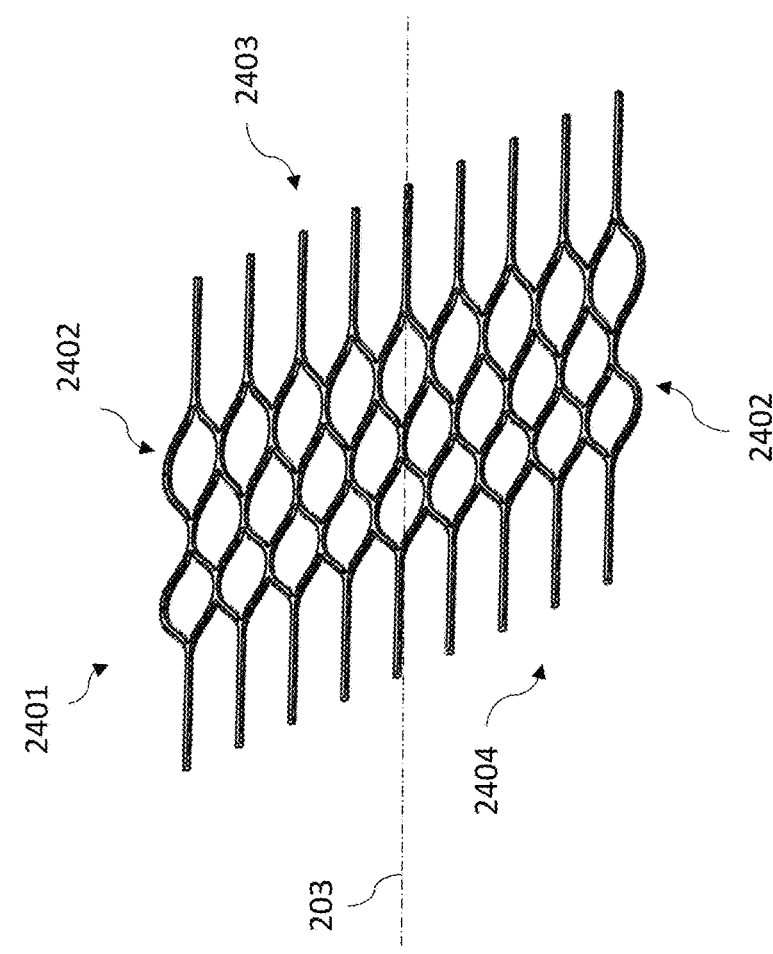
FIG. 24a is an example of a planar braided mesh made by a molding process.

The expandable basket may be for example made by at least one molded mesh in a form of a two-dimensional (flat, planar) structure (planar molded mesh) (2401) as shown in FIG. 24a. The at least one planar molded mesh (2401) is configured to be shaped into a three-dimensional shape after the molding. The at least one planar molded mesh may be taken out from the mold after the molding and may be bent for example around a central longitudinal axis (203), for example into a shape of a tube as shown in FIG. 24b. FIG. 24c is an example where more than one planar molded mesh is used to create an expandable basket. Each of the molded meshes (2401) may be in this example bent into a shape creating only a portion of the intended tube (portion of circumference of the intended tube) on its own, and creating a complete tube when brought together. Edges (2402) of the molded meshes would be then coupled together (for example by welding, crimping, gluing, tying . . . ) to create a tubular structure. After that, a distal portion (2403) of the tubular structure may be brought and coupled together and possibly fixed to a distal part of an inner elongated shaft thus creating a terminal assembly hence an expandable basket. Proximal portion (2404) of the tubular structure may be coupled to the distal end of the outer elongated shaft.

In another example the expandable basket could be made out of a molded mesh molded already as a three-dimensional structure. FIG. 25a shows an example of such a structure which may be for example a tubular molded mesh structure (2501). In this example the step of bending a two-dimensional flat molded mesh could be omitted, while the tubular molded mesh structure would be already made in the mold. The further steps would be similar to the previous example. A distal portion (2403) of the tubular molded mesh structure (2501) may be brought and coupled together and possibly fixed to a distal part of an inner elongated shaft thus creating a terminal assembly hence an expandable basket. Proximal portion (2404) of the tubular molded mesh structure (2501) may be coupled to a distal end of the outer elongated shaft.

In a further example which may be seen in FIG. 25b, the expandable basket (409) may be molded in one single step.

In this particular example the expandable basket is made directly by the molding process with a distal part (2502) of the expandable basket already molded together thus creating at least part of the terminal assembly in a single step with molding of the rest of the expandable basket. The molded distal part (2502) of the expandable basket (409) may be than coupled to the distal end of the inner elongated shaft, the proximal part (2503) may be coupled to the distal end of the outer elongated shaft.

The molded mesh molded as a three-dimensional structure may have shapes other than a tubular shape. It may be for example molded in a shape of an expandable basket in one of the expanded states.

The molded mesh molded as a three-dimensional structure does not have to be molded as a complete structure, however it is possible to mold several three-dimensional parts of the molded mesh and then couple those parts together. The three-dimensional parts may for example create only a portion of the intended structure (for example a portion of a circumference of a tube or a basket in one of its expanded states) on its own, and creating the complete structure when brought and joined together.

In the examples of the expandable basket made out of molded mesh, electrodes, conductive wires and/or other structures (for example tubes for creating lumens, reinforcement struts and so on) may be placed in the mold prior to molding and could be overmolded during the molding of the molded mesh. The structures could be overmolded completely, which means they would be completely inside of the molded mesh not reaching a surface of the molded mesh, and/or partially, for example when at least part of their surface would be exposed on the surface of the molded mesh. For example the electrodes may be overmolded partially when at least part of their surface is exposed on the surface of the molded mesh. The structures however doesn't have to be overmolded and at least part of them may be added to the molded mesh after the molding process of the molded mesh.

The molded mesh may be for example made out of polymers or thermoplastic elastomers like Nylon, Fluorinated ethylene propylene (FEP), Polyethylene (PE), PEBA, PEEK, Polyimide (PI), Polypropylene (PP), PTFE, Polyurethane (PU), Polyethylene terephthalate (PET) or for example Silicon.

Particular openings (meshes, interstices) within the braided or molded mesh do not need have to have uniform size, on the contrary, the sizes of particular openings may differ. The sizes may for example increase from the distal portion and the proximal portion of the expandable basket (where they may be smallest) in the direction toward the middle part of the expandable basket, where they may be the largest. In other words, the dimensions of the openings in the central body portion of the basket assembly may be larger than the dimensions of openings in the proximal and distal body portions of the basket assembly. The dimensions may for example increase linearly or exponentially. The circumference of the openings in the proximal and distal body portions may be for example between 1 mm to 40 mm, while the circumference of the openings in the central body portion may be for example between 5 mm to 80 mm. The number of rows of the openings, creating a complete braided or molded mesh of the expandable basket may be between 4 to 40.

The ratio of the circumference of the smallest opening to the circumference of the largest opening in the expandable basket may be from 100:101 to 1:80, or from 20:21 to 1:50, or from 10:11 to 1:40. The number of rows of the openings may be counted from a first complete opening from an attachment of the proximal portion of the expandable basket adjacent to the distal end of the outer elongated shaft up to the last opening in distal portion of the basket assembly terminated by terminal assembly. Overall number of the openings included in the braided or molded mesh creating the expandable basket (overall number of openings in the expandable basket) may be from 12 to 1000, or from 16 to 500, or from 24 to 259 or from 32 to 128.

Figure 21:
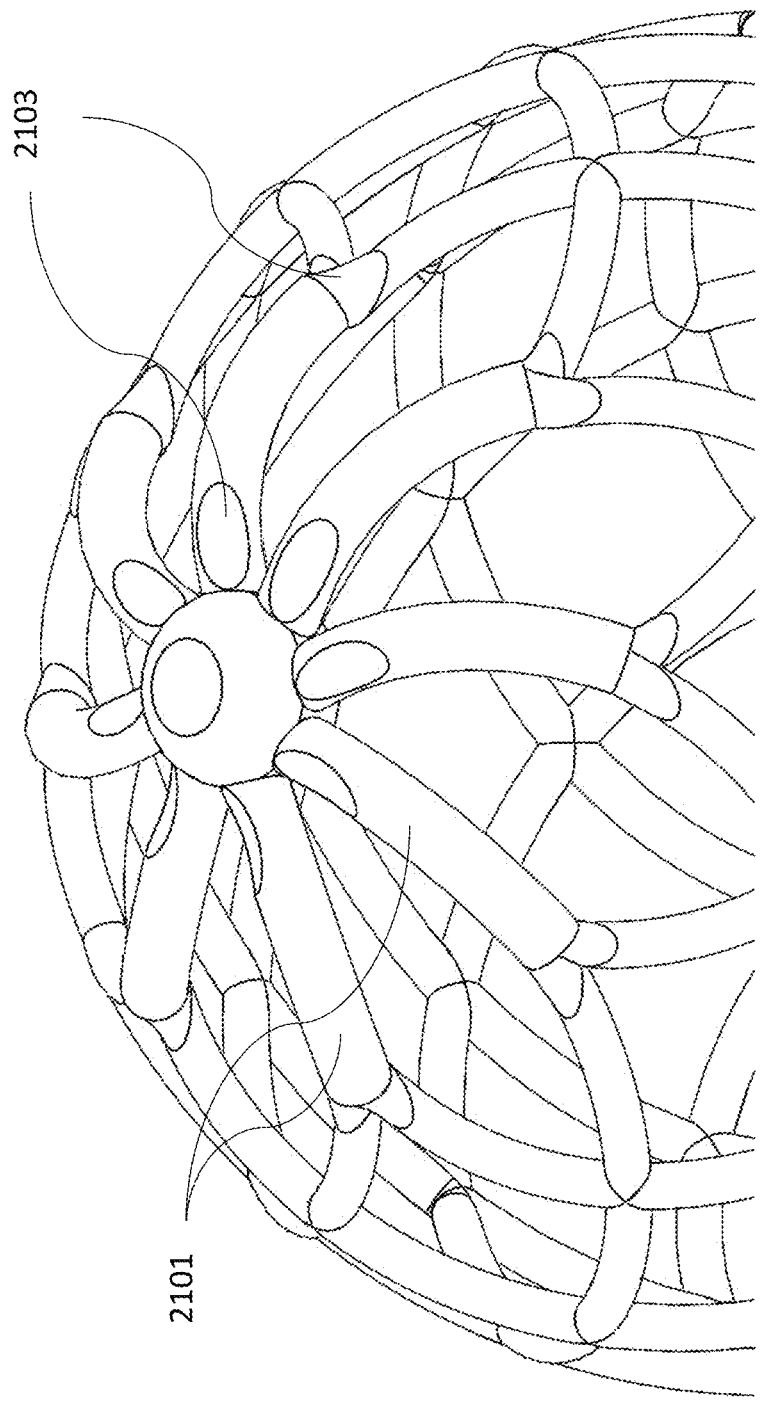
FIG. 21 is a view of a distal part of the basket assembly with merged structures and living hinges.

Two or more filaments creating a braided or molded mesh and hence expandable basket may be merged or joined together at their proximal and/or distal ends to create a merged structure (2101) in the proximal and/or distal portion of the expandable basket as shown schematically in FIG. 21. Such a solution may reduce a number of filaments at the proximal and/or distal portion of the expandable basket. Lowering a number of filaments entering related structures like the basket assembly proximal portion which may include an attachment of the proximal portion of the expandable basket adjacent to the distal end of the outer elongated shaft, and/or the distal portion of the basket assembly which may include a terminal assembly may reduce a complexity and/or enhance mechanical stability of those structures hence of the whole basket assembly. It may even help to reduce risk of an ablation procedure, due to a reduction of the number of members in the structures with reduced number of filaments. In terms of the filament length the merged structure in proximal or distal part of the filament may occupy from 1% to 30% or from 3% to 20% or from 5% to 15% of the total length of the filament included in the expandable basket. As stated before, the filaments may be merged in distal or proximal ends of the filaments or in both. In the case where the filaments are merged in both ends, the merged length may be the same on both ends, or it may differ. Relative to the length of the expandable basket in its collapsed configuration, the merged part of the filaments, either on proximal or distal end of the basket, may occupy from 1% to 35% or from 4% to 25% or from 6% to 20% of the length of the collapsed basket. The filaments may be merged for example by gluing, welding, lamination, bonding, tying or melting. Another option could be joining the filaments together for example by some kind of tubular structure or by crimping. The tubular structure may be for example a tube made of metal or polymer or thermoplastic with lumen. In this case the end parts of the filaments would be put through the lumen of the tube, fixed there (for example by gluing, welding, lamination, bonding, tying, melting or swaging) and so joined together. Another option could be usage of a multi-lumen tube, made of metal or polymer or thermoplastic, where each end part of each filament to be joined would be put through a separate (its own) lumen of the multi-lumen tube, fixed there (for example by gluing, welding, lamination, bonding, tying, melting or swaging) and so joined together.

Figure 26:
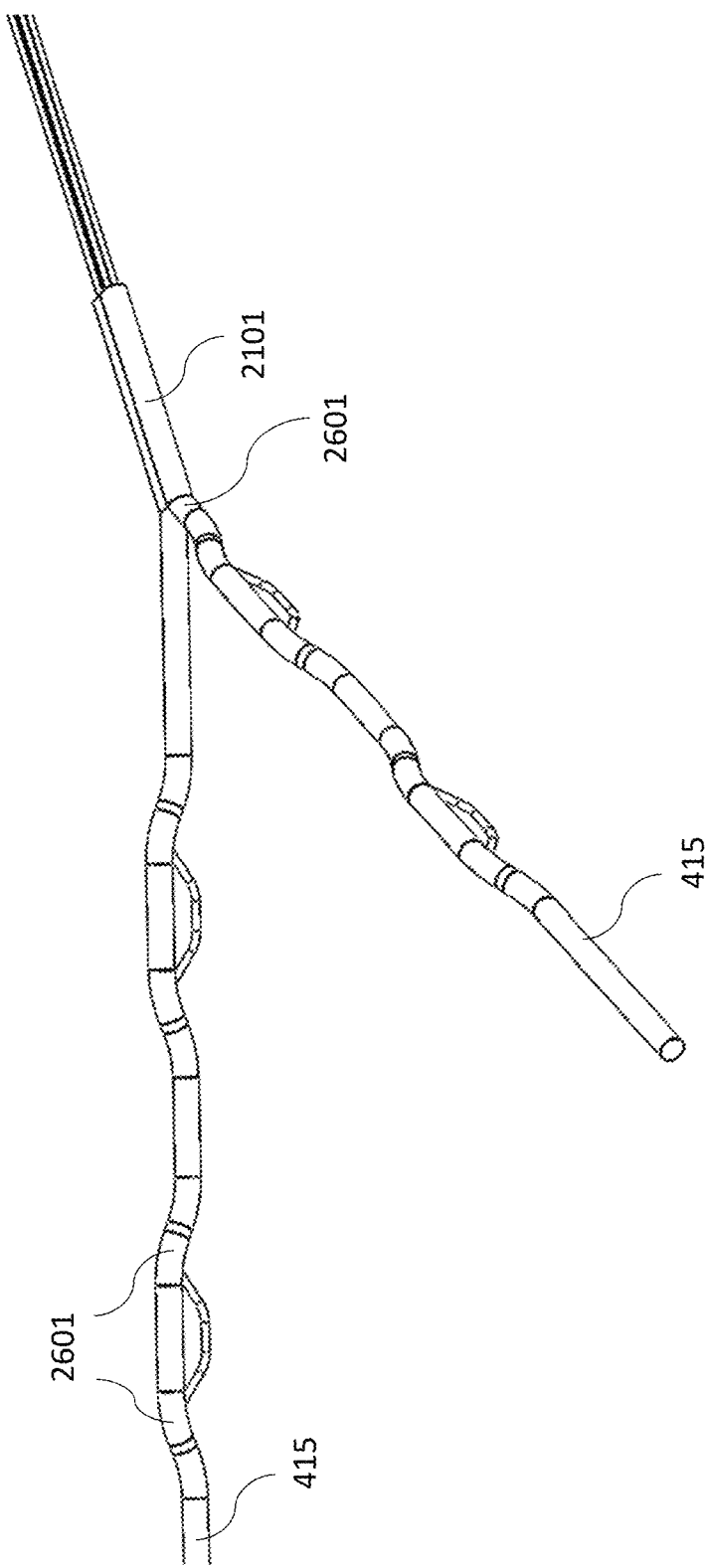
FIG. 26 shows two filaments made by molding to create a merged structure.

In an example with filaments (415) made by molding process, for example injection molding, at least two filaments (415) may be molded as a single filament, braided into a braided mesh and then they may be merged together at their proximal and/or distal ends to create a merged structure (2101). However the at least two filaments (415) may be molded at once in a way, that at least one of the merged structures (2101) (either a proximal or a distal) may be already created during the molding process. An example of filaments (415) and a merged structure (2101) made by a molding process may be seen in FIG. 26. The filaments (415) including the already molded merged structure (2101) then may be braided into a braided mesh and at least one step of merging of the filaments after the braiding may be avoided. The ends of the filaments (415) not merged already from the molding process may be merged together and/or merged with other different filaments after the braiding process.

The filaments may be made out of electrically insulating, nonconductive material, for example polymers or thermoplastic elastomers like Nylon, Fluorinated ethylene propylene (FEP), Polyethylene (PE), PEBA, PEEK, Polyimide (PI), Polypropylene (PP), PTFE, Polyurethane (PU), Polyethylene terephthalate (PET) or for example Silicon. The material may be further reinforced for example by glass fibers. The cross-section of the filament may be circular, or alternatively other cross-section shapes are possible, for example but not limited to oval, round, semicircular, rectangular, square, flat, or star-shaped. The filaments (415) may be for instance formed of tubes with at least partially hollow structures with lumen (601) as can be seen on FIG. 6B. Some or all of the filaments (415) can be hollow along their entire length or for example the lumen (601) may be present only in a portion of the length of one or more filaments (415). Another aspect may include a braided mesh (413) comprising a first subset of the filaments (415) including lumens (601) and another subset of the filaments (415) without lumens, or all of the filaments may be without lumen.

Figure 27:
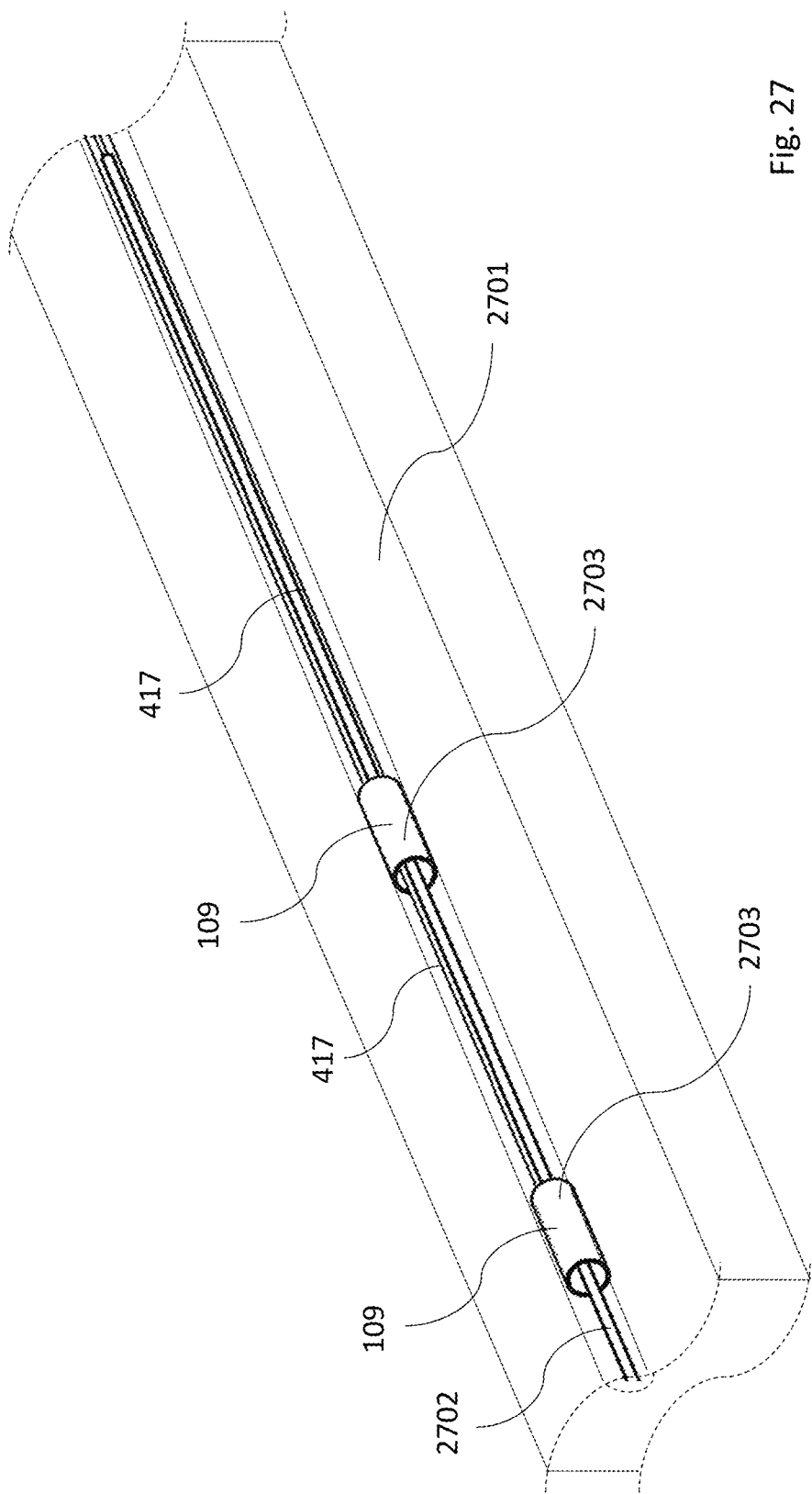
FIG. 27 shows an exemplary placement of components in a mold configured for injection molding of a filament.

In another example the filaments may be made by a molding process, for example by an injection molding process. Electrodes (109), conductive wires (417) for example connected to the electrodes (109) and/or other components (for example tubes for creating lumens, reinforcement struts (2702), other wires and so on) may already be placed in the mold (2701) before molding and could be overmolded during the molding of the filament as shown in FIG. 27. The components could be overmolded completely, which means they would be completely inside of the molded filament not reaching a surface of the filament (not to be exposed on the surface of the filament), and/or partially, for example when at least part of their surface would be exposed on the surface of the filament. For example the electrodes may be overmolded partially when at least part of their surface is exposed on the surface of the molded filament. The structures however doesn't have to be overmolded and at least part of them may be added to the filament hence the braided mesh later on, after the molding process of the filament.

The filaments made out of electrically insulated tubes with hollow structures (cavities) may have disadvantages, for example when electrodes, for example in the form of tubes are placed on the filaments and wires, coupled to the electrodes are lead inside of the lumen of the filament. A small opening in the wall of the filament usually serves for the transition of the wire through the wall of the filament. This small opening needs to be sealed to prevent for example blood or other liquid reaching the inside of the filament. In case the electrode is a ring-shaped electrode placed around the filament, the sealing may be between the filament and the electrode. Usually such a seal is done by glue placed in the area between edges of the electrodes and the filament on which the electrode is placed. The glue ensures a sealing between the electrode and the filament. Another advantage of such a solution is the glue on the edge of the electrode adds a stiffness to the filament directly next to electrode, which ensures that in case the filament needs to bend in the area where the electrode is placed, the bending of the filament happens further away from the edge of the electrode, preventing exposure of the edge of the electrode. The electrode could have a sharp edge and exposing such a sharp edge could for example cause harm to the patient. A disadvantage of a solution with ring shaped electrodes placed on the tubular filaments and sealed with glue is the seal adds an additional material, which means the diameter of the filament in the place where the glue is applied on the filament increases, which can be a problem for a catheter with a high number of filaments. Another problem of the solution with applied glue to seal the electrode from the filament is the glue could potentially strip, which can cause a portion of the glue to get loose and potentially harm the patient. The issues may be solved for example by the filaments made by a molding process or for example by filaments in a further example.

In another example the filaments (415) may take the form of at least partially hollow structures, for example including tubes made out of non-conducting material, for example a thermoplastic. Exemplary cross sections of such filaments (415) may be seen in FIGS. 31a to 31c. The filaments (415) including electrodes (109), for example ring-shaped electrodes may include at least two tubes (3100), which may be coupled to each other in a place where the electrode (109) is placed on the filament (415). The tubes (3100) may be made of material with a melting point, for example with a melting point which is lower than a melting point of other structures in the filament, for example a thermoplastic. The coupling of the tubes may include a melted material (3101), which may come for example from at least one of the tubes (3100). The melted material (3101) may fill a lumen of the electrode (109) and seal the electrode and/or a conductive wire (417) coupled to the electrode, or another structure leading to the electrode (109) from the lumen of the filament or any other structure leading into the lumen of the filament and may ensure a connection of the tubes to each other. The filament may include a cord (3102) which may be longitudinally placed inside of the lumen of the filament and may lead uninterrupted at least in an area where the electrode (109) is placed on the filament (415), hence where the tubes (3100) are coupled to each other. The cord (3102) may serve as a reinforcement for the filament.

A manufacturing process of the filament including at least two tubes as described in the previous paragraph may include steps shown in FIGS. 31a to 31c. In the first step, shown in FIG. 31a, the tubes (3100) and the electrode (109) are put on the cord (3102) in such a way that the electrode (109) is placed between the tubes thus creating an assembly. The conductive wire (417) coupled to the electrode (109) is leading into a lumen of one of the tubes (3100). In a next step is the whole assembly is heated up at least to a melting temperature of the material from which the tubes (3100) are made. The tubes (3100) melt and the melted material from ends of the tubes adjacent to electrode flows into the lumen of the electrode and fills it up. In the following step the assembly is cooled down to a temperature at least below the melting temperature of the material from which the tubes (3100) are made. The result of this step may be seen in FIG. 31b and/or 31c.

The exemplary filaments (415) shown in FIGS. 31a to 31c may include other structures, particularly at least one ring (3103). The ring may be out of a different material than the tubes (3100), particularly the melting point of the material of the ring (3103) may be higher than a melting point of the material of the tubes (3100) and the deflection point of the material of the ring (3103) may be approximately the same as the melting point of the material of the tubes (3100). The ring may be positioned on the tube, particularly on the end of the tubes adjacent to the electrode (109). It may serve as an additional sealing element, surface smoothing element and reinforcement element in a transition between an edge of the electrode (107) and the tube (3001). It may prevent an overflow of the material of the tubes over the electrode during the manufacturing process. The ring may also help with a bending point of the filament. In case the filament is bent, it may help with moving the bending point with a sharpest angle away from the electrode, which may be beneficial for example for preventing exposure of a sharp edge of the electrode. The length L of the ring may be from 0.1 mm to 10 mm or from 0.2 mm to 5 mm or from 0.5 mm to 4 mm or from 0.7 to 2.5 mm. The filament may include one ring adjacent to one side of the electrode, or it may include at least two rings for example adjacent to both sides of the electrode.

The inner diameter of the ring (3103) before the manufacturing process may be the same or higher than the outer diameter of the tubes (3100) which they have before the manufacturing process. In the first step of the manufacturing process the ring (3103) may be put on the tube (3100), particularly on the end of the tube adjacent to the electrode (109) as shown in FIG. 31*a* and the tubes (3100) with the electrode (109) are put on the cord (3102) in a way in which the electrode (109) is placed between the tubes (3100) with rings (3103) thus creating an assembly. In a next step the whole assembly is heated up at least to a melting temperature of the material from which the tubes (3100) are made and a deflection temperature of the material from which the ring (3103) is made. The tubes (3100) melt and the melted material from the ends of the tubes adjacent to electrode flows into the lumen of the electrode and fills it up, while the ring (3103) shrinks. The softened ring (3103) should shrink until its outer diameter reaches the same size as the outer diameter of the electrode (109), or between the same size of the outer diameter of the electrode (109) and the outer diameter of the electrode (109) minus 10%, or between the outer diameter of the electrode (109) minus 0.1% and the outer diameter of the electrode (109) minus 7%, or between the outer diameter of the electrode (109) minus 0.2% and the outer diameter of the electrode (109) minus 5%. Such shrinkage amount may prevent material from which the ring (3103) is made to melt over the electrode in a following step, which could lead to potential insulation issues or peeling of such a melted material over the electrode during use. The result of the step may be seen in FIG. 31*b*. In a following step the assembly is heated further up to a melting temperature of the material from which the ring (3103) is made. The material of the ring (3103) melts and bonds itself with the material of the tube (3100) as shown in FIG. 31*c*. In the following step the assembly is cooled down at least under the melting temperature of the material from which the tubes (3100) are made.

Due to shrinking of the melted material of the tubes (3100) and due to some of the material of the tubes filling the inner lumen of the electrodes during the manufacturing process, the outer diameter of the tubes (3100) before the manufacturing process may be higher than the outer diameter of the electrodes. It may be higher for example by 1% to 60%, or from 3% to 50% or from 5% to 40% or from 10% to 35%. The material of the tubes (3100) and the ring (3103) may be for example thermoplastic with two different melting temperatures, for example Nylon. The materials may be chosen in a way that the melting point of the material of the ring (3103) may be higher than melting point of the material of the tubes (3100) and the deflection point of the material of the ring (3103) may be approximately the same as the melting point of the material of the tubes (3100).

The diameter of the filaments of the braided or molded mesh may be from 0.2 mm to 1 mm or from 0.4 mm to 0.8 mm or from 0.5 mm to 0.7 mm. The number of the filaments braided into the braided mesh creating an expandable basket can vary from 5 to 150 or from 10 to 60 or from 15 to 50 or from 16 to 32. The filament made by the molding process may have some specific aspects. For example the diameter of the filament does not have to be uniform through its whole length, but may vary along its length. For example, the filament may have a different (for example reduced) diameter in at least one crossing point area compared to the rest of the filament. In a particular example of a crossing point of two filaments, at least one of the filaments creating this crossing point may have a reduced diameter and/or a cross section area at and/or adjacent to the crossing point area participating in this crossing point. In an example when the diameter of the filament is reduced in a specific area it may be reduced for example by amount of 0.1% to 90%, or by 0.5% to 75% or by 1% to 60% compared to the unreduced filament diameter. In an example when the cross section area is reduced in a specific area, it may be reduced by amount of 0.1% to 90%, or by 0.5% to 75% or by 1% to 60% compared to the unreduced cross section area.

A reduction of the filament at and/or adjacent to a crossing point area may help to mechanically stabilize the braided mesh, and hence the expandable basket by providing more stable crossing points and/or to reduce a maximal diameter of the collapsed expandable basket. A filament with a reduced diameter at and/or adjacent to the crossing point area may ensure that during expansion and collapse of the basket assembly (expandable basket) the crossing points of the filaments stay relatively stable regarding a filament length. It means the filament crossing points stay at relatively the same filament length distances in the collapsed state as well as in all expanded states of the basket assembly (expandable basket). What is changing is a mutual angle of the particular filaments creating the crossing points (for example from about 2 degrees up to 178 degrees or vice versa). Some kind of minor lengthwise movement of the crossing points may not be completely avoided, however it stays within limits where it doesn't compromise dimensional and/or mechanical stability of the braided mesh. This feature may then for example allow placement of the electrodes in the crossing points of the filaments and/or ensure stable, predictable desired mutual positions of electrodes and/or their mutual distances.

In another aspect the filament, made by molding process may have a variable cross-section shape. It may be advantageous for example in crossing points of the filaments, where different cross-section shapes of at least one of the filaments included in the crossing point may help stabilize the crossing point and/or may help to reduce the maximal diameter of the expandable basket in its collapsed configuration. The cross-section shape used at and/or adjacent to the crossing point area of the filament included in a filament crossing point may be for example semicircular, rectangular, flat, elliptical or for example oval, while the cross-section of the rest of the filament may be different, for example circular. In a case where the cross section of the filament at and/or adjacent to a crossing point area includes a flat or flattened side, the flat or flattened side may be the one in contact with the other filament creating the crossing point.

A combination of variable cross section and variable diameter of the filament is also possible. For example the filament may have a different cross section and different (for example reduced) diameter at and/or adjacent to the crossing point area, which may again help with the braided mesh and hence the expandable basket stabilization and reduction of the maximal diameter of the expandable basket in the collapsed configuration. The maximal diameter of the expandable basket in the collapsed configuration may be for example reduced by 0.01% to 50%, or by 0.05% to 30%, or by 0.1% to 15%.

The variable diameter and/or the variable cross section may not be used only at and/or adjacent to the filament crossing point areas, but in different areas of the filaments as well. For example the diameter reduction and/or the cross-section change may allow for the creation of weaker and/or more rigid areas on the filament for example creating a living hinge during a process of filament molding.

In another example the molded filament does not have to be molded straight, but it may be already made with at least one bend or a curvature (2601). The bend and/or the curvature (2601) may be located for example at and/or adjacent to at least one crossing point area of the filament or for example adjacent to a proximal or a distal end of the filament. An example of such a solution may be seen in FIG. 26. The pre shaped curvatures (2601) may serve for example for further stabilization of the braided mesh, hence the expandable basket. The filaments may be pre-shaped in such way that the thermal stabilization after the braiding of the braided mesh may not be necessary.

In a further aspect the filament may be molded including at least one area where it would be split and/or an at least one area where an additional loop (2201) on the filament (415) would be created during a molding process. Such at least one split area and/or additional loop (2201) may be for example created at and/or adjacent to at least one filament crossing point area (2202) and may serve for example as a support (fixation) in at least one crossing point of two filaments (415) after the filaments (415) are braided into a braided mesh. In a further example a filament may include an electrode inside a split (e.g. inside an area bounded by a beginning and by an end of the filament split) and/or inside a filament loop area (2203) bounded by the first connection point (2204) of the loop (2201) with the filament (415) and the second connection point (2204) of the loop (2201) with the filament (415), which may be seen in FIG. 22.

A crossing point area of the filament is an area on the filament, which takes part in a crossing point in the braided mesh structure. In some instances at least one electrode may be placed at and/or adjacent to the crossing point area on the filament. In a case where the electrode is placed at and/or adjacent to the crossing point area of the first filament included in a particular crossing point, the second filament included in this crossing point may not include an electrode at and/or adjacent to the crossing point area of this particular crossing point. It means there may be a maximum of one electrode at any crossing point of the braided mesh and hence the expandable basket. In a further aspect in case the crossing point includes an electrode, it may be included at and/or adjacent to a crossing point area of a filament which is in further lateral distance from the longitudinal axis in this particular crossing point, which means the electrode is placed on the outer perimeter of the expandable basket.

In an example with a molded filament, such a molded filament may have a different diameter and/or cross section in at least one crossing point area than in the rest of the filament as already described. In one particular example, in case the electrode is included in the crossing point, the first filament including the electrode may have a cross section corresponding to a cross section of the electrode in the crossing point area (for example a circular cross section) and may include a loop at or adjacent to the crossing point area, the second filament in this crossing point may have for example a reduced diameter and/or different cross section than the rest of the filament (for example it may have a flat, rectangular, oval or semicircular cross section in the crossing point area and a circular cross section in another areas).

However it does not mean the filament comprising an electrode at or adjacent to a crossing point area cannot have a different diameter or different cross section in the crossing point area than the rest of the filament. For example the electrode included on the filament may have a different diameter or different cross section than the rest of the filament.

There are further options to enhance a mechanical stability of the filaments. A use of a multilayer wall may be one of them. The wall of the filament may include for example more than one layer of material. Materials of different properties may be used, which in combination may result in more mechanically stable wall thus more mechanically stable filament. Such a combination may use layers made each one from different material from a group of polymers or thermoplastics, for example from Nylon, Fluorinated ethylene propylene (FEP), Polyethylene (PE), PEBA, PEEK, Polyimide (PI), Polypropylene (PP), PTFE, Polyurethane (PU), Polyethylene terephthalate (PET) or for example Silicon. Another possible option may be usage of layers from the same kind of material, but different subgroups of the materials with different properties for each layer. Materials used in the particular layers may be further reinforced for example by glass fibers.

In another aspect, the filaments may be for example further mechanically reinforced by insertion of a mechanical support into a lumen of a filament. Such a mechanical support may be for example in form of struts placed in the filament lumen. The struts may be placed into the full length of the filament, or in a full length of filament lumen, in the case that the filament does not have a lumen in its entire length. Another possible option would be to place the struts into only a portion of length of the lumen, thus leaving part of the filament reinforced with a strut and another part without a strut reinforcement. The struts may be for example made of nitinol, for example with electrical insulation layer, for example from Polyamide (PA), Polyimide (PI) or PTFE. Other possible materials suitable for struts may be polymers or thermoplastics, for example from Nylon, Fluorinated ethylene propylene (FEP), Polyethylene (PE), PEBA, PEEK, Polyimide (PI), Polypropylene (PP), PTFE, Polyurethane (PU), Polyethylene terephthalate (PET) or for example Silicon.

In an example with a molded filament at least one reinforcement strut (2702) may be placed in a mold (2701) and may be overmolded. In this example the strut (2702) has to be made out of a material with a higher melting point than the filament. The at least one strut (2702) may be again placed into the full length of the filament or in only a portion of the filament length, thus leaving part of the filament reinforced with a strut and another part without a strut reinforcement. An example of strut placed already in the mold may be seen in FIG. 27.

Yet another option suitable for further reinforcement of the filaments is to fill at least part of the lumen of the filament by glue or melted polymer or thermoplastic material.

A braided mesh then may be constructed in a way that all of the filaments included in the braided mesh may be reinforced or only a portion of the filaments included in the braided mesh may comprise a reinforcement and another portion of the filaments may be without it.

At least one of the filaments creating a braided mesh may include at least one place where the structure of the filament is locally mechanically weaker than rest of the filament. Such a place may create so called living hinge (2103), schematically shown in FIG. 21. The living hinges may be useful for defining more or less exact places, where filaments included in the braided mesh, and hence in the expandable basket bend easier and where the bends on the filaments create smaller radiuses (or directly kinks) in comparison with filaments without such a living hinge. This may further help in defining a more predictable shape of the deployed expandable basket in at least one of its deployed positions. Establishment of such a living hinge on the filament may include thinning or cutting of part of the filament. Thinning may be done for example by squeezing or thermoforming of a particular place of the filament. The thinning may be made around whole circumference of the filament, or only partially. Partial asymmetrical thinning may be advantageous, since such created hinge may define a particular direction in which the filament bends easier compared to other directions. In one example of the expandable basket, the living hinges created on the filaments may allow easier bending of the filaments, and hence the braided mesh, for example in a radial direction from longitudinal central axis of the catheter. For example living hinges creating smaller radiuses or kinks on the filaments in a distal body portion (421) of the basket assembly body or in an area of terminal assembly may help in the shaping of the expandable basket (basket assembly body) in an area located distally from a plane intersecting the basket assembly at the portion with the highest diameter (in one of its expanded configurations) in a way such that at least some of the distal part of the expandable basket (in an area of a distal body portion) may form larger angles (radially from elongated axis) compared to a proximal part of the basket (in an area of a proximal body portion). In extreme cases the distal part of the expandable basket (in an area of a distal body portion) may form an angle of 90° or more (radially from elongated axis) to achieve an expanded state where at least part of the expandable basket including electrodes becomes longitudinally the most distal part of the catheter, without any other part protruding more distally (for example terminal assembly). Such a configuration may be advantageous for example in an ablation of a relatively flat treatment site.

In an examples where the expandable basket is made out of a molded mesh or in examples where it includes filaments made by an molding process, the living hinges may be made directly during the molding of the molded mesh or the molded filament, for example by at least one of a reduction of a diameter of a part of a molded mesh or a filament, and by a cross-section change of a part of a molded mesh or a filament.

At least one living hinge as described in previous paragraphs may be included on at least one part of the braided mesh, where the filaments are merged together (on a merged structure). In this case the living hinge is a place on the merged structure, which is locally mechanically weaker then rest of the merged structure and may be created by thinning or cutting of the merged structure for example after merging. Another option to establish a living hinge on the merged structure, particularly in the case where the merged structure includes polymer tube and where the filaments are merged in the lumen of the tube or in the multiple lumens of multi-lumen tube, is to pre-thin or pre-cut the polymer tube before inserting the filaments. Such a pre-thinning of the tube may be done for example by squeezing, thermoforming or by molding, for example injection molding.

The living hinges may be created in an area of a distal body portion, central body portion and/or proximal body portion of the basket assembly body. They may be placed for example in a proximal area from 0% to 20% or 0% to 15% or 0% to 10% of the length of the collapsed basket in a case where they are in an area of a proximal body portion. They may be placed in a distal area from 0% to 20% or 0% to 15% or 0% to 10% of the length of the collapsed basket in a case where they are in an area of a distal body portion. They may be part of the terminal assembly as well. In a case where they are placed in the central body portion, the hinges may be placed on a plane intersecting the basket assembly in a portion with a highest diameter or from −20% to +20% or from −10% to +10% or from −5% to +5% distally from this plane or from the center of the collapsed basket.

The expandable basket may include one or more electrodes or a set of electrodes. The electrodes can be configured for at least one of generating an electric field for ablating tissue, or obtaining or sending electrical or other signals, for example signals for tissue mapping, ECG monitoring, impedance measurement and/or detection of contact with a tissue. Another function of the electrodes may be serving as markers for an X-ray. The electrodes may be coupled to particular filaments of the expandable basket. Electrodes can be placed on each of the filaments or only on some of the filaments. Each filament comprising the electrode may include one or more of the electrodes, for example from 1 to 15, or from 1 to 10, or from 1 to 6, or from 1 to 3 electrodes. The electrodes can be of one type or of different types. The overall number of electrodes placed on the expandable basket may be from 1 to 200, or from 5 to 100, or from 10 to 50, or from 15 to 40, or from 20 to 35. Spatial distances between electrodes in the fully expanded configuration of the expandable basket may be from 0.1 mm to 15 mm, or from 0.5 mm to 10 mm, or from 1 mm to 6 mm, or from 2 mm to 4 mm.

The electrodes may operate individually or in pairs or groups or a portion of the electrodes may be operated individually and portion may be operated in pairs or groups.

In an example, the electrodes may be placed in areas where the filaments cross each other (filaments crossing points). Such a position may be advantageous due to the ability to keep a more stable distance between electrodes during different configurations of an expandable basket and such a configuration may also advantageously prevent unwanted contact between electrodes, especially in cases where the expandable basket is not in a fully expanded configuration.

All of the electrodes included in the expandable basket may be positioned in the filaments crossing points, or only portion of the electrodes may be positioned in the filaments crossing points and portion of them may be positioned elsewhere.

Each filament may also include electrodes of one type or different types, or different filaments can accommodate different types of electrodes. Different types of electrodes may be understood as electrodes with different functions, for example ablation electrodes, measurement electrodes and so on, or physically different electrodes with for example different shape, size, design, materials and so on, or a combination of types of electrodes with different functionality and physical properties. For example, in configurations with ring-shaped electrodes placed on the filaments, all electrodes may have the same diameter and may differ in length, so there may be for example two or more groups of such electrodes, each group having different length. A number of electrodes in each of the groups may be the same or may differ. In an extreme example, each electrode on the expandable basket may have a different length. In configurations with ring-shaped electrodes, such electrodes may have a diameter between 0.2 mm to 3 mm, or from 0.4 mm to 2 mm, or from 0.5 mm to 1 mm, and may have a length between 0.1 mm to 10 mm, or from 0.2 mm to 8 mm, or from 0.3 mm to 6 mm, or from 0.4 mm to 4 mm.

In one example there may be a first group of 5 to 20 shorter electrodes, with lengths of for example 0.3 mm to 3 mm, and a second group of 5 to 30 electrodes which may be longer, for example with lengths from 0.6 mm to 4 mm. Advantageously the electrodes from the first group may be used for at least one type of measurement, for example for measurement of an intracardial ECG (EGM), or an ablation, and the electrodes from the second group may be used for an ablation, either independently or in combination with the electrodes from the first group.

The electrodes can be placed on the body of the basket assembly. For example, the electrodes may be placed on the central or distal body portion, in some cases the electrodes may be even placed on the proximal body portion. Other electrodes may be placed on or in an outer elongated shaft, inner elongated shaft, catheter distal tip or terminal assembly. In configurations where the electrodes are placed on the elongated shafts, distal tip or a terminal assembly and where ring-shaped electrodes are used, then they may have a diameter of 0.2 mm to 10 mm, or from 0.5 mm to 8 mm, or from 1 mm to 6 mm, or from 2 mm to 5 mm and may have a length between 0.1 mm to 20 mm, or from 0.2 mm to 15 mm, or from 0.3 mm to 12 mm, or from 0.4 mm to 10 mm.

The layout of the electrodes on the expandable basket may ensure continual, for example circular ablation areas while the expandable basket is in the expanded position and may create a pattern.

For instance, the layout of the electrodes on the expandable basket may ensure continual, circular ablation areas even while the expandable basket is held in various expanded positions between a fully collapsed and a fully expanded position and may create a pattern as well.

Additional electrodes, for example the ones placed on or in an outer elongated shaft, inner elongated shaft, catheter distal tip or terminal assembly may be part of the pattern or may be operated independently to other electrodes. For example, electrodes at the area of catheter distal tip or terminal assembly may be used for point-like ablation. There may be special dedicated electrodes at the area of distal tip or terminal assembly or for example metal parts of the terminal assembly may serve as an electrode, or combination of thereof may possible.

Figure 7A:
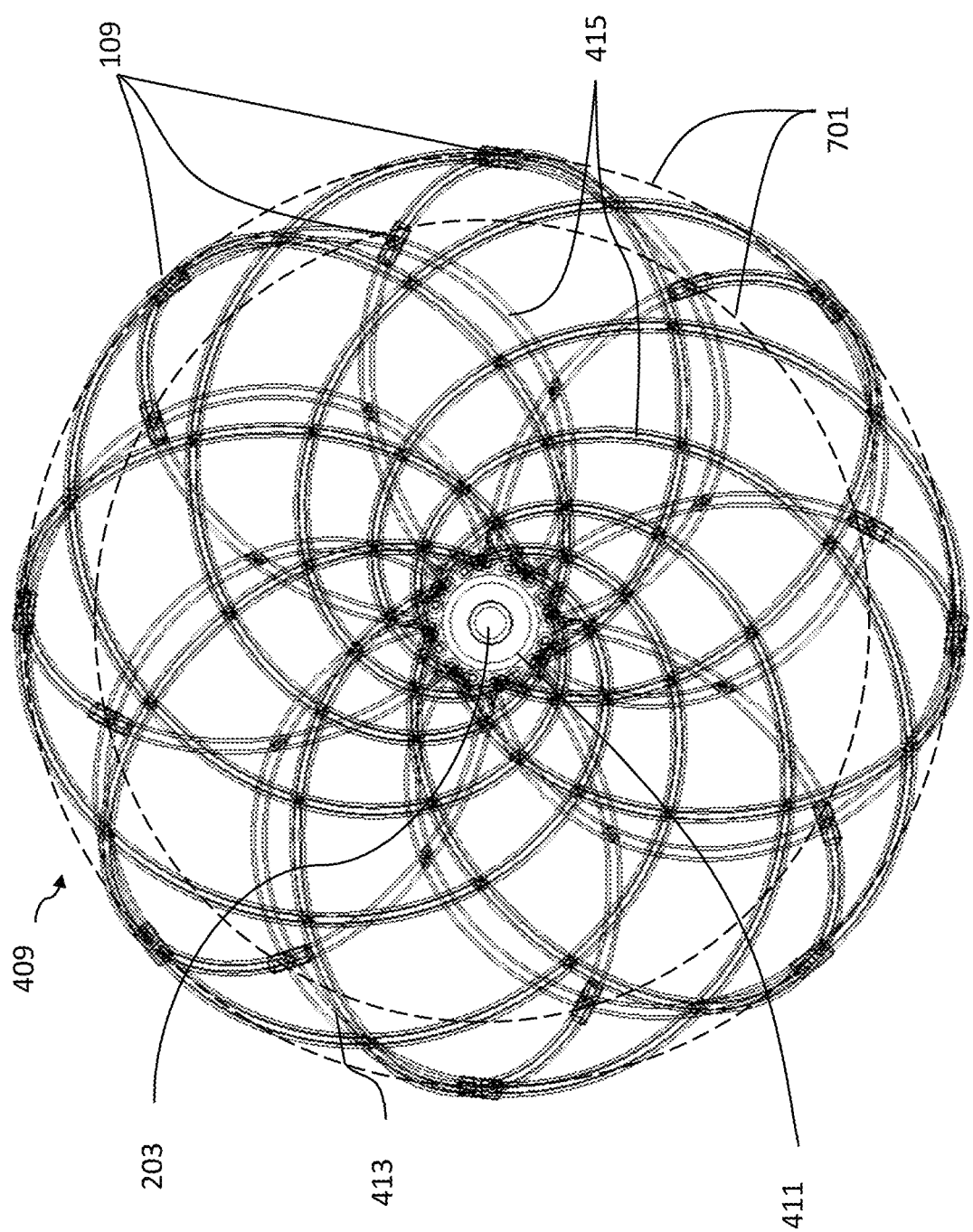
FIG. 7A is a front view of an exemplary distal tip of a catheter.

The pattern (701) created by the electrodes (109) may be for example a circular pattern in space around the longitudinal central axis (203) at least when the expandable basket (409) is in one of its expanded configurations as can be seen in FIG. 7A. Other two dimensional or three-dimensional patterns created by the electrodes (109) are possible. The patterns (701) may be centered around the longitudinal central axis (203) or not. The patterns (701) may have different shapes, including but not limited to circular, ellipsoidal, square, rectangle, polygonal, planar or other or the placement of the electrodes (109) on the expandable basket can be irregular. There can be for example one pattern (701) in one plane or more patterns (701) in one plane or more patterns (701) in different planes.

Figure 7B:
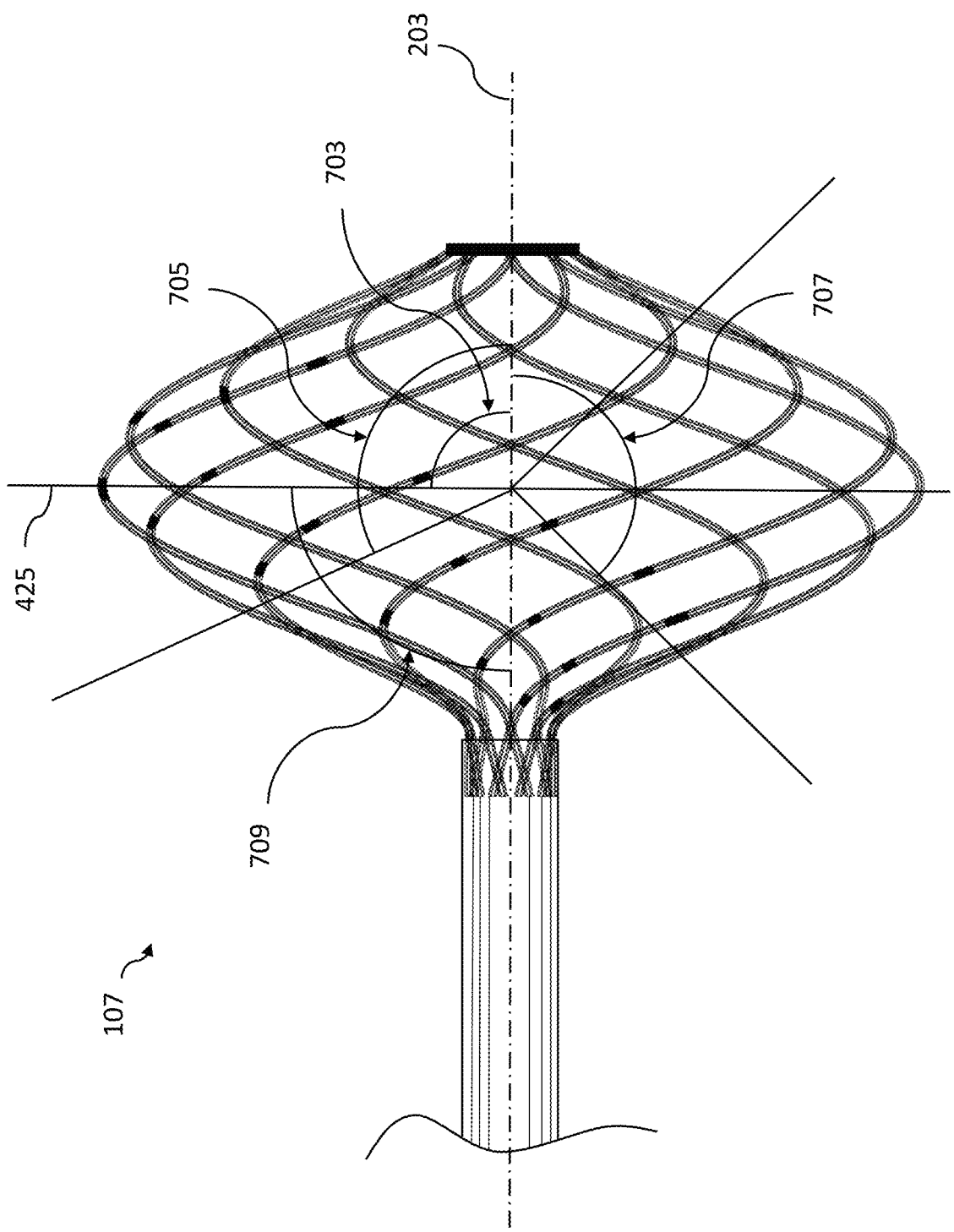
FIG. 7B is a side view of an exemplary distal tip of a catheter.

Patterns created by the electrodes may be positioned on the basket assembly body, particularly on the distal body portion, central body portion or proximal body portion as shown in FIG. 7B. Patterns may even extend into more than one of these portions. For example, for a treatment of a flat treatment site positioned distally from the basket assembly, the pattern of electrodes may be positioned advantageously on the basket assembly distal portion. Particularly the pattern may be positioned in a section of the basket assembly bounded by an area making an angle (703) of 0° to 90° to the central axis (203) in a center of a plane (425) intersecting the basket assembly in a portion with a highest diameter (in one of its expanded configurations). In some configurations, a pattern may be positioned partially on the basket assembly body distal portion and partially on the basket assembly body central portion. In some configurations, a pattern may be positioned in a section of the basket assembly bounded by an area making an angle (705) of 0° to 120° to the central axis (203) in a center of a plane (425). Such placement of the pattern may be particularly advantageous for treatment of a vessel orifice, for example an orifice of a pulmonary vein. In situations where the treatment site has a tubular shape, the pattern may be placed on the basket assembly middle portion, particularly in a section of the basket assembly bounded by areas making an angle (707) of 45° to 135° to the central axis (203) in a center of a plane (425). If a flat treatment site is positioned proximally from the basket assembly, for example a septum, the pattern of electrodes may be positioned on the basket assembly proximal body portion or partially on the proximal body portion and partially on the central body portion, particularly in a section of the basket assembly bounded by areas making an angle (709) of 90° to 180° to the central axis (203) in a center of a plane (425). Optionally electrodes may be placed in all portions of the basket assembly, thus creating patterns in all of the portions and only patterns necessary or optimal for performing a particular therapy may be chosen to perform the therapy.

Particular patterns may be created by all electrodes placed on the expandable basket or with just a portion of the electrodes. The patterns may have different numbers of electrodes in various expanded positions between fully collapsed and fully expanded positions of the expandable basket. The neighboring electrodes in the pattern may have distances between each other for example 0.1 mm-15 mm, or 0.5 mm-10 mm, or 1 mm-6 mm or 2 mm-4 mm.

Figure 8:
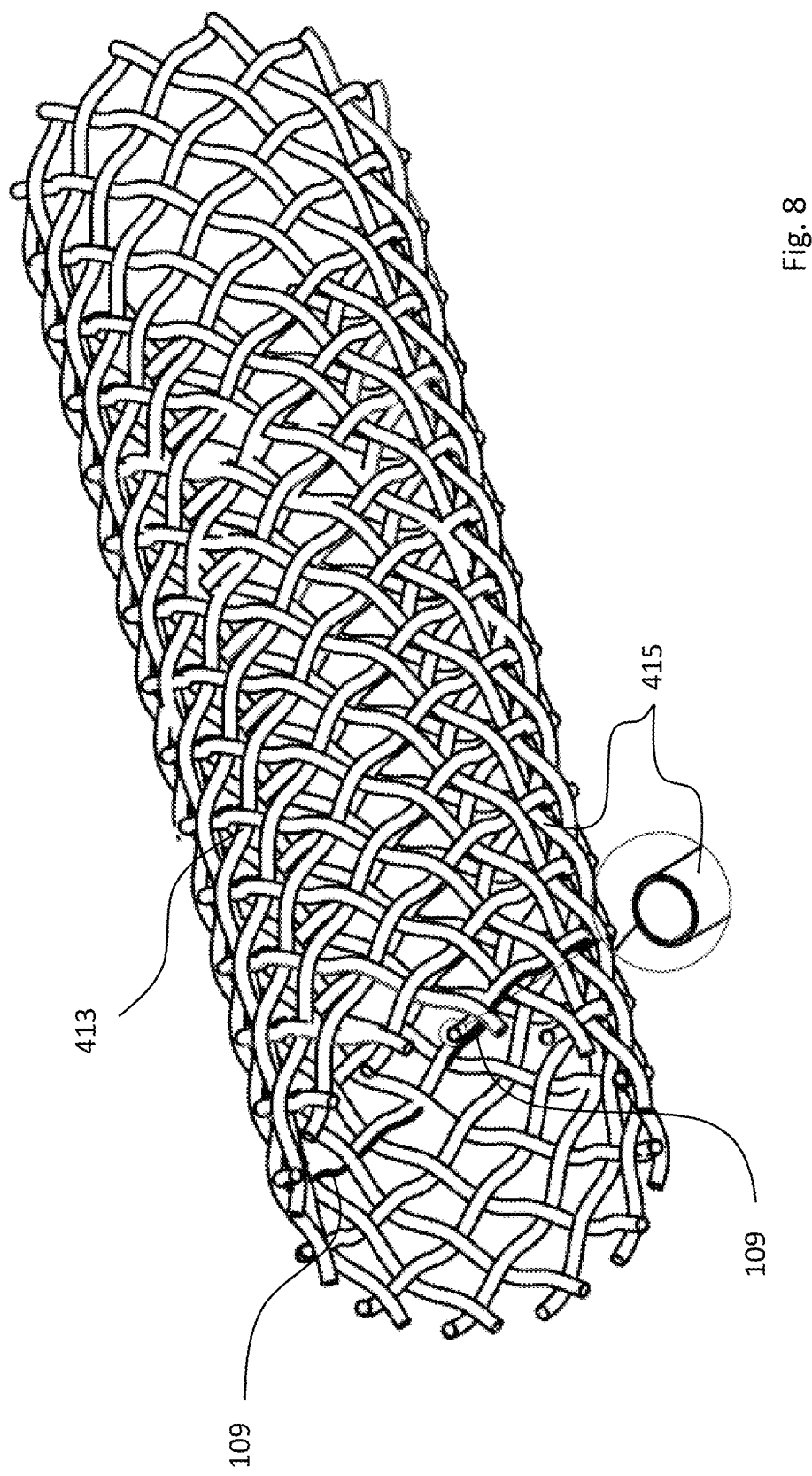
FIG. 8 shows an exemplary braided mesh with elongated electrodes.

Electrodes are for example electrically connected to the pulse generator, for example with conductive wires. The electrodes may be electrically or communicatively connected to other units or parts of the pulsed field ablation device as well as for example with the mapping device, EP display device, pacing device, ECG recording device, catheter signal interconnection circuits, ECG triggering circuits, electrical control circuits, GUI unit or remote control unit. Apart from the ring-shaped electrodes mentioned before, the electrodes may have any of many different shapes, for example tubes threaded around the filaments, coiled metal sheets, square and/or rectangle or other shapes of conductive materials attached to the filaments. Other possible forms of electrodes (109) may be elongated continuous electrodes drawn along the surface of a portion of the filament (415) in a way they do not touch at crossing points of the filaments (415) in the braided mesh (413) as shown in FIG. 8. The electrodes (109) may be attached on the particular filaments (415) of the expandable basket by any means, for example by way of mechanical attachment, swagging, crimping, gluing, lamination, deposition and/or soldering. The electrodes may be made out of any electrically conductive material for example copper, gold, steel, titanium, platinum, platinum-iridium, and so on. In a case where there is at least one filament made out of conducting material, it could serve as an electrode as well. In a case where the whole conducting filament is uninsulated the whole filament may serve as an electrode, in case the filament is for example partially electrically insulated, the bare, uninsulated portion may serve as an electrode.

Figure 9:
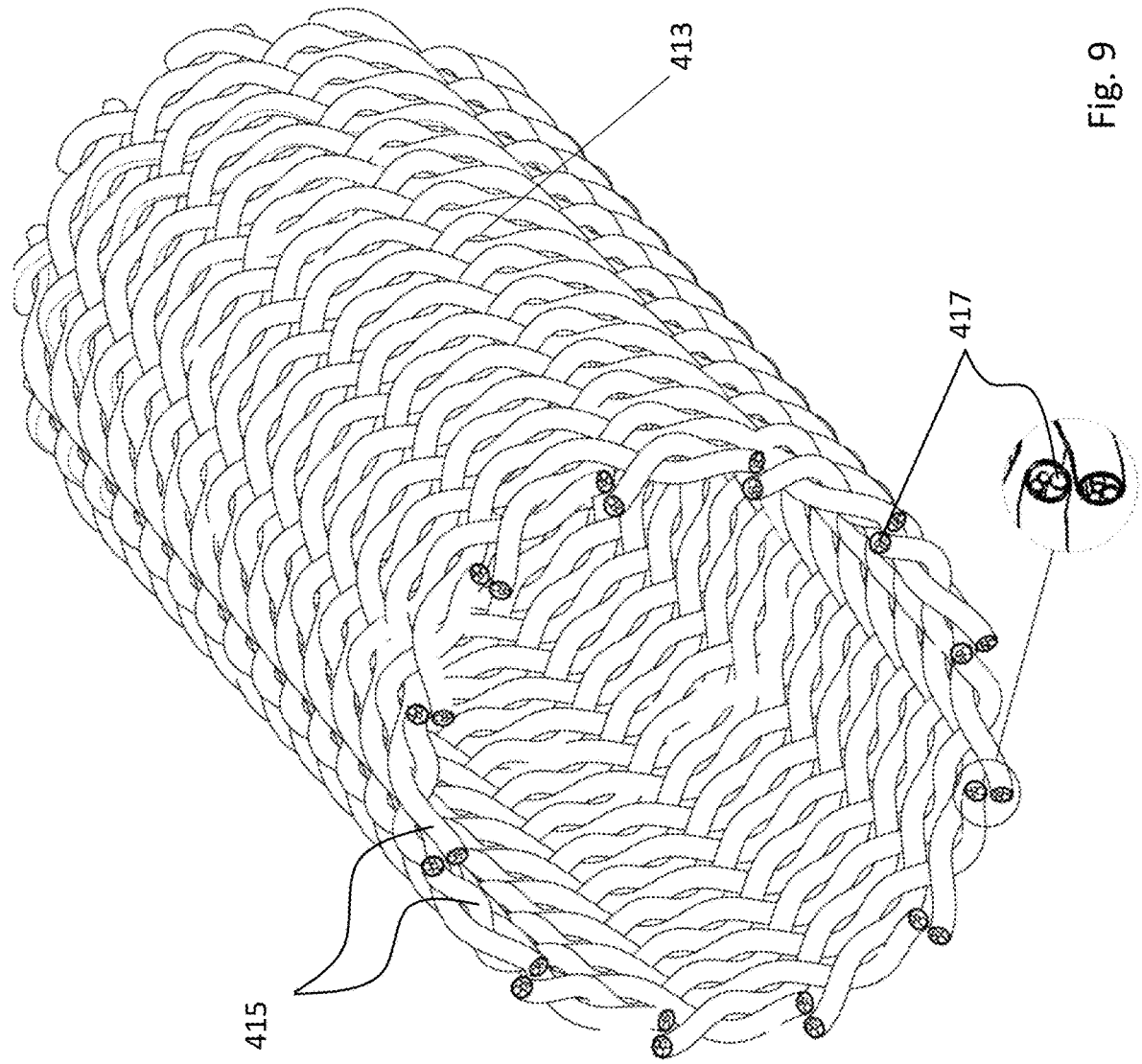
FIG. 9 shows an exemplary braided mesh with filaments and conductive wires inside of the lumen of the filaments.

Conductive wires may provide an electrical connection between the electrodes and a pulse generator. The conductive wires may be a part of a structure of the basket assembly (401). For instance, the conductive wires (417) may be positioned at least partially in the lumen (601) of the filaments (415) as shown in FIG. 6C or in FIG. 9. There can be one or more conductive wires (417) coupled to each of the electrodes, or one or more electrodes can be coupled to a single leading wire. The conductive wires (417) may be incorporated into the one of the walls of the shaft assembly, for example into the wall of the outer elongated shaft. The conductive wires can also be positioned in the central lumen of the outer elongated shaft or there can be separate lumens in the outer elongated shaft suitable for the placement of conductive wires. The conductive wires may be terminated adjacent to the electrodes or may lead spatially further along the length of the filament past the electrode. The conductive wires may for example be positioned along the whole length of the filaments of the basket assembly. Optionally some of the conductive wires (417) may be terminated adjacent to the electrodes while others may lead spatially further along the filaments past the electrode or may be positioned along the whole length of the filaments of the basket assembly.

In a case where the conductive wires are positioned along the whole length of the filament, the design solution of the expandable basket, where the filaments are bent and returned to the expandable basket, rather than cut, at the expendable basket's distal end is particularly advantageous. Because the particular conductive wires are configured to carry electrical pulses between electrodes and the pulse generator, an insulation of the cut filaments with the conductive wires inside would be extremely challenging at the terminal assembly. On the other hand, in examples comprising bent filaments with conductive wires inside, the insulation of the terminal assembly can be easily assured.

The material used for conductive wires may be any electrically conductive material for example copper, stainless steel, steel, nitinol, aluminum, gold, platinum, silver and so on. The conductive wires may be insulated or uninsulated. The wires may be insulated using any suitable material, for example polyimide, polyurethane, polyester, polyvinylchloride (PVC), rubber, rubber-like polymers, nylon, polyethylene, polypropylene, silicone, fiberglass, ethylene propylene diene monomer (EPDM), different fluoropolymers like polytetrafluoroethylene (PTFE) and so on. The wires may be made of a single conductor or with a group of conductors, whereas a wire made of a group of conductors is sometimes called "cable". In case the wires are insulated a minimum breakdown voltage of the wire insulation should be at least 100V, or 500V, or 1000V or 4000V or 10000V. The diameter of the wires with insulation may be limited by the dimensions of other structures of the device such as for example the filaments and a minimum voltage it has to be able to carry without risk of breakdown. Typical diameter of the wires with or without insulation may be between 0.05 mm and 0.7 mm, or between 0.07 mm and 0.5 mm, or 0.1 mm to 0.3 mm or between 0.11 mm to 0.2 mm or between 0.12 mm to 0.18 mm.

The construction of the braided mesh out of electrically insulating material as described with one or more conductive wires inside hollow filaments may be particularly advantageous for an ablation system based on the principle of pulsed field ablation by pulsed electric fields. The pulsed field ablation method as described further, requires electric fields generated around electrodes. To generate the fields, electrical pulses have to be carried by particular conductive wires between the electrodes and the pulse generator. When the filaments are electrically nonconductive, and the conductive wires are kept inside the filaments as described herein, the electrical insulation of the particular conductive wires can be ensured even at voltage levels of several kV, for example from 1 kV to 10 kV, carried by the conductive wires. However, an option of braided mesh with at least one or more filaments made out electric conducting material (for example nitinol, copper, stainless steel, steel, aluminum, gold, platinum or silver) may be possible as well. Such conducting filaments may be insulated or not or only partially. They not only that could possibly lead electrical current, but could act as an electrode (when uninsulated or insulated only partially) and/or as a further mechanical support of the braided mesh hence the expandable basket.

Another advantage of a braided mesh made of polymer or thermoplastic elastomer filaments is the ease of manufacturing compared for example to a metallic braided mesh. The braided mesh may be for example made with the help of a three-dimensional mandrel device. The particular filaments creating the braided mesh may be placed over the mandrel in a desired pattern. The filaments may already include the conductive wires. The whole structure may then be heated up, for example close to the melting point of a material of the filaments and after that the structure may rapidly be cooled down. The filaments made of thermoplastic elastomer or polymers generally require lower temperatures to reach the melting point over most metals, so the manufacturing process can be faster, more efficient and can demand less energy input. Another advantage of such a manufacturing process is the conductive wires do not need to be heated to extreme temperatures, to a degree where the electrical properties of the wire may be compromised. This situation can happen, for example when the braided mesh is made of the metallic wires (metallic filaments), where the braided mesh wires (filaments) also serve as the electrically conductive wires.

The braided mesh with inserted conductive wires may be attached to the outer elongated shaft and inner elongated shaft creating an expandable basket and part of the basket assembly. The electrodes may be attached at the particular filaments of the braided mesh before or after the attachment of the braided mesh to the elongated shafts. The pulse generator is a part providing generation of electric signals for catheter electrodes. The pulse generator may allow settings for example of an amplitude, a shape of the electrical pulse and/or a number of pulses during activation. The pulse generator may diagnose electrical waveforms to measure power as well. The pulse generator may enable synchronous operation with an ECG device or another part of the ablation system or device.

Further, a method of ablation with the described pulsed field ablation device is disclosed.

One method comprises the step of disposing a catheter (105) adjacent to the treatment site, for example a cardiac chamber, in the patient via a blood vessel. The catheter (105) may be inserted into the blood vessel of the patient percutaneously.

Other support structures and/or devices may be used to help navigate the distal tip of the catheter to its desired location. Examples of such devices include a guide-wire or a sheath. The catheter distal tip may be delivered proximally to the treatment site in a collapsed state, for example through a sheath. In the collapsed state the diameter of the basket assembly at the catheter distal tip may be less than or approximately equivalent to the diameter of the outer elongated shaft of the catheter. Such a configuration allows easy access of the catheter distal tip proximal to the treatment site.

The treatment site may be for example located inside the body, for example in or on a heart, for example in a heart cavity, particularly for example in a left atrium of the heart. The treatment site may for example include a pulmonary vein orifice. Other locations of the treatment site may be for example all tubular tissues, organs or vessels in a body or for example tumor sites.

When the catheter distal tip is delivered to the treatment site, the basket assembly of the catheter is deployed from the collapsed or semi-collapsed configuration to one of the expanded configurations. This deployment may be caused by a pre-tension shape of the braided mesh or its filaments or by a linear displacement of the inner elongated shaft against the outer elongated shaft along a longitudinal central axis of the catheter, by a tension of an additional supportive structure for example an inner coil or balloon (not shown), or by a combination of thereof.

Figure 10:
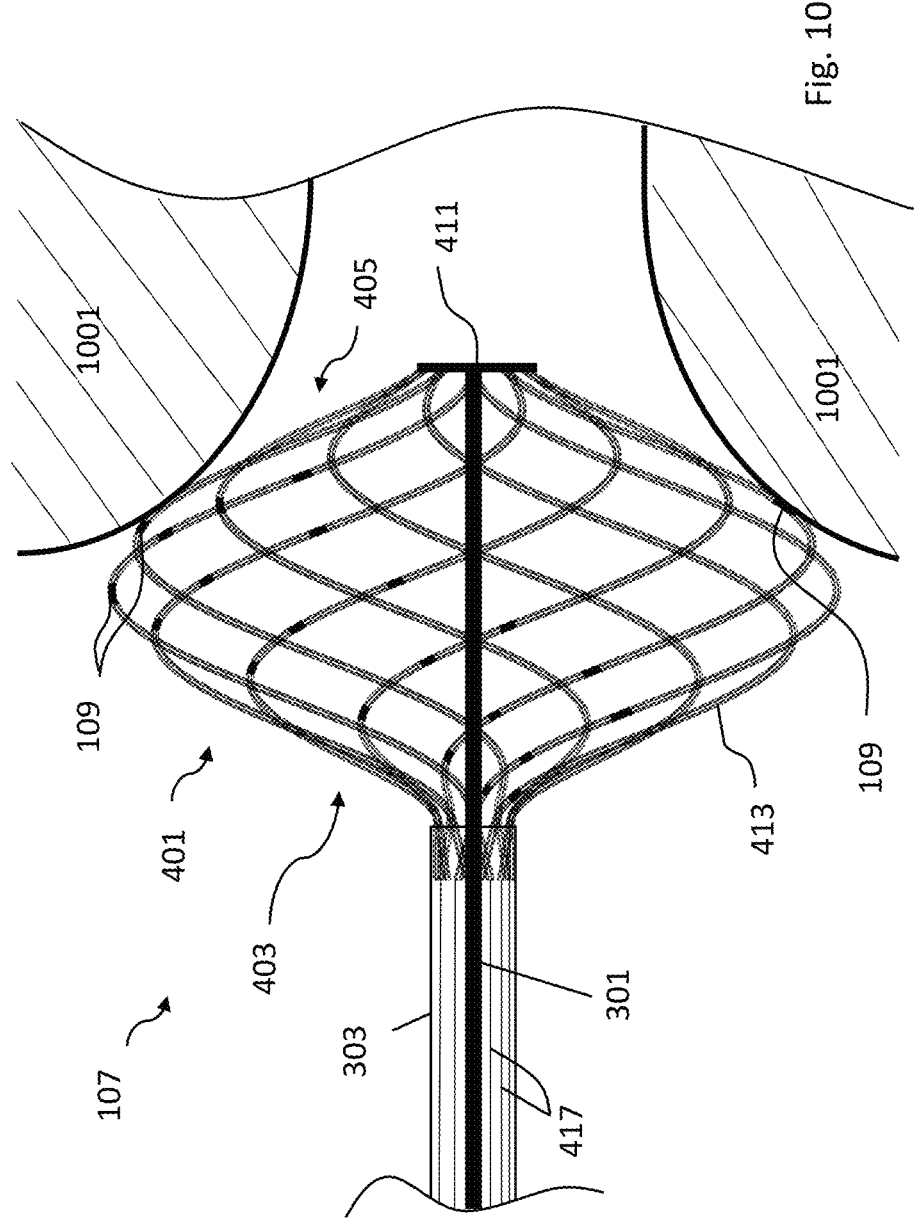
FIG. 10 is an exemplary schematic view of a position of the basket assembly adjacent to a treatment site.

The catheter distal tip (107) may then be placed adjacent to a target tissue of the treatment site (1001), for instance at least part of the basket assembly (401), and/or part of the expandable basket (409) is brought in contact with the treatment site (1001). In this position at least a portion of the set of electrodes (109), placed on the basket assembly (401) may be in contact with the tissue of the treatment site (1001). A schematic of an example position can be seen in FIG. 10. The terminal assembly (411) may improve contact of the electrodes with the treatment site by its flat design without distally protruding structures. When there are no distally protruding formations on the basket assembly (401), especially on the basket assembly distal portion (405), it is easier to get the electrodes in contact with the treatment site even in situations where the treatment site is relatively flat.

After positioning the catheter distal tip adjacent to the treatment site an optional step of measurement can be carried out with or without the catheter. Different kinds of measurements can be performed with the goal of, for example, diagnostics of type or quality of a tissue at or around the treatment site, spatial position of the catheter distal tip, particularly for example the spatial position of the catheter distal tip against the treatment site, contact of the catheter distal tip and/or particular electrodes with the target tissue of the treatment site or with a goal of understanding electrophysiological processes of a tissue adjacent to the electrodes. For example, the electrodes may be used for a measurement of contact with a target tissue as well and may be placed on the expandable basket, for example on the filaments of the braided mesh. The measurement electrodes may be different electrodes than the ablation electrodes or the ablation electrodes may be used for the measurements. It is possible to combine separate measurement electrodes with the ablation electrodes with measurement functions on one catheter distal tip as well. A separate measurement device may be used to carry out the measurement step, for example a separate measurement catheter (not shown), an ECG device including ECG triggering circuits, an ECG recording device, ECG electrodes, an intracardial ECG (EGM), an intracardial echo device, an esophagus temperature measurement device, a fluoroscopy device, RTG device, MR device, and so on. The measurement step may be carried out once or may be repeated several times during an ablation procedure.

The ablation of the target tissue of the treatment site (1001) for instance uses a principle of pulsed field ablation caused by pulsed electric fields of proper parameters. Although the terms "electric fields" or "pulsed electric fields" are mentioned here, electric fields as contemplated herein may further comprise a magnetic component.

The procedure of basket assembly deployment, measurements and ablation can be carried out in several stages. For example, the expandable basket may be delivered adjacent to the treatment site in a fully collapsed configuration. After delivery it can be deployed to its first expanded configuration. For example, the pre-tension shape of the braided mesh and/or filaments may cause this first transition. In this configuration for example further manipulation with the basket assembly can be carried out as well as measurements and/or ablation. Further repositioning, measurement and/or ablation can be carried out in this position in any order as well.

Then the basket assembly may be deployed into a second expanded configuration. The second expanded configuration can be achieved for example by a linear displacement of the inner elongated shaft against the outer elongated shaft along a longitudinal central axis of the catheter. In this configuration for example further manipulation of the basket assembly can be carried out as well as measurements and/or ablation. Further repositioning, measurement, and/or ablation can be carried out in this position in any order as well.

The basket assembly can be for example deployed into several different expanded positions, during which further repositioning, measurement and/or ablation can be carried out.

In the case of pulmonary vein isolation ablation the set of electrodes may create a circular shape around the pulmonary vein orifice. After the ablation the shape of the ablated tissue may have a circular shape around the pulmonary vein orifice as well. Several such shapes of ablated tissue may be created by repositioning the basket assembly or by switching between different electrodes.

The pulsed electric field (PEF) is for instance created by electrical pulses, for example high frequency electrical pulses. The electrical pulses may be generated by a pulse generator and may be delivered to the target tissue by the electrodes in the form of a pulsed electric field (PEF) which may be placed on the catheter distal tip and which may be in electrical contact with the pulse generator. The electrical pulses can be created by a wide variety of electrical pulses ranging from monophasic (single polarity) pulses to symmetrical and/or asymmetrical biphasic pulses. The pulses may be combined with extra pre-pulses for tissue conditioning or extra measurement pulses as well. Pulses can be single pulses, or they may be repeated in trains, where parameters of the pulses may vary or remain constant. Trains of pulses can be run in sequences as well. A maximal amplitude of the pulses may depend on the target tissue, electrode's size and/or electrode's distance in order to create an electric field with a maximum electric field magnitude for example between 0.1 kV to 10 kV or between 0.4 KV to 5 kV or between 0.5 kV to 2 kV per centimeter in a target tissue volume. A duration of the pulse can be from a nanosecond range to milliseconds range, for example from 2 ns to 10 ms, or from 10 ns to 5 ms or from 10 μs to 1 ms. The shape of the pulse may be for example a square, a curve similar to exponential discharge, a rectangle, a saw, a triangle or a sinusoidal shape.

The pulses can be monophasic or biphasic. Biphasic pulses can be symmetrical or asymmetrical. The pulses can repeat from 1× to 100000×. The frequency of the high frequency pulses may vary from 0.1 Hz to 10 Hz. Amplitude (Um) of the monophasic pulses can vary from 100V up to 10 kV, and the peak-to-peak amplitude of biphasic pulses may vary from 200V to 20 kV.

Figure 16:
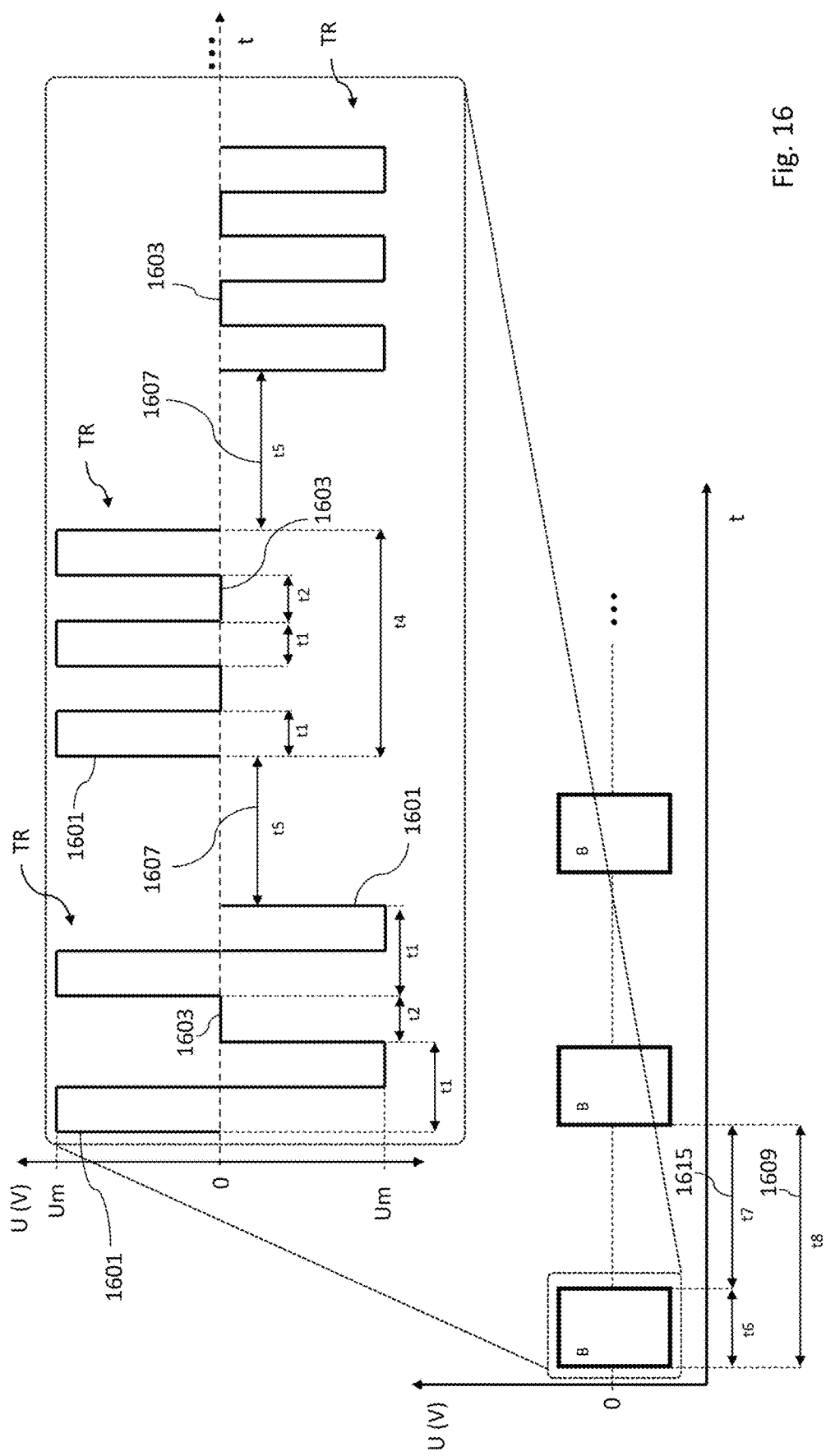
FIG. 16 shows a part of an exemplary pulsed field ablation protocol.

FIG. 16 may serve as an example of a possible part of a pulsed field ablation (PFA) protocol and as a clarification of terms and expressions regarding the PFA protocol. The PFA protocol includes a series of electrical pulses (1601) and pauses (1603, 1607, 1615). The electrical pulses (1601) may be further organized in units with a certain hierarchy like trains (TR) and bursts (B).

Figure 17A:
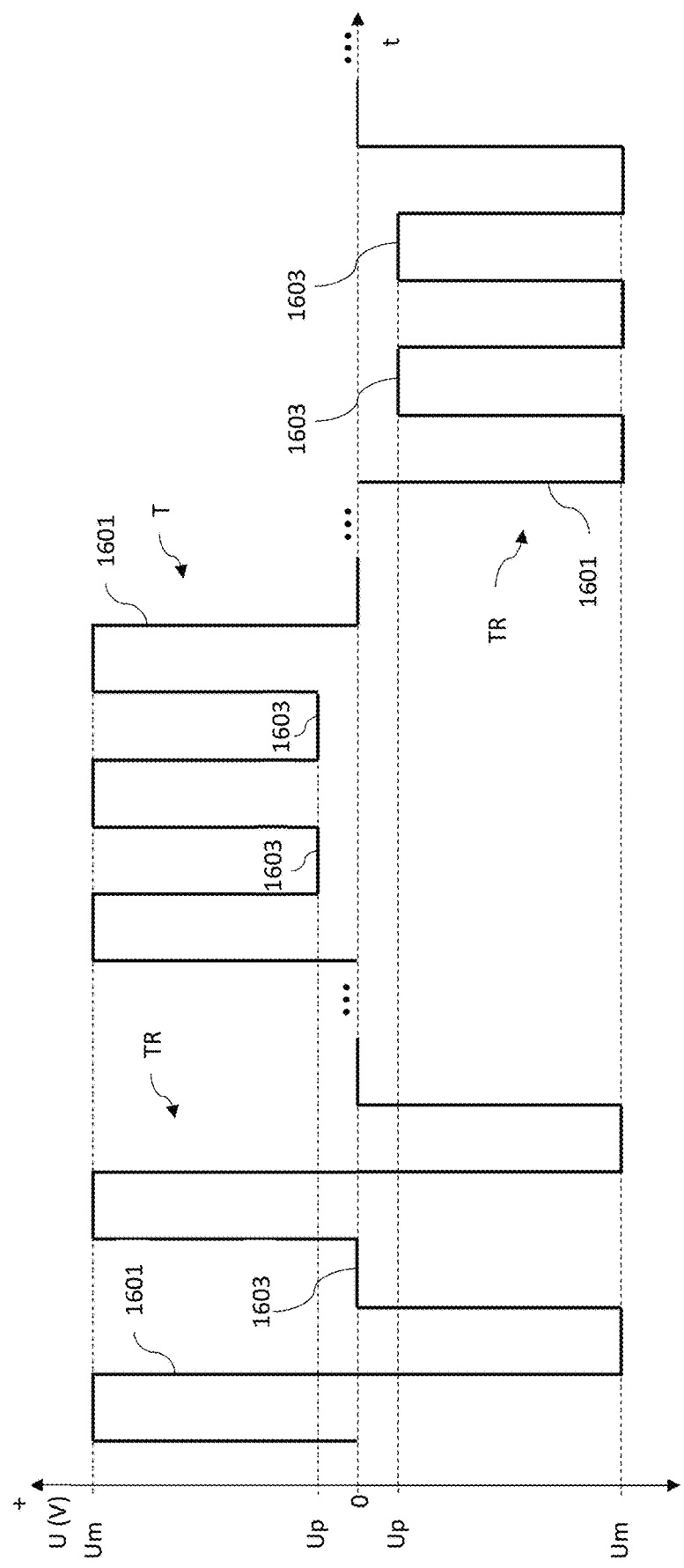
FIG. 17a shows an example of inter-pulse pauses with voltage different than 0V.

The electrical pulse (1601) may be defined for example by shape, amplitude (Um) with certain voltage and pulse length with time duration (t1). The pulse amplitude (Um) may be either negative or positive (the pulse may have negative voltage or positive voltage) in case of monophasic pulses. The electrical pulses (1601) may be separated from each other by an inter-pulse pause (1603), which is defined by a time duration (t2) and a voltage (Up). The voltage during the inter-pulse pause (1603) may drop to 0V or it may have a positive or negative voltage value (Up). The absolute voltage value (Up) of the inter-pulse pause is smaller than an absolute voltage (amplitude (Um)) of the adjacent electrical pulse (1601), particularly up to 50% of the amplitude (Um) of the adjacent electrical pulse. In situations where the electrical pulse has a positive amplitude (Um), the voltage value (Up) of the inter-pulse pause (1603) will stay positive between 0V and the electrical pulse (1601) amplitude (Um), and in situations where the electrical pulse (1601) has a negative amplitude (Um), the voltage value (Up) of the inter-pulse pause (1603) will stay negative between 0V and the electrical pulse amplitude (Um). An example of inter-pulse pauses (1603) with a voltage different than 0V is shown in FIG. 17a. Biphasic pulses may be symmetrical or asymmetrical in at least one of time, amplitude or energy.

Figure 17B:
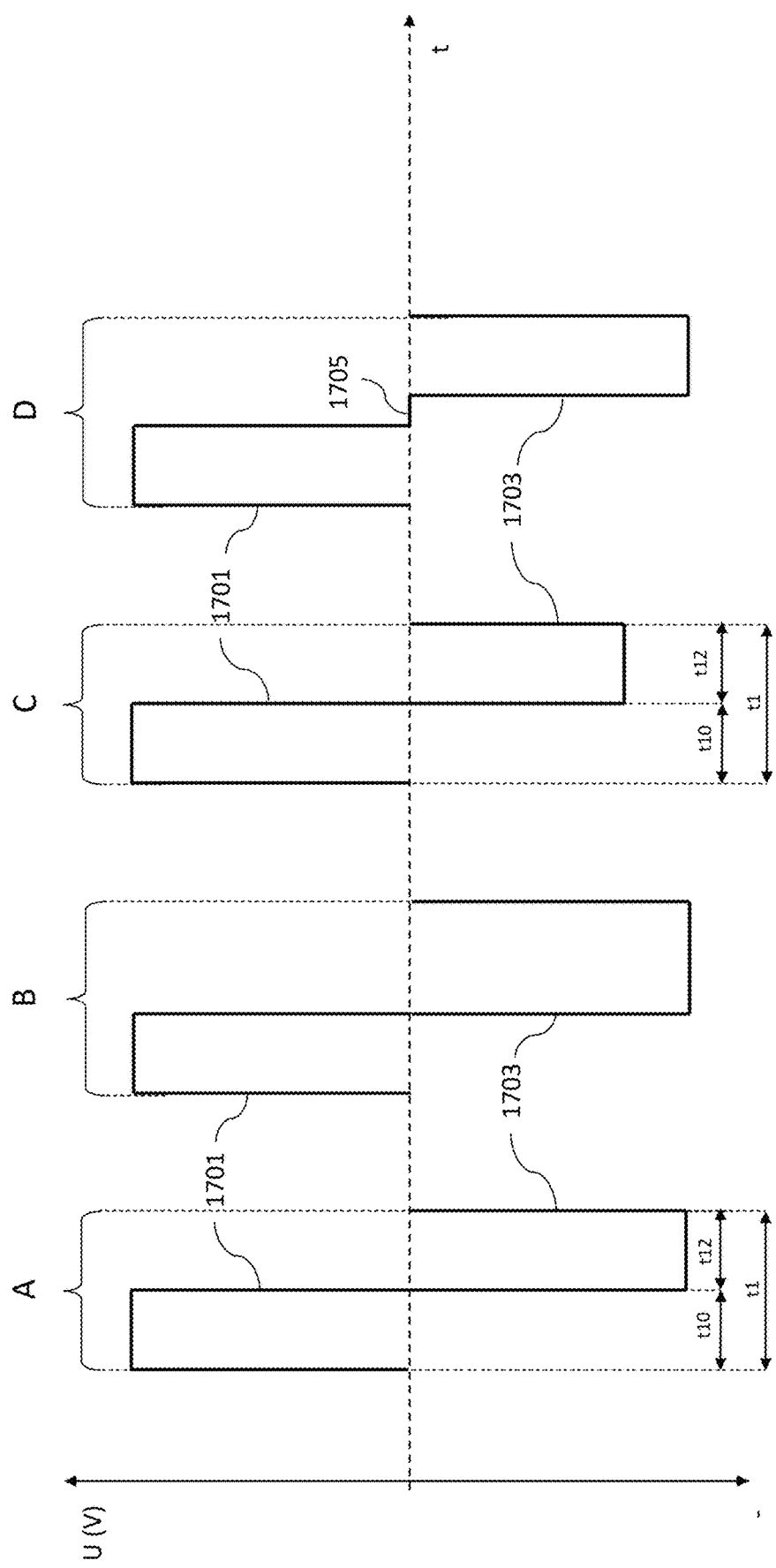
FIG. 17b shows examples of different biphasic pulses.

Examples of biphasic electrical pulses are shown in FIG. 17b. The biphasic pulses may have the same amplitude (voltage) of a positive phase (1701) and a negative phase (1703) with the same duration (t10, t12) of both phases (exemplary pulse A, D), or the amplitude and/or duration (t10) of the positive phase and the amplitude and/or duration (t12) of the negative phase may differ (exemplary pulses B, C). The resulting pulses then may have the same energy in the positive and negative phases of the pulse, or the energy in the positive and negative phases of the pulse may be different. Biphasic pulses with the same energy in both phases may be called symmetrical biphasic pulses. Symmetrical biphasic pulses may be balanced (in case the duration and amplitude of both phases of the pulse are identical, or imbalanced (in cases where the amplitude and/or duration are different in each phase). Asymmetrical biphasic pulses have phases with different energies. Exemplary biphasic pulses A, B, C are without a pause between particular phases (inter-phase pauses) of the pulse, exemplary pulse D is a biphasic pulse with an inter-phase pause (1705). The duration of the inter-phase pause of the pulse may be from 0 µs to 50 µs or from 0 µs to 10 µs or from 0 µs to 5 µs.

A series or sequence of pulses in a row, with or without inter-pulse pauses may be called a train (TR). Particular trains (TR) may be characterized for example by a time duration (t4), or number of pulses and may be separated from one another by inter-train pauses (1607) with a time duration (t5) or the inter-train pause (1607) may separate a train with an individual single pulse. A series or sequence of the trains (TR) and inter-train pauses (1607) can be called a burst (B), and may be characterized for example by a time duration (t6), number of trains (TR), number of pulses or by inter-burst pause (1615) (with time duration (t7) between particular bursts (B).

As already stated above, a voltage value (Up) at the electrodes may not decrease to 0V between pulses, particularly during inter-pulse pauses (1603) but may remain at a level, where the risk of creating bubbles by electrolysis or temperature increment is either non-existent or very small, for example up to 50% of the amplitude (Um) of an adjacent electrical pulse. This may reduce an unwanted relaxation of the polar molecules as well, which may lead to shorter length of at least some parts of the PFA protocol and so increase an efficacy of the PEF therapy.

When pulses with amplitude (Um) of hundreds of volts to a few thousand volts are applied, there is a certain risk of causing a ventricular muscle depolarization and unwanted ventricular rhythms in the heart, even when applied in a heart atrium. Depolarization can be caused directly by electric field or by secondary energy induction in another device, for example a catheter, which is placed in or near either atria or ventricles or both. Setting the timing of the active sequences (individual pulses, trains and/or bursts) with pauses described below results in an effect called overdrive. The overdrive effect is commonly used in ablation catheterization procedures to suppress a risk of unwanted heart rhythms by using an external pacemaker. An advantage of the proposed PFA protocol is that the therapeutic (ablation) electrical pulses may, in a case where they cause a myocardium depolarization, also act as pace stimulation pulses for the heart, and therefore it is not necessary to use an additional pacing device (for example an external pacemaker) to synchronize pulses of the pacing device with the therapeutic pulses of the PFA protocol. This in turn means that in this case it is not necessary to use a pacing device to control the number of ventricular contractions per minute, detect the individual ventricular contractions from a surface ECG and then trigger the ablation pulses accordingly.

The duration (t8) of one cycle (1609) of a burst (B), and inter-burst pause (1615) between bursts, which is between 201 ms to 800 ms, is given by a range between the need to deliver pulses safely faster than the patient's actual heart rate (the overdrive effect) and the need to maintain heart rate at a safe level (which is stated to be approximately 220 beats per minute minus age). The cycle duration may be fixed or variable in the stated range (201 ms to 800 ms) within a PFA protocol, for example according to a sinusoidal or triangular function. The individual burst (B) may have a duration (t6) from 1 ms to 200 ms, or 30 ms to 180 ms, or 60 ms to 160 ms, which is a safe time to contract the heart chamber by an applied burst (B) of pulses, protecting ventricles from injury or unwanted rhythm. The burst (B) duration (t6) may too be fixed or variable in the stated range (1 ms to 200 ms) within a PFA protocol, for example according to a sinusoidal or triangular function.

This PFA protocol may have other positive effects on the ablation results, for example reducing the risk of causing an unwanted ventricular rhythm and/or maximized PEF application efficiency.

However an electroporation is described as the primary trigger of death of the myocardial cells after application of the PEF, but actual cell death may alternatively be caused for example by electrical breakdown of the membrane of cardiomyocytes, mitochondria or nucleus; by tearing individual cells/cardiomyocytes (or groups of cells) of the myocardium apart (for example, by damaging the intercalated discs, either directly by electric fields or by mechanical damage by hypercontraction); by damage to sarcolemma or myofibrils of muscle fiber; by depletion and insufficient production of ATP in cardiomyocytes due to hypercontraction; by loosening of intercellular junctions of cardiomyocytes; by muscle cell myolysis; by wrinkling cardiomyocytes either directly under the influence of the electric field or by mechanical damage by hypercontraction; by irreversible damage to the calcium cycle (whether by non-physiological function of the sarcoplasmic reticulum or ion pumps or calcium channels or calcium binding proteins); by calcium overload of the heart muscle-mitochondrial swelling (as a result of hypercontraction or damage to cardiomyocyte sarcolemma or non-physiological function of calcium channels); or by formation of reactive oxygen species (ROS) and subsequent oxidation of membrane phospholipids by PEF.

The electric fields may be created among one or more electrodes placed on the catheter distal tip and one indifferent electrode placed in the distance, for example on the skin of the patient. The indifferent electrode may in some aspects have a significantly larger surface than the sum of the surfaces of the active distal tip electrodes. This mode of action is usually called monopolar. Another option for creating an electric field is in a bipolar mode. In this mode the electric field arises between two or more, usually closely-placed or adjacent distal tip electrodes with different polarities. In this case the sum of the surfaces of active electrodes with the first polarity is similar to the sum of the surfaces of the active electrodes with the second polarity.

Figure 11:
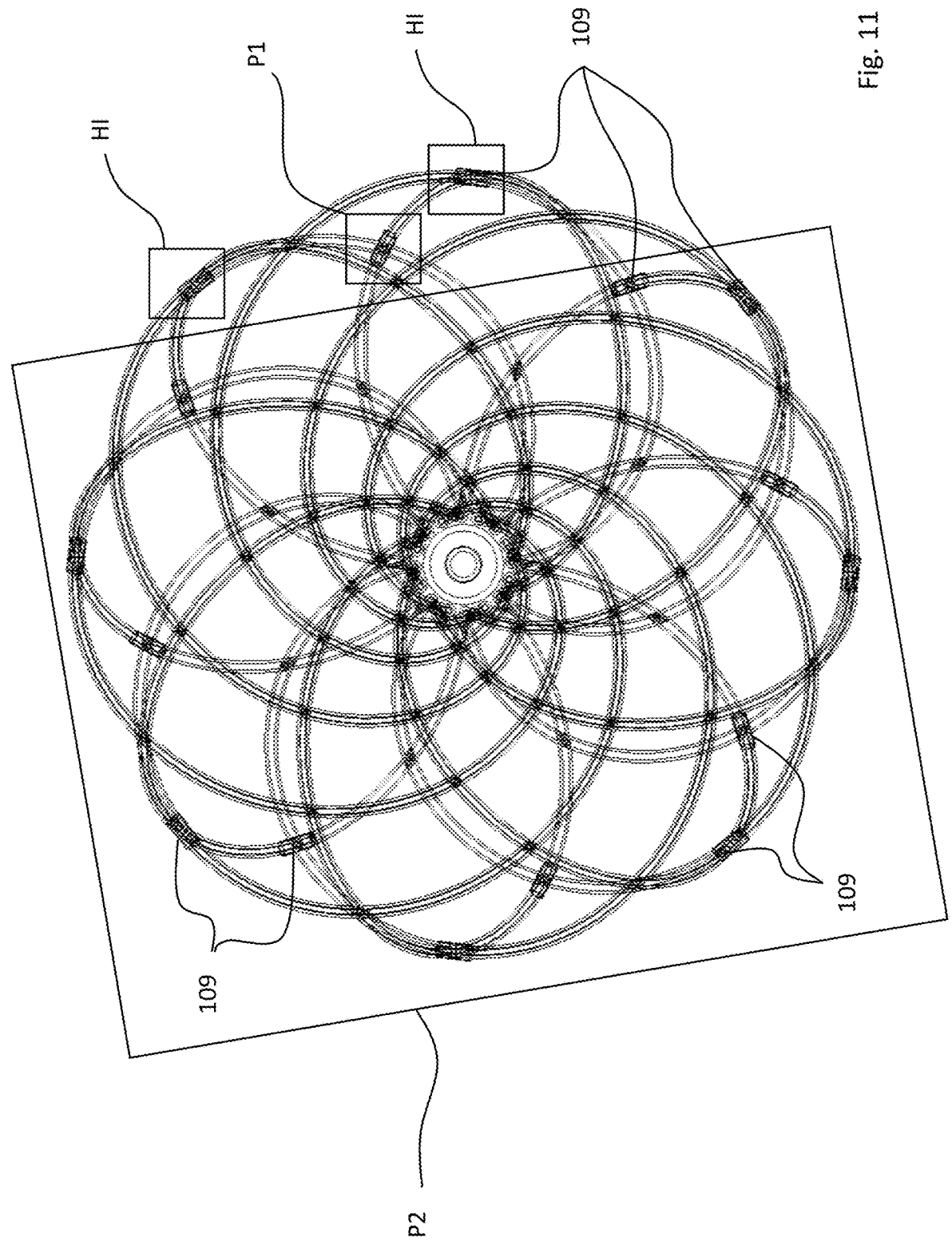
FIG. 11 is a schematic view of an exemplary mode of operation of electrodes.

In some aspects, the electrodes (109) placed on the distal assembly may be operated in a hybrid mode of the previous two types. An example of such a mode is shown in FIG. 11. Only the electrodes (109) placed on the distal tip (107) are used for ablation in this mode. There is a first single electrode, or group of electrodes operating in a mode with first polarity (P1) and a second single electrode or group of electrodes operating in a mode with different polarity (P2) (which may be an opposite polarity) than the operating mode of the first electrode or group of electrodes. A surface or a sum of the surfaces of the first electrode or the first group of electrodes is significantly smaller than a surface or a sum of the surfaces of the second electrode or group of electrodes. For example, there may be a third group of electrodes operating in a third mode in state of high impedance (HI), wherein the impedance of the electrodes in the third group is for example higher than 500Ω. The electrodes operating in the third mode may be adjacent to the electrode or group of electrodes operating in the first mode.

One advantage of the operation of electrodes in this hybrid mode is that the generated electric field may have a more homogenous current density in comparison to bipolar mode. Another advantage of the hybrid operation mode is the electric fields created in this mode may in some aspects be able to reach deeper into the target tissue compared to bipolar mode. In case of ablation of a heart cavity, the depth of the ablated target tissue, (in one example the target tissue may comprise a myocardial tissue), may be up to 5 mm.

Figure 12:
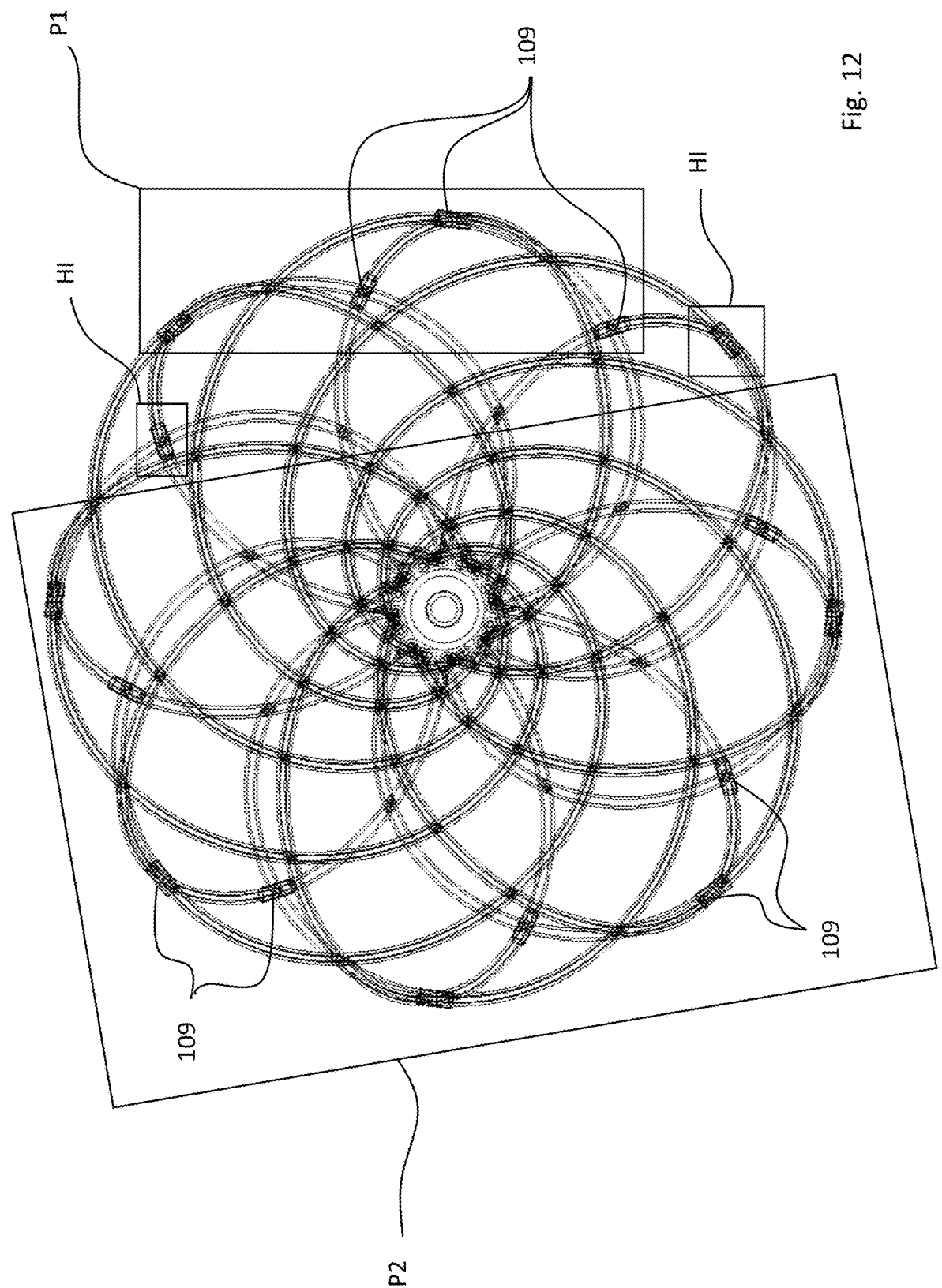
FIG. 12 is a schematic view of another exemplary mode of operation of electrodes.

A variant of the hybrid mode of operation of the electrodes (109) with a group of electrodes (more than one electrode) operating in the mode with the first polarity (P1) is shown in FIG. 12. The functional principle of this mode of operation is similar to the variant with one electrode (109) operating in the mode with the first polarity (P1). For example, the sum of surfaces of the electrodes operating in the mode with the first polarity (P1) is significantly smaller than the sum of surfaces of the electrodes operating in a mode with a different polarity (P2).

Examples with a group of electrodes (more than one electrode) operating in a mode with a first polarity (P1) can have an advantage over examples with a single electrode operating in the mode with the first polarity (P1) for example in situations where it is advantageous to reduce the size of the electrodes. Reducing the size of the electrodes can be advantageous or necessary in cases where it is necessary or desirable to increase the number of electrodes. A higher number of electrodes is desirable for example where more precise mapping of the treatment site or more precise and/or more homogenous ablation of the target tissue of the treatment site is desired. Because the treatment site can be part of a human anatomy, the overall size of the pulsed field ablation device, especially the catheter with a catheter distal tip must be restricted according to human anatomy. It follows that if more electrodes are needed for the ablation device, then for a certain number of electrodes the size of the electrodes must be limited to able to fit into the restricted dimensions of the critical parts of the pulsed field ablation device for example the catheter and/or its distal tip, and/or its basket assembly. Another advantage of the smaller size of the electrodes is that such an arrangement may help to increase a depth of the ablation.

Smaller size of the electrodes can have other advantages, for example in examples where the same electrodes are used for ablation and for measurements, it means the same electrode must be configured to deliver high voltage pulses and record measurements. For example, in measurement of ECG signals, smaller electrodes may be advantageous.

There are however some challenges associated with smaller electrodes as well. In examples including pulsed field ablation, the electric fields are for instance created among electrodes by electrical pulses, for example high frequency electrical pulses generated by a pulse generator. For effective ablation of the whole target area of the treatment site, it may be important to create an electric field with a maximum electric field magnitude of several hundred volts to several kilovolts per centimeter in a target tissue volume. Using smaller electrodes means a smaller surface area of the electrodes. With a smaller surface area of the electrodes, the voltage induced on the electrode has to be higher compared to bigger electrodes with larger surface area to achieve the desired electric field density in a target tissue. Adverse effects of such a configuration may include higher density of the electric field, higher intensity of the electric field and/or possible sparking on the edges of the electrodes. However, using a chosen group of electrodes (more than one electrode) operating in the mode with the first polarity instead of one electrode operating in the mode with the first polarity can address and overcome some or all of these issues. With a well-chosen first group of electrodes operating in the mode with the first polarity together with the second group of electrodes operating in a mode with different polarity and possibly with a third group of electrodes operating in a third mode in the state of high impedance, the first group of electrodes and/or the second group of electrodes may act as virtual electrodes. That means the electrodes in the first group may act together as one virtual electrode and/or the electrodes in the second group may act as another virtual electrode. With such a configuration, the intensity and/or the density of the electric field near the electrodes may be reduced. Other positive effects of this configuration may be a reduced risk of sparking and increased depth of ablation, or increased depth of an ablated tissue at the treatment site.

The enlargement of the surface area of the electrodes in the first group and the creation of the resulting virtual electrode may cause a reduction in the voltage needed to be induced in the electrodes and/or elimination of sparking, mainly on the edges of the electrodes. However, the concept of disproportional surface areas of the electrodes in the first and the second groups of electrodes can be preserved, which means the surface area or a sum of the surface areas of the first electrode or the first group of electrodes is significantly smaller than a surface area or a sum of the surface areas of the second electrode or group of electrodes. The ratio of the surface area of the electrode or the sum of the surface areas of the electrodes in the first group to the sum of the surface areas of the electrodes in the second group of electrodes may be between 2:3 to 1:100, or 3:5 to 1:80, or 3:5 to 1:70, or 1:2 to 1:50, or 1:2 to 1:40, or 1:2 to 1:30, or 1:2 to 1:20, or 1:3 to 1:15, or 1:3 to 1:10, or 1:4 to 1:8.

Adding electrodes to the first group of electrodes operating in the mode with the first polarity may significantly reduce the intensity of the electric field near the electrodes. Using four electrodes instead of one for example in the first group of electrodes operating in the mode with the first polarity, the intensity of the electric field at the electrode surface decreases by a factor of four, while in examples where three electrodes are used, the intensity of the electric field decreases by a factor of two. This reduction in intensity may allow for the use of lower voltage on the electrodes, compared to a solution with just one electrode operating in the mode with the first polarity. The reduction may additionally or alternatively increase of the depth of the ablated target tissue by increasing an area of the electric field with a certain voltage per cm. The value of the voltage per cm in an area of the electric field may be for example from 50 V/cm to 3000 V/cm, or from 100 V/cm to 1500 V/cm, or from 250 V/cm to 1000 V/cm.

The particular electrodes on the catheter distal tip can be switched to one or more than one of the modes during the ablation. They can be switched during one ablation cycle or during several ablation cycles. The electrodes may be switched to one or more of the modes several times during one ablation cycle or during several ablation cycles. In some aspects it is even possible to have two or more groups of electrodes operating simultaneously in a mode with the first polarity and a group of electrodes operating in a different polarity, with or without electrodes operating in a state of high impedance.

Particular electrodes may be switched to one of the modes for example before or after each pulse, before or after several consecutive pulses within a train of pulses, before or after one train or several trains of pulses within a burst of pulses or for example before or after one burst or several burst of pulses.

A layout or spatial pattern of the electrodes on the distal tip may be created with a consideration of the hybrid mode of operation of electrodes and/or with the goal of creating virtual electrodes. Because the electrodes may be switched to one or more than one of the modes during the ablation, it is possible the resulting virtual electrodes may have different spatial shapes which means the electric fields created around and between the virtual electrodes may have different shapes with different structures of the magnetic field and/or different density and intensity of the electric field. An example of a spatial pattern of electrodes on the distal tip, specifically on the expandable basket may be seen in FIG. 13A and in FIG. 13B. FIG. 13A shows a frontal view of the basket assembly (401) with a spatial pattern of electrodes (109) suitable for creation of virtual electrodes by switching the electrodes (109) into different modes of operation with the first polarity and with the different polarity and/or with a state of high impedance.

FIG. 13B shows again a frontal view of the basket assembly (401) with a spatial pattern of electrodes suitable for creation of virtual electrodes, by switching the electrodes (109) into different modes, however this time the electrodes are placed in areas where the filaments (415) cross each other (filaments crossing points).

Figure 14:
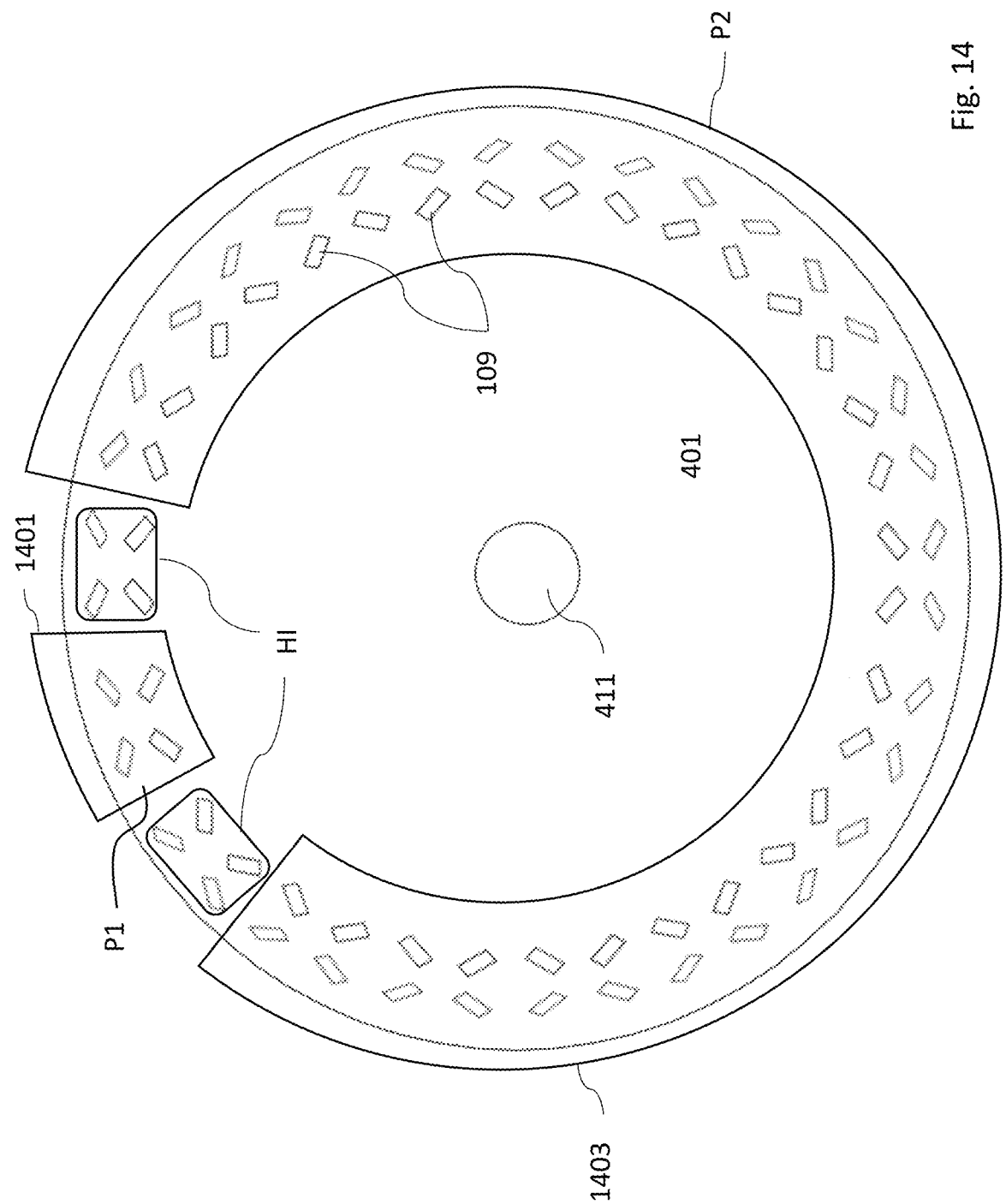
FIG. 14 is a view of a possible layout of electrodes already switched into a hybrid operation mode.

One possible layout of electrodes already switched into the hybrid operation mode may be seen in the FIG. 14, which is again a frontal view of the basket assembly (401). A first group of electrodes (109) is operating in the mode with a first polarity (P1) and together creates a first virtual electrode (1401). Another group of electrodes (109) is operating in the mode with a different polarity (P2) and together creates a second virtual electrode (1403). When electrical pulses are delivered from the pulse generator (103) to the electrodes (109) in this configuration, electric fields will be created between and around the virtual electrodes (1401, 1403). Some of the electrodes (109) may be operating in a third mode, for example in a state of high impedance (HI).

The electrodes in a state of high impedance (higher than 500Ω) may help in shaping an electric field created among and around electrodes from the first group and the second group of electrodes and/or between or around the virtual electrodes. In one example, assigning a state of high impedance to electrodes which are spatially adjacent to the electrodes operating in the mode with a first polarity may have a positive effect on the shape of the electric field in a way that a portion of the electric field which is able to cause an ablation reaches deeper into the target tissue of the treatment site, compared to an operation mode without electrodes in a state of high impedance. This phenomenon may have positive effects in the quality and homogeneity of an ablation procedure. The electrodes in a state of high impedance may be spatially placed between the first group of electrodes and the second group of electrodes.

Figure 15A:
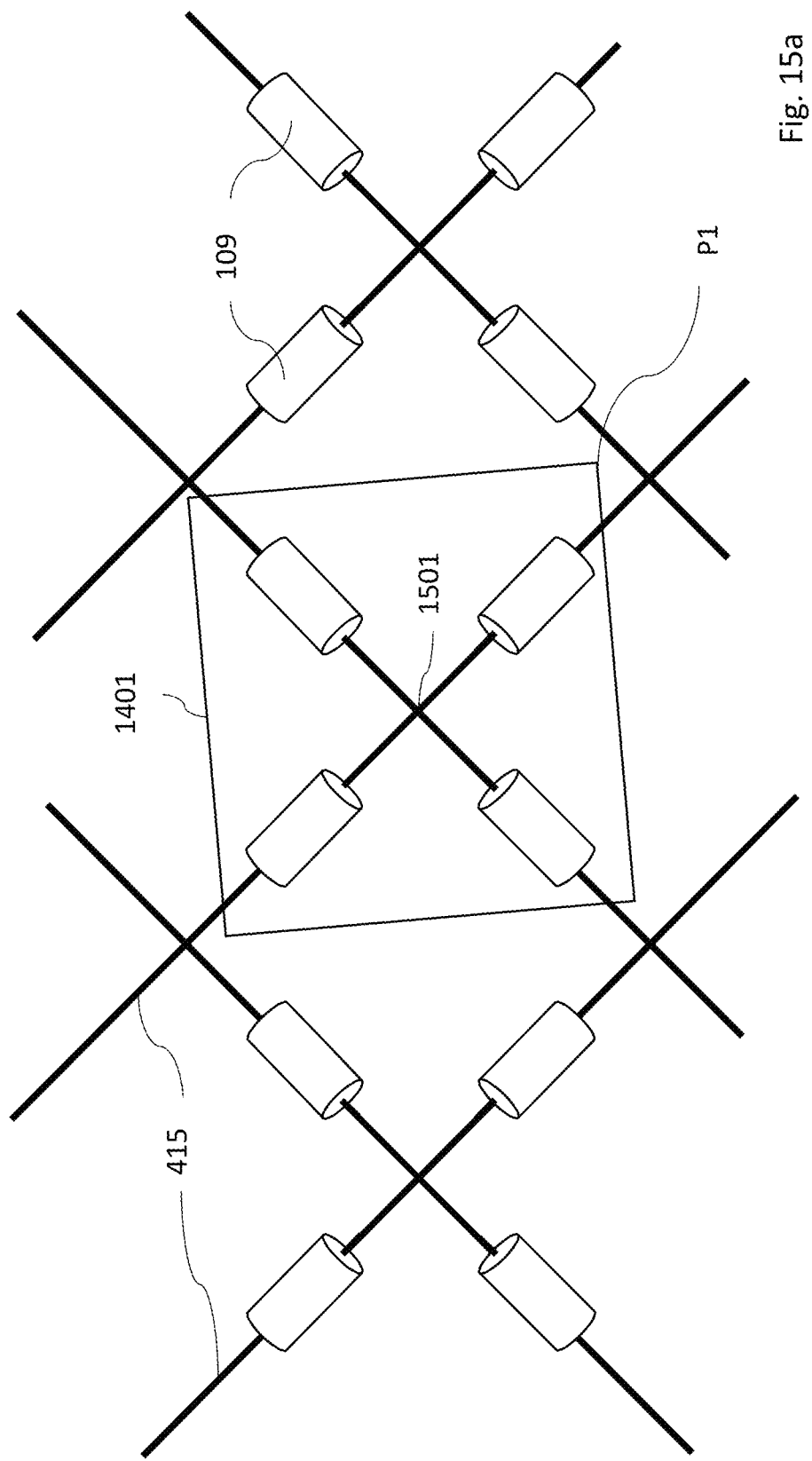
FIG. 15A shows an exemplary pattern of electrodes.
Figure 15B:
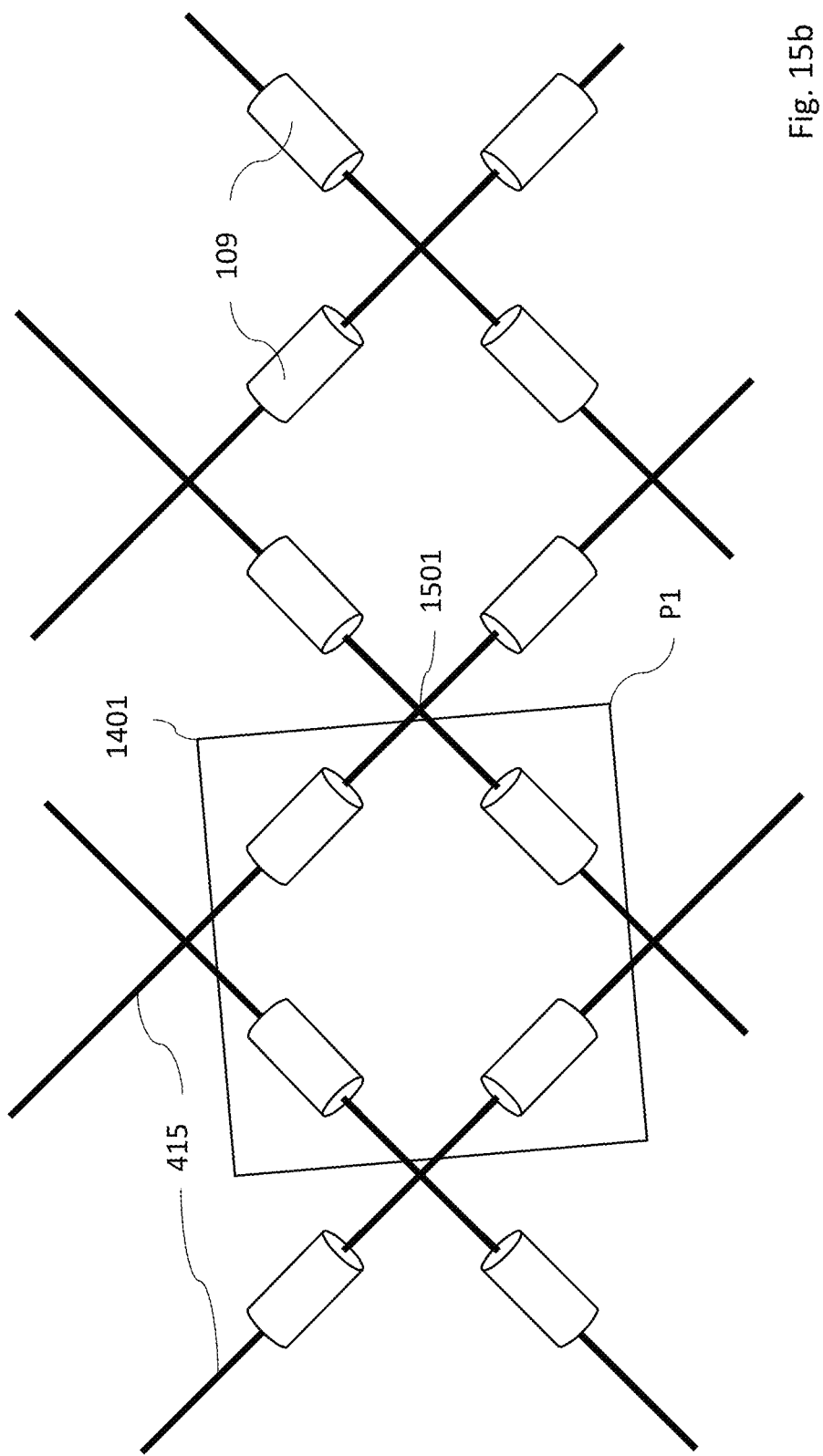
FIG. 15B shows another exemplary pattern of electrodes.

An exemplary pattern of electrodes (109) is displayed in more detail in FIG. 15A. The electrodes (109) create a pattern of repeating crosses or squares or rectangles on the filaments (415) of the braided mesh in one of the expanded configurations of the expandable basket. From this view, which is perpendicular to the tangent plane (which is touching the expandable basket for example at an intersection (1501) of four neighboring electrodes), the pattern seems two-dimensional, but in reality, it is three-dimensional, because the electrodes (109) are fixed to, or are part of the filaments (415) of the braided mesh, which creates an expandable basket, and therefore the pattern fits into the curvature of the expandable basket. This pattern of the electrodes is advantageous in embodiments using a group of electrodes operating in a mode with first polarity (P1). In this example a group of four adjacent electrodes operating in a mode with first polarity (P1) and hence creating a first virtual electrode (1401) will have either a cross shape, as indicated in FIG. 15A or a square or rectangle shape as indicated in FIG. 15B. The advantage is that both virtual electrodes (1401) created by both shapes are, in combination with a second virtual electrode, and possibly with the help of the electrodes in a state of high impedance, capable of creating electric fields having certain qualities (shape, magnitude, density, gradient of potential) suitable for the ablation of a target tissue.

Figure 15C:
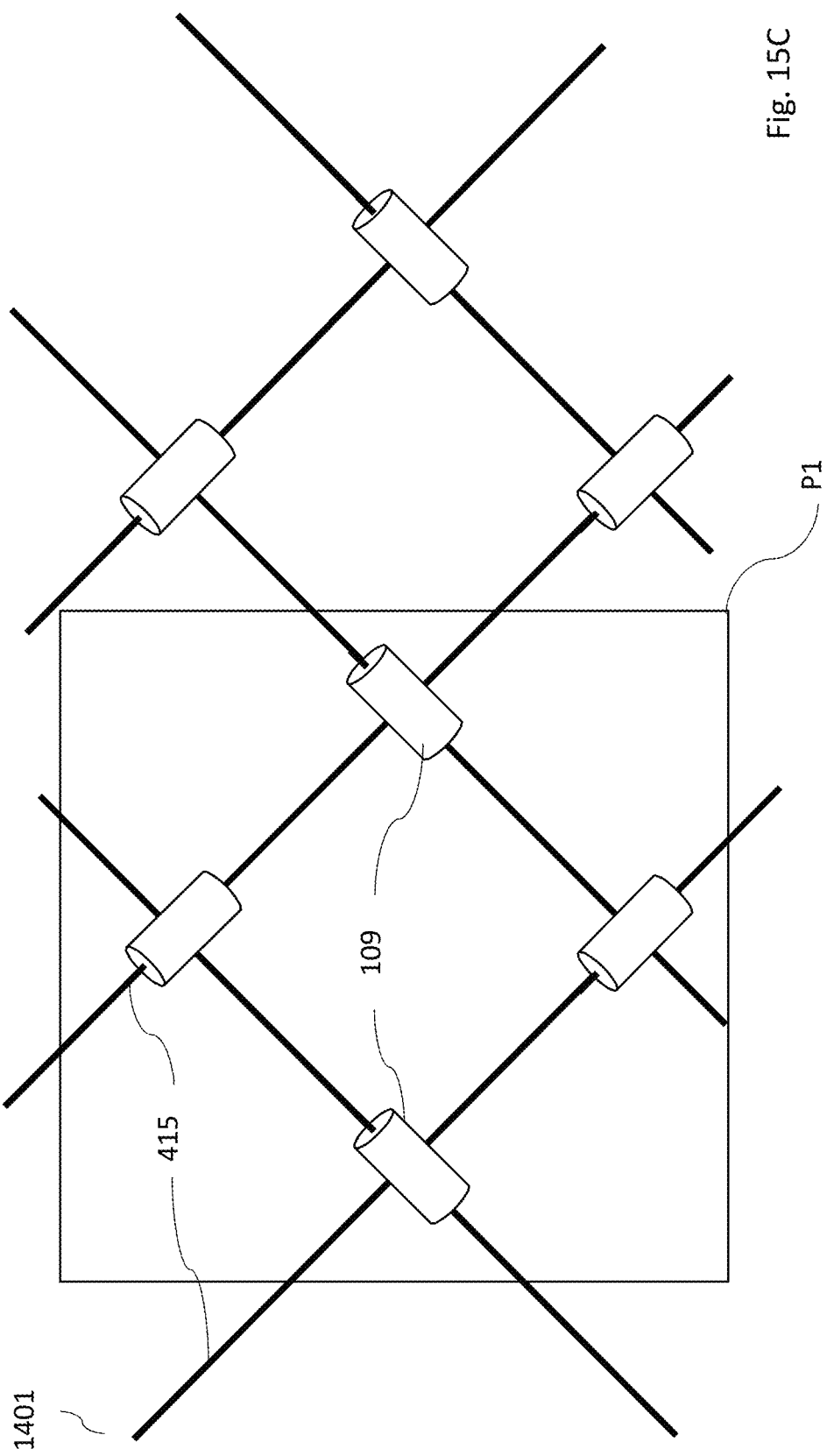
FIG. 15C shows another exemplary pattern of electrodes.

FIG. 15C shows an example of a pattern of electrodes where the electrodes (109) are placed in areas where the filaments (415) cross each other (filament crossing points). An exemplary group of electrodes operating in a mode with first polarity (P1) is also shown here.

The exact shape of the pattern of electrodes partially depends on the shape of the expandable basket. It also means the pattern and the shape of the groups of electrodes creating the virtual electrodes may be different in a collapsed configuration and/or in different expanded configurations of the expandable basket. For most of the expanded configurations of the expandable basket, the rectangles and squares created by the electrodes as described above will be inclined and will be creating shapes closer to rhombuses or rhomboids. The same applies to the angles between the two imaginary lines creating a cross and passing through the electrodes, which will not be right angles in most of the expanded configurations.

Figure 34:
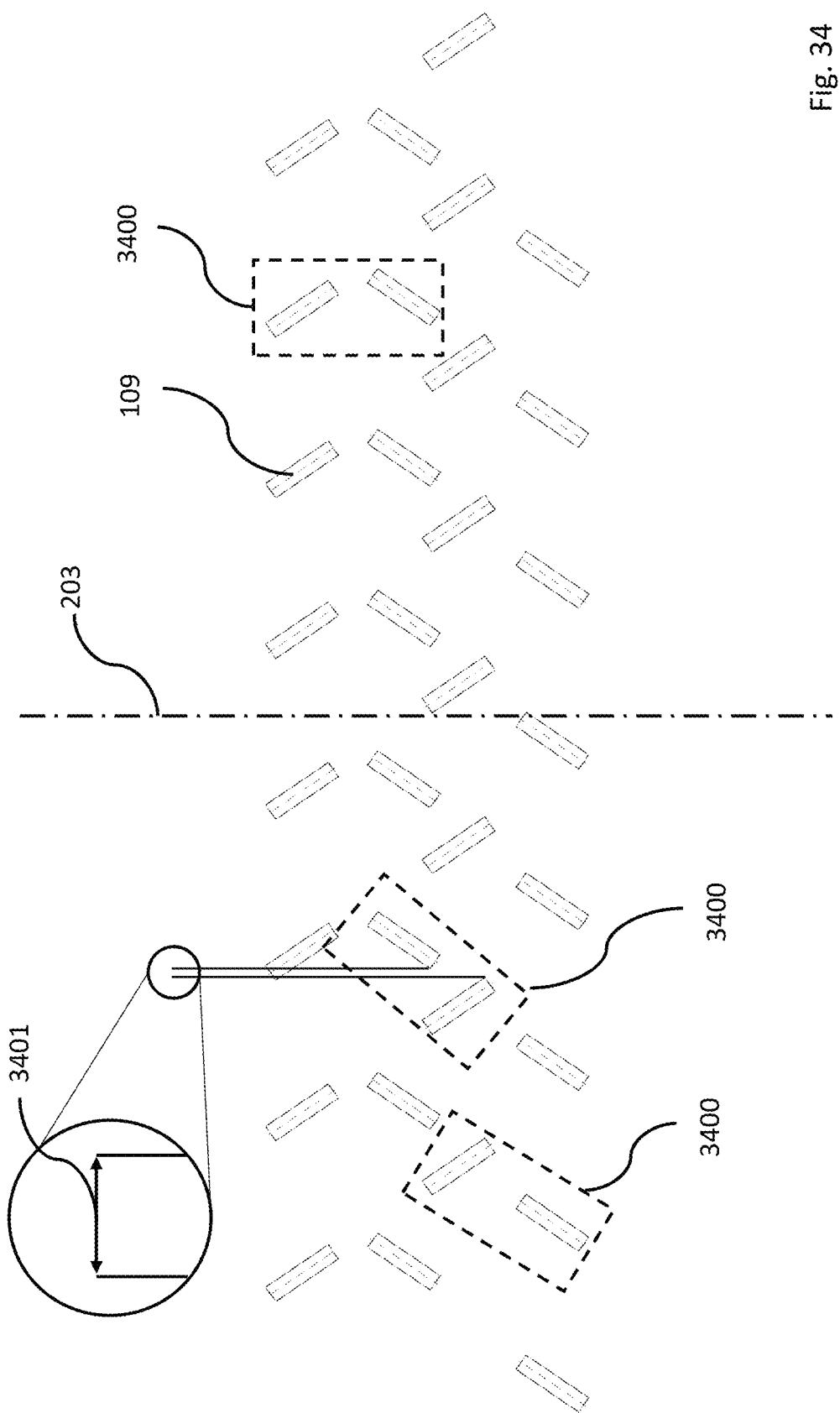
FIG. 34 shows a layout of electrodes imprinted in a two dimensional plane.

FIG. 34 shows a layout of an exemplary pattern of electrodes (109) included on the expandable basket imprinted to a flat two-dimensional plane. The electrodes are placed in the pattern such that a distance (3401) (measured perpendicularly to a central axis (203) axis +−45°) between closest points of electrodes (109) neighboring each other longitudinally in a direction of a central axis (203) +−45° is less than 2 mm in all expanded configurations of the expandable basket. An example of such a pair of electrodes (109) neighboring each other longitudinally in a direction of a central axis (203) +−45° may be seen in FIG. 34.

When using high voltage pulses in the human body, it may be necessary to synchronize the delivery of the pulses with a cardiac cycle for safety reasons, for example in order to avoid ventricular rhythm. The pulsed field ablation device can incorporate or use a means for such a synchronization including triggering of the pulse delivery by this synchronization means. The synchronization means can be for example an ECG device.

The invention claimed is:

1. An ablation device for pulsed field ablation of a tissue by a pulsed electric field, the device comprising:
    a set of electrodes; and
    a pulse generator configured to generate electric pulses and comprising a switching unit including at least one switch, the pulse generator configured to be electrically coupled to the set of electrodes via the switching unit;
    the set of electrodes configured to provide a pulsed electric field configured to cause an ablation of a tissue within a heart of a patient from the electric pulses;
    wherein the generator is configured to switch a first electrode from the set of electrodes to a mode with a first polarity, a second electrode from the set of electrodes to a mode with a second polarity different than the first polarity, and a third electrode from the set of electrodes to a mode of a state of a high impedance; and
    wherein the generator is configured to switch at least one electrode from the set of electrodes between at least two of the modes during an ablation.

2. The ablation device according to claim 1, wherein the switching unit comprises a plurality of switches.

3. The ablation device according to claim 2, wherein each switch from the plurality of switches is coupled to at least one electrode from the set of electrodes.

4. The ablation device according to claim 1, wherein the switching unit is configured to switch the first electrode from the set of electrodes to the mode with the first polarity, the second electrode from the set of electrodes to the mode with the second polarity different than the first polarity, and the third electrode from the set of electrodes to the mode of the state of the high impedance.

5. The ablation device according to claim 1, wherein the at least one switch is a semiconductor switch and includes a top transistor and a bottom transistor, and a top resistive element coupled to the top transistor and a bottom resistive element coupled to the bottom transistor.

6. The ablation device according to claim 5, wherein the top resistive element is coupled to an emitter of the top transistor and a ground; and
    wherein the bottom resistive element is coupled to a collector of the bottom transistor and a positive supply.

7. The ablation device according to claim 5, wherein the at least one switch further includes a top diode coupled to the top transistor and a bottom diode coupled to the bottom transistor.

8. The ablation device according to claim 7, wherein an anode of the top diode is coupled to an emitter of the top transistor;
    wherein a cathode of the top diode is coupled to an output of the switch;
    wherein an anode of the bottom diode is coupled to the output of the switch; and
    wherein a cathode of the bottom diode is coupled to a collector of the bottom transistor.

9. The ablation device according to claim 1, wherein the high impedance is higher than 500Ω.

10. The ablation device according to claim 1, wherein the generator includes a power supply unit and wherein the generator is configured to limit leakage currents from the power supply unit to the patient below a limit of 10 µA.

11. A pulse generator for generating of electric pulses for pulsed field ablation of a tissue by a pulsed electric field comprising:
    a switching unit including at least one switch, the pulse generator configured to be electrically coupled to a set of electrodes via the switching unit, the set of electrodes configured to provide a pulsed electric field configured to cause an ablation of a tissue within a heart of a patient from the electric pulses;
    wherein the generator is configured to switch a first electrode from the set of electrodes to a mode with a first polarity, a second electrode from the set of electrodes to a mode with a second polarity different than the first polarity, and a third electrode from the set of electrodes to a mode of a state of a high impedance; and
    wherein the generator is configured to switch at least one electrode from the set of electrodes between at least two of the modes during an ablation.

12. The generator according to claim 11, wherein the switching unit comprises a plurality of switches.

13. The generator according to claim 12, wherein each switch from the plurality of switches is coupled to at least one electrode from the set of electrodes.

14. The generator according to claim 11, wherein the switching unit is configured to switch the first electrode from the set of electrodes to the mode with the first polarity, the second electrode from the set of electrodes to the mode with the second polarity different than the first polarity, and the third electrode from the set of electrodes to the mode of the state of the high impedance.

15. The generator according to claim 11, wherein the at least one switch is a semiconductor switch and includes a top transistor and a bottom transistor and a top resistive element coupled to the top transistor and a bottom resistive element coupled to the bottom transistor.

16. The generator according to claim 15, wherein the top resistive element is coupled to an emitter of the top transistor and a ground; and
    wherein the bottom resistive element is coupled to a collector of the bottom transistor and a positive supply.

17. The generator according to claim 15, wherein the at least one switch further includes a top diode coupled to the top transistor and a bottom diode coupled to the bottom transistor.

18. The generator according to claim 17, wherein an anode of the top diode is coupled to an emitter of the top transistor;
 wherein a cathode of the top diode is coupled to an output of the switch;
 wherein an anode of the bottom diode is coupled to the output of the switch; and
 wherein a cathode of the bottom diode is coupled to a collector of the bottom transistor.

19. The generator according to claim 11, wherein the high impedance is higher than 500Ω.

20. The generator according to claim 11, wherein the generator includes a power supply unit and wherein the generator is configured to limit leakage currents from the power supply unit to the patient below a limit of 10 μA.

21. An ablation device comprising:
 a set of electrodes;
 a pulse generator configured to generate electric pulses; and
 a switching unit including at least one switch;
 the set of electrodes electrically coupled to the pulse generator via the at least one switch;
 wherein the at least one switch is a semiconductor switch, comprising:
  a top transistor;
  a bottom transistor;
  a top resistive element coupled to the top transistor; and
  a bottom resistive element coupled to the bottom transistor;
 wherein the at least one switch is configured to switch a first electrode from the set of electrodes to a mode with a first polarity, a second electrode from the set of electrodes to a mode with a second polarity different than the first polarity, and a third electrode from the set of electrodes to a mode of a state of a high impedance; and
 wherein the at least one switch is configured to switch at least one electrode from the set of electrodes between at least two of the modes during an ablation.

22. The ablation device according to claim 21, wherein the top resistive element is coupled to an emitter of the top transistor and a ground; and
 wherein the bottom resistive element is coupled to a collector of the bottom transistor and a positive supply.

23. The ablation device according to claim 21, wherein the at least one switch further includes a top diode coupled to the top transistor and a bottom diode coupled to the bottom transistor.

24. The ablation device according to claim 23, wherein an anode of the top diode is coupled to an emitter of the top transistor;
 wherein a cathode of the top diode is coupled to an output of the at least one switch;
 wherein an anode of the bottom diode is coupled to the output of the switch; and
 wherein a cathode of the bottom diode is coupled to the collector of the bottom transistor.

25. The ablation device according to claim 21, wherein the high impedance is higher than 500Ω.

26. A pulse generator for an ablation device comprising:
 at least one switch;
 wherein the pulse generator is coupled to a set of electrodes via the at least one switch;
 wherein the at least one switch is a semiconductor switch including:
  a top transistor;
  a bottom transistor;
  a top resistive element coupled to the top transistor; and
  a bottom resistive element coupled to the bottom transistor;
 wherein the at least one switch is configured to switch a first electrode from the set of electrodes to a mode with a first polarity, a second electrode from the set of electrodes to a mode with a second polarity different than the first polarity, and a third electrode from the set of electrodes to a mode of a state of a high impedance; and
 wherein the at least one switch is configured to switch at least one electrode from the set of electrodes between at least two of the modes during an ablation.

27. The generator according to claim 26, wherein the top resistive element is coupled to an emitter of the top transistor and a ground; and
 wherein the bottom resistive element is coupled to a collector of the bottom transistor and a positive supply.

28. The generator according to claim 26, wherein the at least one switch further includes a top diode coupled to the top transistor and a bottom diode coupled to the bottom transistor.

29. The generator according to claim 28, wherein an anode of the top diode is coupled to an emitter of the top transistor;
 wherein a cathode of the top diode is coupled to an output of the at least one switch;
 wherein an anode of the bottom diode is coupled to the output of the at least one switch; and
 wherein a cathode of the bottom diode is coupled to a collector of the bottom transistor.

30. The generator according to claim 25, wherein the high impedance is higher than 500Ω.

* * * * *